US011312759B2

(12) United States Patent
Yugawa

(10) Patent No.: US 11,312,759 B2
(45) Date of Patent: Apr. 26, 2022

(54) ANTIBODY CAPABLE OF BINDING TO NOROVIRUS, COMPOSITE, DETECTION DEVICE AND METHOD USING THE SAME

(71) Applicant: Panasonic Intellectual Property Management Co., Ltd., Osaka (JP)

(72) Inventor: Keiko Yugawa, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 292 days.

(21) Appl. No.: 16/513,752

(22) Filed: Jul. 17, 2019

(65) Prior Publication Data

US 2020/0062829 A1 Feb. 27, 2020

(30) Foreign Application Priority Data

Aug. 23, 2018 (JP) ............................ JP2018-156399

(51) Int. Cl.

*C07K 16/10* (2006.01)
*G01N 33/543* (2006.01)
*G01N 33/68* (2006.01)
*G01N 33/52* (2006.01)
*B01L 3/00* (2006.01)

(52) U.S. Cl.

CPC ........ *C07K 16/10* (2013.01); *B01L 3/502769* (2013.01); *G01N 33/52* (2013.01); *G01N 33/54306* (2013.01); *G01N 33/6857* (2013.01); *C07K 2317/31* (2013.01); *C07K 2317/35* (2013.01); *C07K 2317/53* (2013.01); *C07K 2317/565* (2013.01); *C07K 2317/567* (2013.01); *C07K 2317/92* (2013.01); *C07K 2319/60* (2013.01)

(58) Field of Classification Search

CPC ................ C07K 16/10; C07K 2319/60; C07K 2317/565; C07K 2317/567; G01N 33/52; G01N 33/54306; G01N 33/6857

See application file for complete search history.

(56) References Cited

U.S. PATENT DOCUMENTS

| | | | |
|---|---|---|---|
| 9,193,780 | B2 | 11/2015 | Hultberg et al. |
| 2017/0283485 | A1 | 10/2017 | Yugawa et al. |
| 2019/0002535 | A1 | 1/2019 | Yugawa |

FOREIGN PATENT DOCUMENTS

| | | |
|---|---|---|
| JP | 2011-521662 | 7/2011 |
| WO | 2014/183052 A1 | 11/2014 |
| WO | 2016/059113 A1 | 4/2016 |

OTHER PUBLICATIONS

Paul, WE (1993) Fundamental Immunology, 3rd ed. Raven Press, NY, Chap. 9, pp. 292-295.*

Rudikoff, S et al. (1982) Proc. Natl. Acad. Sci. USA, 79:1979-1983.*

Colman, PM (1994) Research in Immunology, Elsevier, NY, 145(1):33-36.*

Extended European Search Report dated Jan. 22, 2020 for the related European Patent Application No. 19192787.0.

(Continued)

*Primary Examiner* — Robert S Landsman

(74) *Attorney, Agent, or Firm* — McDermott Will & Emery LLP

(57) ABSTRACT

The present invention provides an antibody including a structural domain represented by the following amino acid sequence, in an N- to C-direction,

N-FR1-CDR1-FR2-CDR2-FR3-CDR3-FR4-C wherein the antibody further includes a protein molecule bound to the structural domain;

the structural domain is capable of binding to a norovirus;

FR denotes a framework region amino acid sequence and CDR denotes a complementary determining region amino acid sequence;

any one of the following requirements (i)-(iii) is satisfied.

Requirement (i):

the CDR1 includes an amino acid sequence having a sequence identity of not less than 60% with any one of the amino acid sequences represented by SEQ ID NO: 1-SEQ ID NO: 6, the CDR2 includes an amino acid sequence having a sequence identity of not less than 60% with any one of the amino acid sequences represented by SEQ ID NO: 7-SEQ ID NO: 12, and the CDR3 includes an amino acid sequence having a sequence identity of not less than 60% with any one of the amino acid sequences represented by SEQ ID NO: 13-SEQ ID NO: 17;

Requirement (ii):

the CDR1 includes an amino acid sequence in which one-three amino acid(s) of any one of the amino acid sequence represented by SEQ ID NO: 1-SEQ ID NO: 6 has/have been substituted, deleted, or added, the CDR2 includes an amino acid sequence in which one-three amino acid(s) of any one of the amino acid sequence represented by SEQ ID NO: 7-SEQ ID NO: 12 has/have been substituted, deleted, or added, and the CDR3 includes an amino acid sequence in which one-three amino acid(s) of any one of the amino acid sequence represented by SEQ ID NO: 13-SEQ ID NO: 17 has/have been substituted, deleted, or added; and Requirement (iii):

the CDR1 includes any one of the amino acid sequence represented by SEQ ID NO: 1-SEQ ID NO: 6, the CDR2 includes any one of the amino acid sequence represented by SEQ ID NO: 7-SEQ ID NO: 13, and the CDR3 includes any one of the amino acid sequence represented by SEQ ID NO: 13-SEQ ID NO: 17.

12 Claims, 23 Drawing Sheets

Specification includes a Sequence Listing.

(56) References Cited

OTHER PUBLICATIONS

Anna D. Koromyslova et al., "Nanobody Binding to a Conserved Epitope Promotes Norovirus Particle Disassembly," Journal of Virology, vol. 89, No. 5, Mar. 2015, pp. 2718-2730, XP55438443.
Alvarado Gabriela et al., "Human Monoclonal Antibodies That Neutralize Pandemic GII.4 Noroviruses," Gastroenterology, vol. 155, No. 6, Aug. 28, 2018, pp. 1898-1907, XP085546397.
Lorena Garaicoechea et al, "Llama Nanoantibodies with Therapeutic Potential against Human Norovirus Diarrhea," PLOS One, vol. 10, No. 8, Aug. 12, 2015, pp. 1-33, XP55612756.

* cited by examiner

Solid Phase

Solid Phase

Solid Phase

Solid Phase

SEQUENCE LISTING

```
<160> NUMBER OF SEQ ID NOS: 102

<210> SEQ ID NO 1
<211> LENGTH: 5
<212> TYPE: PRT
<213> ORGANISM: Vicugna pacos

<400> SEQUENCE: 1

Ile Gly Ala Met Gly
1               5


<210> SEQ ID NO 2
<211> LENGTH: 5
<212> TYPE: PRT
<213> ORGANISM: Vicugna pacos

<400> SEQUENCE: 2

Ser Ser Ala Met Ala
1               5


<210> SEQ ID NO 3
<211> LENGTH: 5
<212> TYPE: PRT
<213> ORGANISM: Vicugna pacos

<400> SEQUENCE: 3

Leu Gly Ala Met Gly
1               5


<210> SEQ ID NO 4
<211> LENGTH: 5
<212> TYPE: PRT
<213> ORGANISM: Vicugna pacos

<400> SEQUENCE: 4

Arg Tyr Val Met Gly
1               5


<210> SEQ ID NO 5
<211> LENGTH: 5
<212> TYPE: PRT
<213> ORGANISM: Vicugna pacos

<400> SEQUENCE: 5

Arg Tyr Ala Met Gly
1               5


<210> SEQ ID NO 6
<211> LENGTH: 5
<212> TYPE: PRT
```

<213> ORGANISM: Vicugna pacos

<400> SEQUENCE: 6

Tyr Tyr Ala Ile Gly
1               5

<210> SEQ ID NO 7
<211> LENGTH: 16
<212> TYPE: PRT
<213> ORGANISM: Vicugna pacos

<400> SEQUENCE: 7

Thr Val Asn Arg Ala Ser Arg Thr Ile Tyr Ala Asp Ser Val Arg Gly
1               5                   10                  15

<210> SEQ ID NO 8
<211> LENGTH: 17
<212> TYPE: PRT
<213> ORGANISM: Vicugna pacos

<400> SEQUENCE: 8

Ser Ile Ser Tyr Arg Gly Ile Thr Thr Tyr Tyr Ala Gln Pro Val Lys
1               5                   10                  15

Gly

<210> SEQ ID NO 9
<211> LENGTH: 16
<212> TYPE: PRT
<213> ORGANISM: Vicugna pacos

<400> SEQUENCE: 9

Ile Ile Asn Arg Ala Ser Trp Thr Arg Tyr Ala Asp Ser Val Lys Gly
1               5                   10                  15

<210> SEQ ID NO 10
<211> LENGTH: 17
<212> TYPE: PRT
<213> ORGANISM: Vicugna pacos

<400> SEQUENCE: 10

Ala Ile Ser Trp Ser Ala Gly Tyr Thr Phe Tyr Arg Asp Ser Val Lys
1               5                   10                  15

Gly

<210> SEQ ID NO 11
<211> LENGTH: 17
<212> TYPE: PRT
<213> ORGANISM: Vicugna pacos

<400> SEQUENCE: 11

Ala Ile Ser Trp Asn Gly Asp Asp Thr Phe Tyr Ala Asp Ser Val Lys
1               5                   10                  15

Gly

<210> SEQ ID NO 12
<211> LENGTH: 17
<212> TYPE: PRT
<213> ORGANISM: Vicugna pacos

<400> SEQUENCE: 12

Ala Ile Ser Trp Asn Gly Gly Ser Thr Tyr Tyr Ala Asp Ser Val Lys
1               5                   10                  15

Gly

<210> SEQ ID NO 13
<211> LENGTH: 14
<212> TYPE: PRT
<213> ORGANISM: Vicugna pacos

<400> SEQUENCE: 13

```
Ile Ala Thr Ser Ala Ser Gly Arg Gly Val Thr Ser Thr Ser
1               5                   10
```

<210> SEQ ID NO 14
<211> LENGTH: 8
<212> TYPE: PRT
<213> ORGANISM: Vicugna pacos

<400> SEQUENCE: 14

```
Lys Ser Ile Trp Gly Asn Ala Tyr
1               5
```

<210> SEQ ID NO 15
<211> LENGTH: 13
<212> TYPE: PRT
<213> ORGANISM: Vicugna pacos

<400> SEQUENCE: 15

```
Asp Glu Asn Gly Leu Gly Arg Lys Arg Gly Phe Gly Ser
1               5                   10
```

<210> SEQ ID NO 16
<211> LENGTH: 11
<212> TYPE: PRT
<213> ORGANISM: Vicugna pacos

<400> SEQUENCE: 16

```
Arg Asn Ser Tyr Ala Ala Phe Ala Arg Ala Tyr
1               5                   10
```

<210> SEQ ID NO 17
<211> LENGTH: 10
<212> TYPE: PRT
<213> ORGANISM: Vicugna pacos

<400> SEQUENCE: 17

```
Arg Pro Gln Phe Gly Leu Gly Tyr Asn Tyr
1               5                   10
```

<210> SEQ ID NO 18
<211> LENGTH: 30
<212> TYPE: PRT
<213> ORGANISM: Vicugna pacos

<400> SEQUENCE: 18

```
Gln Val Gln Leu Val Glu Ser Gly Gly Gly Val Val Gln Thr Gly Gly
1               5                   10                  15

Ser Leu Arg Leu Ser Cys Ala Ala Ser Gly Ser Thr Phe Ser
            20                  25                  30
```

<210> SEQ ID NO 19
<211> LENGTH: 30
<212> TYPE: PRT
<213> ORGANISM: Vicugna pacos

<400> SEQUENCE: 19

```
Gln Leu Gln Leu Val Glu Ser Gly Gly Gly Leu Val Gln Ala Gly Gly
1               5                   10                  15

Ser Leu Arg Leu Ser Cys Val Ala Ser Gly Phe Pro Phe Ala
            20                  25                  30


<210> SEQ ID NO 20
<211> LENGTH: 30
<212> TYPE: PRT
<213> ORGANISM: Vicugna pacos

<400> SEQUENCE: 20

Gln Leu Gln Leu Val Glu Pro Gly Gly Gly Val Val Gln Pro Gly Gly
1               5                   10                  15

Ser Leu Arg Leu Ser Cys Leu Ala Ser Gly Ser Asp Phe Ser
            20                  25                  30


<210> SEQ ID NO 21
<211> LENGTH: 30
<212> TYPE: PRT
<213> ORGANISM: Vicugna pacos

<400> SEQUENCE: 21

Glu Val Gln Leu Val Glu Ser Gly Gly Gly Leu Val Gln Ala Gly Gly
1               5                   10                  15

Ser Leu Arg Leu Ser Cys Ala Val Ser Gly Arg Thr Ser Ser
            20                  25                  30


<210> SEQ ID NO 22
<211> LENGTH: 30
<212> TYPE: PRT
<213> ORGANISM: Vicugna pacos

<400> SEQUENCE: 22

Glu Leu Gln Leu Val Glu Ser Gly Gly Gly Ala Val His Thr Gly Gly
1               5                   10                  15

Ser Leu Arg Leu Ser Cys Ala Val Ser Gly Arg Thr Asp Ile
            20                  25                  30


<210> SEQ ID NO 23
<211> LENGTH: 30
<212> TYPE: PRT
<213> ORGANISM: Vicugna pacos

<400> SEQUENCE: 23

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp
            20                  25                  30


<210> SEQ ID NO 24
<211> LENGTH: 14
<212> TYPE: PRT
<213> ORGANISM: Vicugna pacos

<400> SEQUENCE: 24

Trp Tyr Arg Gln Ala Pro Gly Lys Gln Arg Glu Leu Val Ala
1               5                   10


<210> SEQ ID NO 25
<211> LENGTH: 14
<212> TYPE: PRT
<213> ORGANISM: Vicugna pacos
```

```
<400> SEQUENCE: 25

Trp Phe Arg Gln Ala Pro Gly Lys Glu Arg Glu Phe Val Ala
1               5                   10


<210> SEQ ID NO 26
<211> LENGTH: 14
<212> TYPE: PRT
<213> ORGANISM: Vicugna pacos

<400> SEQUENCE: 26

Trp Val Arg Gln Ala Pro Gly Lys Glu Arg Glu Phe Leu Ala
1               5                   10


<210> SEQ ID NO 27
<211> LENGTH: 14
<212> TYPE: PRT
<213> ORGANISM: Vicugna pacos

<400> SEQUENCE: 27

Trp Phe Arg Gln Ala Pro Gly Arg Glu Arg Glu Phe Val Ala
1               5                   10


<210> SEQ ID NO 28
<211> LENGTH: 14
<212> TYPE: PRT
<213> ORGANISM: Vicugna pacos

<400> SEQUENCE: 28

Trp Phe Arg Gln Ala Pro Gly Asn Glu Arg Glu Phe Val Ala
1               5                   10


<210> SEQ ID NO 29
<211> LENGTH: 32
<212> TYPE: PRT
<213> ORGANISM: Vicugna pacos

<400> SEQUENCE: 29

Arg Phe Thr Ile Ser Arg Asp Asn Ala Lys Asn Leu Val Tyr Leu Gln
1               5                   10                  15

Met Asn Asn Leu Lys Pro Glu Asp Thr Ala Val Tyr Tyr Cys Asn Val
            20                  25                  30


<210> SEQ ID NO 30
<211> LENGTH: 32
<212> TYPE: PRT
<213> ORGANISM: Vicugna pacos

<400> SEQUENCE: 30

Arg Phe Thr Met Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Tyr Ala
            20                  25                  30


<210> SEQ ID NO 31
<211> LENGTH: 32
<212> TYPE: PRT
<213> ORGANISM: Vicugna pacos

<400> SEQUENCE: 31

Arg Phe Thr Ile Ser Arg Asp Asn Ser Lys Asn Leu Val Phe Leu Gln
1               5                   10                  15

Met Asn Asn Leu Lys Pro Asp Asp Thr Ala Val Tyr Tyr Cys Asn Ala
            20                  25                  30
```

<210> SEQ ID NO 32
<211> LENGTH: 32
<212> TYPE: PRT
<213> ORGANISM: Vicugna pacos

<400> SEQUENCE: 32

```
Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Asn Ala
            20                  25                  30
```

<210> SEQ ID NO 33
<211> LENGTH: 32
<212> TYPE: PRT
<213> ORGANISM: Vicugna pacos

<400> SEQUENCE: 33

```
Arg Phe Thr Ile Ser Arg Asp Asn Ala Lys Asn Ala Val Ser Leu Gln
1               5                   10                  15

Met Asp Ser Leu Arg Pro Glu Asp Thr Ala Val Tyr Tyr Cys Asn Ala
            20                  25                  30
```

<210> SEQ ID NO 34
<211> LENGTH: 32
<212> TYPE: PRT
<213> ORGANISM: Vicugna pacos

<400> SEQUENCE: 34

```
Arg Phe Thr Ile Ser Arg Asp Asn Ala Lys Glu Thr Val Tyr Leu Gln
1               5                   10                  15

Met Asn Ser Leu Lys Pro Glu Asp Thr Gly Val Tyr Tyr Cys Asn Tyr
            20                  25                  30
```

<210> SEQ ID NO 35
<211> LENGTH: 11
<212> TYPE: PRT
<213> ORGANISM: Vicugna pacos

<400> SEQUENCE: 35

```
Trp Gly Gln Gly Ser Gln Val Thr Val Ser Ser
1               5                   10
```

<210> SEQ ID NO 36
<211> LENGTH: 11
<212> TYPE: PRT
<213> ORGANISM: Vicugna pacos

<400> SEQUENCE: 36

```
Trp Gly Gln Gly Thr Gln Val Thr Val Ser Pro
1               5                   10
```

<210> SEQ ID NO 37
<211> LENGTH: 11
<212> TYPE: PRT
<213> ORGANISM: Vicugna pacos

<400> SEQUENCE: 37

```
Trp Gly Gln Gly Thr Gln Val Thr Val Ser Ser
1               5                   10
```

<210> SEQ ID NO 38
<211> LENGTH: 122

<212> TYPE: PRT
<213> ORGANISM: Vicugna pacos

<400> SEQUENCE: 38

```
Gln Val Gln Leu Val Glu Ser Gly Gly Gly Val Val Gln Thr Gly Gly
1               5                   10                  15

Ser Leu Arg Leu Ser Cys Ala Ala Ser Gly Ser Thr Phe Ser Ile Gly
            20                  25                  30

Ala Met Gly Trp Tyr Arg Gln Ala Pro Gly Lys Gln Arg Glu Leu Val
        35                  40                  45

Ala Thr Val Asn Arg Ala Ser Arg Thr Ile Tyr Ala Asp Ser Val Arg
    50                  55                  60

Gly Arg Phe Thr Ile Ser Arg Asp Asn Ala Lys Asn Leu Val Tyr Leu
65                  70                  75                  80

Gln Met Asn Asn Leu Lys Pro Glu Asp Thr Ala Val Tyr Tyr Cys Asn
                85                  90                  95

Val Ile Ala Thr Ser Ala Ser Gly Arg Gly Val Thr Ser Thr Ser Trp
            100                 105                 110

Gly Gln Gly Ser Gln Val Thr Val Ser Ser
        115                 120
```

<210> SEQ ID NO 39
<211> LENGTH: 117
<212> TYPE: PRT
<213> ORGANISM: Vicugna pacos

<400> SEQUENCE: 39

```
Gln Leu Gln Leu Val Glu Ser Gly Gly Gly Leu Val Gln Ala Gly Gly
1               5                   10                  15

Ser Leu Arg Leu Ser Cys Val Ala Ser Gly Phe Pro Phe Ala Ser Ser
            20                  25                  30

Ala Met Ala Trp Phe Arg Gln Ala Pro Gly Lys Glu Arg Glu Phe Val
        35                  40                  45

Ala Ser Ile Ser Tyr Arg Gly Ile Thr Thr Tyr Tyr Ala Gln Pro Val
    50                  55                  60

Lys Gly Arg Phe Thr Met Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Tyr Ala Lys Ser Ile Trp Gly Asn Ala Tyr Trp Gly Gln Gly Thr Gln
            100                 105                 110

Val Thr Val Ser Pro
        115
```

<210> SEQ ID NO 40
<211> LENGTH: 122
<212> TYPE: PRT
<213> ORGANISM: Vicugna pacos

<400> SEQUENCE: 40

```
Gln Leu Gln Leu Val Glu Pro Gly Gly Gly Val Val Gln Pro Gly Gly
1               5                   10                  15

Ser Leu Arg Leu Ser Cys Leu Ala Ser Gly Ser Asp Phe Ser Leu Gly
            20                  25                  30

Ala Met Gly Trp Tyr Arg Gln Ala Pro Gly Lys Gln Arg Glu Leu Val
        35                  40                  45

Ala Ile Ile Asn Arg Ala Ser Trp Thr Arg Tyr Ala Asp Ser Val Lys
```

```
    50                  55                  60

Gly Arg Phe Thr Ile Ser Arg Asp Asn Ser Lys Asn Leu Val Phe Leu
65                  70                  75                  80

Gln Met Asn Asn Leu Lys Pro Asp Asp Thr Ala Val Tyr Tyr Cys Asn
                85                  90                  95

Ala Ile Ala Thr Ser Ala Ser Gly Arg Gly Val Thr Ser Thr Ser Trp
            100                 105                 110

Gly Gln Gly Ser Gln Val Thr Val Ser Ser
        115                 120


<210> SEQ ID NO 41
<211> LENGTH: 122
<212> TYPE: PRT
<213> ORGANISM: Vicugna pacos

<400> SEQUENCE: 41

Glu Val Gln Leu Val Glu Ser Gly Gly Gly Leu Val Gln Ala Gly Gly
1               5                   10                  15

Ser Leu Arg Leu Ser Cys Ala Val Ser Gly Arg Thr Ser Ser Arg Tyr
            20                  25                  30

Val Met Gly Trp Val Arg Gln Ala Pro Gly Lys Glu Arg Glu Phe Leu
        35                  40                  45

Ala Ala Ile Ser Trp Ser Ala Gly Tyr Thr Phe Tyr Arg Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Asn Ala Asp Glu Asn Gly Leu Gly Arg Lys Arg Gly Phe Gly Ser Trp
            100                 105                 110

Gly Gln Gly Thr Gln Val Thr Val Ser Ser
        115                 120


<210> SEQ ID NO 42
<211> LENGTH: 120
<212> TYPE: PRT
<213> ORGANISM: Vicugna pacos

<400> SEQUENCE: 42

Glu Leu Gln Leu Val Glu Ser Gly Gly Gly Ala Val His Thr Gly Gly
1               5                   10                  15

Ser Leu Arg Leu Ser Cys Ala Val Ser Gly Arg Thr Asp Ile Arg Tyr
            20                  25                  30

Ala Met Gly Trp Phe Arg Gln Ala Pro Gly Arg Glu Arg Glu Phe Val
        35                  40                  45

Ala Ala Ile Ser Trp Asn Gly Asp Asp Thr Phe Tyr Ala Asp Ser Val
    50                  55                  60

Lys Gly Arg Phe Thr Ile Ser Arg Asp Asn Ala Lys Asn Ala Val Ser
65                  70                  75                  80

Leu Gln Met Asp Ser Leu Arg Pro Glu Asp Thr Ala Val Tyr Tyr Cys
                85                  90                  95

Asn Ala Arg Asn Ser Tyr Ala Ala Phe Ala Arg Ala Tyr Trp Gly Gln
            100                 105                 110

Gly Thr Gln Val Thr Val Ser Ser
        115                 120
```

```
<210> SEQ ID NO 43
<211> LENGTH: 119
<212> TYPE: PRT
<213> ORGANISM: Vicugna pacos

<400> SEQUENCE: 43

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Ala Ile Gly Trp Phe Arg Gln Ala Pro Gly Asn Glu Arg Glu Phe Val
        35                  40                  45

Ala Ala Ile Ser Trp Asn Gly Gly Ser Thr Tyr Tyr Ala Asp Ser Val
    50                  55                  60

Lys Gly Arg Phe Thr Ile Ser Arg Asp Asn Ala Lys Glu Thr Val Tyr
65                  70                  75                  80

Leu Gln Met Asn Ser Leu Lys Pro Glu Asp Thr Gly Val Tyr Tyr Cys
                85                  90                  95

Asn Tyr Arg Pro Gln Phe Gly Leu Gly Tyr Asn Tyr Trp Gly Gln Gly
            100                 105                 110

Thr Gln Val Thr Val Ser Ser
        115


<210> SEQ ID NO 44
<211> LENGTH: 118
<212> TYPE: PRT
<213> ORGANISM: Vicugna pacos

<400> SEQUENCE: 44

Gln Val Gln Leu Val Glu Ser Gly Gly Gly Leu Val Gln Ala Gly Lys
1               5                   10                  15

Ser Leu Arg Leu Ser Cys Thr Ala Ser Gly Ser Ile Pro Ser Ile Gly
            20                  25                  30

Val Met Gly Trp His Arg Gln Ala Pro Gly Lys Gln Arg Glu Leu Val
        35                  40                  45

Ala Thr Ile Ser Gln Gly Gly His Ile Asn Tyr Phe Glu Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Gly Val Tyr Tyr Cys Asn
                85                  90                  95

Ala Phe Trp Leu Pro Leu Arg Leu Asn Asp Tyr Trp Gly Gln Gly Thr
            100                 105                 110

Gln Val Thr Val Ser Ser
        115


<210> SEQ ID NO 45
<211> LENGTH: 255
<212> TYPE: PRT
<213> ORGANISM: Artificial Sequence
<220> FEATURE:
<223> OTHER INFORMATION: Protein-binding antibody

<400> SEQUENCE: 45

Gln Val Gln Leu Val Glu Ser Gly Gly Gly Val Val Gln Thr Gly Gly
1               5                   10                  15

Ser Leu Arg Leu Ser Cys Ala Ala Ser Gly Ser Thr Phe Ser Ile Gly
            20                  25                  30
```

```
Ala Met Gly Trp Tyr Arg Gln Ala Pro Gly Lys Gln Arg Glu Leu Val
        35                  40                  45

Ala Thr Val Asn Arg Ala Ser Arg Thr Ile Tyr Ala Asp Ser Val Arg
    50                  55                  60

Gly Arg Phe Thr Ile Ser Arg Asp Asn Ala Lys Asn Leu Val Tyr Leu
65                  70                  75                  80

Gln Met Asn Asn Leu Lys Pro Glu Asp Thr Ala Val Tyr Tyr Cys Asn
                85                  90                  95

Val Ile Ala Thr Ser Ala Ser Gly Arg Gly Val Thr Ser Thr Ser Trp
            100                 105                 110

Gly Gln Gly Ser Gln Val Thr Val Ser Ser Gly Gly Gly Gly Ser Gly
        115                 120                 125

Gly Gly Ala Ser Gly Gly Gly Gly Ser Gln Val Gln Leu Val Glu Ser
    130                 135                 140

Gly Gly Gly Leu Val Gln Ala Gly Lys Ser Leu Arg Leu Ser Cys Thr
145                 150                 155                 160

Ala Ser Gly Ser Ile Pro Ser Ile Gly Val Met Gly Trp His Arg Gln
                165                 170                 175

Ala Pro Gly Lys Gln Arg Glu Leu Val Ala Thr Ile Ser Gln Gly Gly
            180                 185                 190

His Ile Asn Tyr Phe Glu Ser Val Lys Gly Arg Phe Thr Ile Ser Arg
        195                 200                 205

Asp Asn Ala Lys Asn Thr Val Tyr Leu Gln Met Asn Ser Leu Lys Pro
    210                 215                 220

Glu Asp Thr Gly Val Tyr Tyr Cys Asn Ala Phe Trp Leu Pro Leu Arg
225                 230                 235                 240

Leu Asn Asp Tyr Trp Gly Gln Gly Thr Gln Val Thr Val Ser Ser
                245                 250                 255


<210> SEQ ID NO 46
<211> LENGTH: 255
<212> TYPE: PRT
<213> ORGANISM: Artificial Sequence
<220> FEATURE:
<223> OTHER INFORMATION: Protein-binding antibody

<400> SEQUENCE: 46

Gln Val Gln Leu Val Glu Ser Gly Gly Gly Leu Val Gln Ala Gly Lys
1               5                   10                  15

Ser Leu Arg Leu Ser Cys Thr Ala Ser Gly Ser Ile Pro Ser Ile Gly
            20                  25                  30

Val Met Gly Trp His Arg Gln Ala Pro Gly Lys Gln Arg Glu Leu Val
        35                  40                  45

Ala Thr Ile Ser Gln Gly Gly His Ile Asn Tyr Phe Glu Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Gly Val Tyr Tyr Cys Asn
                85                  90                  95

Ala Phe Trp Leu Pro Leu Arg Leu Asn Asp Tyr Trp Gly Gln Gly Thr
            100                 105                 110

Gln Val Thr Val Ser Ser Gly Gly Gly Gly Ser Gly Gly Gly Ala Ser
        115                 120                 125

Gly Gly Gly Gly Ser Gln Val Gln Leu Val Glu Ser Gly Gly Gly Val
    130                 135                 140
```

```
Val Gln Thr Gly Gly Ser Leu Arg Leu Ser Cys Ala Ala Ser Gly Ser
145                 150                 155                 160

Thr Phe Ser Ile Gly Ala Met Gly Trp Tyr Arg Gln Ala Pro Gly Lys
                165                 170                 175

Gln Arg Glu Leu Val Ala Thr Val Asn Arg Ala Ser Arg Thr Ile Tyr
            180                 185                 190

Ala Asp Ser Val Arg Gly Arg Phe Thr Ile Ser Arg Asp Asn Ala Lys
        195                 200                 205

Asn Leu Val Tyr Leu Gln Met Asn Asn Leu Lys Pro Glu Asp Thr Ala
    210                 215                 220

Val Tyr Tyr Cys Asn Val Ile Ala Thr Ser Ala Ser Gly Arg Gly Val
225                 230                 235                 240

Thr Ser Thr Ser Trp Gly Gln Gly Ser Gln Val Thr Val Ser Ser
                245                 250                 255


<210> SEQ ID NO 47
<211> LENGTH: 250
<212> TYPE: PRT
<213> ORGANISM: Artificial Sequence
<220> FEATURE:
<223> OTHER INFORMATION: Protein-binding antibody

<400> SEQUENCE: 47

Gln Val Gln Leu Val Glu Ser Gly Gly Gly Leu Val Gln Ala Gly Lys
1               5                   10                  15

Ser Leu Arg Leu Ser Cys Thr Ala Ser Gly Ser Ile Pro Ser Ile Gly
            20                  25                  30

Val Met Gly Trp His Arg Gln Ala Pro Gly Lys Gln Arg Glu Leu Val
        35                  40                  45

Ala Thr Ile Ser Gln Gly Gly His Ile Asn Tyr Phe Glu Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Gly Val Tyr Tyr Cys Asn
                85                  90                  95

Ala Phe Trp Leu Pro Leu Arg Leu Asn Asp Tyr Trp Gly Gln Gly Thr
            100                 105                 110

Gln Val Thr Val Ser Ser Gly Gly Gly Gly Ser Gly Gly Gly Ala Ser
        115                 120                 125

Gly Gly Gly Gly Ser Gln Leu Gln Leu Val Glu Ser Gly Gly Gly Leu
    130                 135                 140

Val Gln Ala Gly Gly Ser Leu Arg Leu Ser Cys Val Ala Ser Gly Phe
145                 150                 155                 160

Pro Phe Ala Ser Ser Ala Met Ala Trp Phe Arg Gln Ala Pro Gly Lys
                165                 170                 175

Glu Arg Glu Phe Val Ala Ser Ile Ser Tyr Arg Gly Ile Thr Thr Tyr
            180                 185                 190

Tyr Ala Gln Pro Val Lys Gly Arg Phe Thr Met Ser Arg Asp Asn Ala
        195                 200                 205

Lys Asn Thr Val Tyr Leu Gln Met Asn Ser Leu Lys Pro Glu Asp Thr
    210                 215                 220

Ala Val Tyr Tyr Cys Tyr Ala Lys Ser Ile Trp Gly Asn Ala Tyr Trp
225                 230                 235                 240

Gly Gln Gly Thr Gln Val Thr Val Ser Pro
                245                 250
```

<210> SEQ ID NO 48
<211> LENGTH: 540
<212> TYPE: PRT
<213> ORGANISM: Vicugna pacos

<400> SEQUENCE: 48

```
Met Lys Met Ala Ser Asn Asp Ala Asn Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser Arg Asn Tyr Thr Met Asn Leu Ala
    290                 295                 300

Ser Gln Asn Trp Asn Ser Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Thr Asp Gly Ser Thr Arg Gly His Lys Ala Thr Val Tyr
            340                 345                 350

Thr Gly Ser Ala Asp Phe Ser Pro Lys Leu Gly Arg Val Gln Phe Ala
        355                 360                 365

Thr Asp Thr Asp Asn Asp Phe Glu Thr Asn Gln Asn Thr Lys Phe Thr
    370                 375                 380
```

```
Pro Val Gly Val Ile Gln Asp Gly Gly Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Leu
    530                 535                 540


<210> SEQ ID NO 49
<211> LENGTH: 15
<212> TYPE: DNA
<213> ORGANISM: Artificial Sequence
<220> FEATURE:
<223> OTHER INFORMATION: Primer

<400> SEQUENCE: 49

ggtggtcctg gctgc                                                        15


<210> SEQ ID NO 50
<211> LENGTH: 49
<212> TYPE: DNA
<213> ORGANISM: Artificial Sequence
<220> FEATURE:
<223> OTHER INFORMATION: Primer

<400> SEQUENCE: 50

ctgctcctcg cggcccagcc ggccatggct sagktgcagc tcgtggagt                   49


<210> SEQ ID NO 51
<211> LENGTH: 21
<212> TYPE: DNA
<213> ORGANISM: Artificial Sequence
<220> FEATURE:
<223> OTHER INFORMATION: Primer

<400> SEQUENCE: 51

tggggtcttc gctgtggtgc g                                                 21


<210> SEQ ID NO 52
<211> LENGTH: 21
<212> TYPE: DNA
<213> ORGANISM: Artificial Sequence
<220> FEATURE:
<223> OTHER INFORMATION: Primer

<400> SEQUENCE: 52

ttgtggtttt ggtgtcttgg g                                                 21
```

<210> SEQ ID NO 53
<211> LENGTH: 45
<212> TYPE: DNA
<213> ORGANISM: Artificial Sequence
<220> FEATURE:
<223> OTHER INFORMATION: Primer

<400> SEQUENCE: 53
tttgctctgc ggccgcagag gccgtggggt cttcgctgtg gtgcg 45

<210> SEQ ID NO 54
<211> LENGTH: 46
<212> TYPE: DNA
<213> ORGANISM: Artificial Sequence
<220> FEATURE:
<223> OTHER INFORMATION: Primer

<400> SEQUENCE: 54
tttgctctgc ggccgcagag gccgattgtg gttttggtgt cttggg 46

<210> SEQ ID NO 55
<211> LENGTH: 13
<212> TYPE: DNA
<213> ORGANISM: Artificial Sequence
<220> FEATURE:
<223> OTHER INFORMATION: SfiI(a) site

<400> SEQUENCE: 55
ggcccagccg gcc 13

<210> SEQ ID NO 56
<211> LENGTH: 13
<212> TYPE: DNA
<213> ORGANISM: Artificial Sequence
<220> FEATURE:
<223> OTHER INFORMATION: SfiI(b) site

<400> SEQUENCE: 56
ggcctctgcg gcc 13

<210> SEQ ID NO 57
<211> LENGTH: 4057
<212> TYPE: DNA
<213> ORGANISM: Artificial Sequence
<220> FEATURE:
<223> OTHER INFORMATION: Plasmid Vector 1

<400> SEQUENCE: 57
gacgaaaggg cctcgtgata cgcctatttt tataggttaa tgtcatgata ataatggttt 60
cttagacgtc aggtggcact tttcggggaa atgtgcgcgg aacccctatt tgtttatttt 120
tctaaataca ttcaaatatg tatccgctca tgagacaata accctgataa atgcttcaat 180
aatattgaaa aaggaagagt atgagtattc aacatttccg tgtcgccctt attccctttt 240
ttgcggcatt ttgccttcct gtttttgctc acccagaaac gctggtgaaa gtaaaagatg 300
ctgaagatca gttgggtgca cgagtgggtt acatcgaact ggatctcaac agcggtaaga 360
tccttgagag ttttcgcccc gaagaacgtt ttccaatgat gagcactttt aaagttctgc 420
tatgtggcgc ggtattatcc cgtattgacg ccgggcaaga gcaactcggt cgccgcatac 480
actattctca gaatgacttg gttgagtact caccagtcac agaaaagcat cttacggatg 540
gcatgacagt aagagaatta tgcagtgctg ccataaccat gagtgataac actgcggcca 600
acttacttct gacaacgatc ggaggaccga aggagctaac cgcttttttg cacaacatgg 660

-continued

```
gggatcatgt aactcgcctt gatcgttggg aaccggagct gaatgaagcc ataccaaacg    720
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc atttttaatt taaaaggatc taggtgaaga   1140
tcctttttga taatctcatg accaaaatcc cttaacgtga gttttcgttc cactgagcgt   1200
cagaccccgt agaaaagatc aaaggatctt cttgagatcc tttttttctg cgcgtaatct   1260
gctgcttgca aacaaaaaaa ccaccgctac cagcggtggt ttgtttgccg gatcaagagc   1320
taccaactct ttttccgaag gtaactggct tcagcagagc gcagatacca aatactgtcc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga acggggggtt   1560
cgtgcacaca gcccagcttg gagcgaacga cctacaccga actgagatac ctacagcgtg   1620
agctatgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg atttttgtga tgctcgtcag   1800
gggggcggag cctatggaaa aacgccagca acgcggcctt tttacggttc ctggcctttt   1860
gctggccttt tgctcacatg ttctttcctg cgttatcccc tgattctgtg gataaccgta   1920
ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
accatgatta cgccaagctt cgaaggagac agtcataatg aaatacctgc tgccgaccgc   2280
tgctgctggt ctgctgctcc tcgcggccca gccggccatg gagctcaaga tgacacagac   2340
tacatcctcc ctgtcagcct ctctgggaga cagagtcacc atcagttgca gggcaagtca   2400
ggacattagc gattatttaa actggtatca gcagaaacca gatggaactg ttaaactcct   2460
gatctattac acatcaagtt tacactcagg agtcccatca aggttcagtg gcggtgggtc   2520
tggaacagat tattctctca ccattagcaa cctggagcaa gaagatattg ccacttactt   2580
ttgccaacag ggtaatacgc ttccgtggac gtttggtgga ggcaccaagc tggaaatcaa   2640
acgggctgat gctgcaccaa ctgtaggcct ctgcggccgc agagcaaaaa ctcatctcag   2700
aagaggatct gaatggggcc gcatagggtt ccggtgattt tgattatgaa aagatggcaa   2760
acgctaataa gggggctatg accgaaaatg ccgatgaaaa cgcgctacag tctgacgcta   2820
aaggcaaact tgattctgtc gctactgatt acggtgctgc tatcgatggt ttcattggtg   2880
acgtttccgg ccttgctaat ggtaatggtg ctactggtga ttttgctggc tctaattccc   2940
aaatggctca agtcggtgac ggtgataatt cacctttaat gaataatttc cgtcaatatt   3000
```

taccttccct ccctcaatcg gttgaatgtc gccctttgt ctttagcgct ggtaaaccat 3060
atgaattttc tattgattgt gacaaaataa acttattccg tggtgtcttt gcgtttcttt 3120
tatatgttgc cacctttatg tatgtatttt ctacgtttgc taacatactg cgtaataagg 3180
agtcttaata agaattcact ggccgtcgtt ttacaacgtc gtgactggga aaaccctggc 3240
gttacccaac ttaatcgcct tgcagcacat ccccctttcg ccagctggcg taatagcgaa 3300
gaggcccgca ccgatcgccc ttcccaacag ttgcgcagcc tgaatggcga atggcgcctg 3360
atgcggtatt ttctccttac gcatctgtgc ggtatttcac accgcatatg aaaattgtaa 3420
gcgttaatat tttgttaaaa ttcgcgttaa atttttgtta aatcagctca ttttttaacc 3480
aataggccga aatcggcaaa atcccttata aatcaaaaga atagaccgag atagggttga 3540
gtgttgttcc agtttggaac aagagtccac tattaaagaa cgtggactcc aacgtcaaag 3600
ggcgaaaaac cgtctatcag ggcgatggcc cactacgtga accatcaccc taatcaagtt 3660
ttttggggtc gaggtgccgt aaagcactaa atcggaaccc taaagggagc ccccgattta 3720
gagcttgacg gggaaagccg gcgaacgtgg cgagaaagga agggaagaaa gcgaaaggag 3780
cgggcgctag ggcgctggca agtgtagcgg tcacgctgcg cgtaaccacc acacccgccg 3840
cgcttaatgc gccgctacag ggcgcgtccc atatggtgca ctctcagtac aatctgctct 3900
gatgccgcat agttaagcca gccccgacac ccgccaacac ccgctgacgc gccctgacgg 3960
gcttgtctgc tcccggcatc cgcttacaga caagctgtga ccgtctccgg gagctgcatg 4020
tgtcagaggt tttcaccgtc atcaccgaaa cgcgcga 4057

<210> SEQ ID NO 58
<211> LENGTH: 405
<212> TYPE: DNA
<213> ORGANISM: Artificial Sequence
<220> FEATURE:
<223> OTHER INFORMATION: DNA coding for anti-Norovirus VHH antibody

<400> SEQUENCE: 58
caggtgcagc tcgtggagtc tgggggaggt gtggtgcaga ctggggggtc tctgagactt 60
tcctgtgcag cctctggaag tactttcagt atcggtgcca tgggctggta ccgccaggcg 120
ccagggaagc agcgcgagtt ggtcgccact gttaatcggg cttctcggac aatctatgca 180
gactccgtga ggggccgatt caccatctcc agagacaatg ccaagaattt ggtgtatctg 240
caaatgaaca acctgaaacc tgaggacaca gccgtctatt attgtaatgt aatagcgacc 300
agcgcgtcgg ggcgcggggt cacgtcgact tcgtggggcc aggggtctca ggtcaccgtc 360
tcctcggaac ccaagacacc aaaaccacaa tcggcctctg cggcc 405

<210> SEQ ID NO 59
<211> LENGTH: 390
<212> TYPE: DNA
<213> ORGANISM: Artificial Sequence
<220> FEATURE:
<223> OTHER INFORMATION: DNA coding for anti-Norovirus VHH antibody

<400> SEQUENCE: 59
cagttgcagc tcgtggagtc tgggggaggc ttggtgcagg ctggggggtc tctgagactc 60
tcctgtgtag cctctggatt cccgttcgct agtagtgcca tggcgtggtt ccgccaggct 120
ccaggaaagg agcgtgagtt tgtagcgtcg ataagctacc gtggtattac cacatattat 180
gcgcaacccg tgaagggccg attcaccatg tccagagaca atgccaagaa cacggtgtat 240
ctgcaaatga acagcctgaa acctgaggac acggccgtgt attactgcta cgcaaaatct 300
atctggggta atgcctactg gggccagggg acccaggtca ccgtctcgcc agaacccaag 360
acaccaaaac cacaatcggc ctctgcggcc 390

<210> SEQ ID NO 60
<211> LENGTH: 405
<212> TYPE: DNA
<213> ORGANISM: Artificial Sequence
<220> FEATURE:
<223> OTHER INFORMATION: DNA coding for anti-Norovirus VHH antibody

<400> SEQUENCE: 60
cagttgcagc tcgtggagcc tgggggaggt gtggtgcagc cggggggggtc tctgagactt 60 tcctgtttag cctctggaag cgacttcagt ctcggtgcca tgggctggta tcgccaggcg 120
ccagggaaac agcgcgagct ggtcgccatt attaatcggg cttcttggac acgttatgca 180
gactccgtga agggccgctt caccatctcc agagacaatt ccaagaactt ggtgtttctg 240
caaatgaaca acctgaaacc tgacgacaca gccgtctatt actgtaatgc aatagcgacc 300
agcgcgtcgg ggcgcggggt cacgtcgact tcgtggggcc aggggtctca ggtcaccgtc 360
tcctcggaac ccaagacacc aaaaccacaa tcggcctctg cggcc 405

<210> SEQ ID NO 61
<211> LENGTH: 411
<212> TYPE: DNA
<213> ORGANISM: Artificial Sequence
<220> FEATURE:
<223> OTHER INFORMATION: DNA coding for anti-Norovirus VHH antibody

<400> SEQUENCE: 61
atggctgagg tgcagctcgt ggagtctggg ggaggattgg tgcaggctgg gggctctctg 60
agactctcct gcgcagtctc tggacgcacc tccagtcgtt atgtcatggg ctgggtccgc 120
caggctcccg ggaaggagcg tgagtttctg gcagctatta gctggagtgc tggctacaca 180
ttctatcgag actccgtgaa gggccgattc accatctccc gagacaacgc caagaacacg 240
gtgtatctgc aaatgaacag cctgaaacct gaggacacgg ccgtatatta ctgcaatgca 300
gatgagaacg ggttgggccg gaagaggggc tttggttcct ggggccaggg gacccaggtc 360
accgtctcct cggaacccaa gacaccaaaa ccacaatcgg cctctgcggc c 411

<210> SEQ ID NO 62
<211> LENGTH: 405
<212> TYPE: DNA
<213> ORGANISM: Artificial Sequence
<220> FEATURE:
<223> OTHER INFORMATION: DNA coding for anti-Norovirus VHH antibody

<400> SEQUENCE: 62
atggctgagt tgcagctcgt ggagtctggg ggaggagcgg tgcacactgg gggctctctg 60
aggctctcct gtgcagtatc gggacgcacc gatattcgct atgccatggg ctggttccgc 120
caggctccag ggagggagcg tgagtttgta gccgctatta gctggaatgg tgatgataca 180
ttttatgcgg attccgtgaa gggccgattc accatctcca gggacaacgc caagaacgcg 240
gtgtctctac aaatggacag cctgagacct gaggacacgg ccgtctatta ctgcaatgcg 300
cgcaacagct acgccgcctt cgcgcgtgcc tactggggcc aggggaccca ggtcaccgtc 360
tcctcagaac ccaagacacc aaaaccacaa tcggcctctg cggcc 405

<210> SEQ ID NO 63

<211> LENGTH: 402
<212> TYPE: DNA
<213> ORGANISM: Artificial Sequence
<220> FEATURE:
<223> OTHER INFORMATION: DNA coding for anti-Norovirus VHH antibody

<400> SEQUENCE: 63

```
atggctcagt tgcagctcgt ggagtctggg ggaggcttgg tgcagcctgg ggggtctctg     60

agactctcct gtgcagcctc tggattcact ttggattatt atgccatagg ctggttccgc    120

caggctccag ggaacgagcg tgagtttgta gcagctatta gctggaatgg tggtagcaca    180

tactatgcag actccgtgaa gggccgattc accatttcca gagacaacgc caaggagaca    240

gtatatctgc aaatgaacag cctgaagcct gaggacacag gtgtctatta ctgtaattat    300

agaccacaat ttggcctggg atataactat tggggccagg ggacccaggt caccgtctcc    360

tcagaaccca agacaccaaa accacaatcg gcctctgcgg cc                       402
```

<210> SEQ ID NO 64
<211> LENGTH: 366
<212> TYPE: DNA
<213> ORGANISM: Artificial Sequence
<220> FEATURE:
<223> OTHER INFORMATION: DNA coding for anti-Norovirus VHH antibody

<400> SEQUENCE: 64

```
caggtgcagc tcgtggagtc tggggggaggt gtggtgcaga ctggggggtc tctgagactt     60

tcctgtgcag cctctggaag tactttcagt atcggtgcca tgggctggta ccgccaggcg    120

ccagggaagc agcgcgagtt ggtcgccact gttaatcggg cttctcggac aatctatgca    180

gactccgtga ggggccgatt caccatctcc agagacaatg ccaagaattt ggtgtatctg    240

caaatgaaca acctgaaacc tgaggacaca gccgtctatt attgtaatgt aatagcgacc    300

agcgcgtcgg ggcgcggggt cacgtcgact tcgtggggcc aggggtctca ggtcactgtc    360

tcctca                                                               366
```

<210> SEQ ID NO 65
<211> LENGTH: 393
<212> TYPE: DNA
<213> ORGANISM: Artificial Sequence
<220> FEATURE:
<223> OTHER INFORMATION: DNA coding for anti-HSA VHH antibody

<400> SEQUENCE: 65

```
caggtgcagc tcgtggagtc tgggggaggc ttggtgcagg ctggtaagtc tctgagactc     60

tcctgtacag cgtctggaag catccccagt atcggtgtca tgggctggca ccgccaggct    120

ccagggaagc agcgcgagtt ggtcgcgact atttcgcagg gtggtcacat aaactatttt    180

gagtccgtga agggccgatt caccatctcc agagacaacg ccaagaacac ggtgtatctg    240

caaatgaaca gcctgaaacc tgaggacaca ggcgtctatt actgtaatgc gttttggctt    300

ccattgcgcc tgaatgacta ctggggccag gggacccagg tcaccgtctc ctcagaaccc    360

aagacaccaa aaccacaatc ggcctctgcg gcc                                 393
```

<210> SEQ ID NO 66
<211> LENGTH: 135
<212> TYPE: PRT
<213> ORGANISM: Vicugna pacos

<400> SEQUENCE: 66

```
Gln Val Gln Leu Val Glu Ser Gly Gly Gly Val Val Gln Thr Gly Gly
```

```
1               5                   10                  15

Ser Leu Arg Leu Ser Cys Ala Ala Ser Gly Ser Thr Phe Ser Ile Gly
            20                  25                  30

Ala Met Gly Trp Tyr Arg Gln Ala Pro Gly Lys Gln Arg Glu Leu Val
        35                  40                  45

Ala Thr Val Asn Arg Ala Ser Arg Thr Ile Tyr Ala Asp Ser Val Arg
    50                  55                  60

Gly Arg Phe Thr Ile Ser Arg Asp Asn Ala Lys Asn Leu Val Tyr Leu
65                  70                  75                  80

Gln Met Asn Asn Leu Lys Pro Glu Asp Thr Ala Val Tyr Tyr Cys Asn
                85                  90                  95

Val Ile Ala Thr Ser Ala Ser Gly Arg Gly Val Thr Ser Thr Ser Trp
            100                 105                 110

Gly Gln Gly Ser Gln Val Thr Val Ser Ser Glu Pro Lys Thr Pro Lys
        115                 120                 125

Pro Gln Ser Ala Ser Ala Ala
    130                 135


<210> SEQ ID NO 67
<211> LENGTH: 130
<212> TYPE: PRT
<213> ORGANISM: Vicugna pacos

<400> SEQUENCE: 67

Gln Leu Gln Leu Val Glu Ser Gly Gly Gly Leu Val Gln Ala Gly Gly
1               5                   10                  15

Ser Leu Arg Leu Ser Cys Val Ala Ser Gly Phe Pro Phe Ala Ser Ser
            20                  25                  30

Ala Met Ala Trp Phe Arg Gln Ala Pro Gly Lys Glu Arg Glu Phe Val
        35                  40                  45

Ala Ser Ile Ser Tyr Arg Gly Ile Thr Thr Tyr Tyr Ala Gln Pro Val
    50                  55                  60

Lys Gly Arg Phe Thr Met Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Tyr Ala Lys Ser Ile Trp Gly Asn Ala Tyr Trp Gly Gln Gly Thr Gln
            100                 105                 110

Val Thr Val Ser Pro Glu Pro Lys Thr Pro Lys Pro Gln Ser Ala Ser
        115                 120                 125

Ala Ala
    130


<210> SEQ ID NO 68
<211> LENGTH: 135
<212> TYPE: PRT
<213> ORGANISM: Vicugna pacos

<400> SEQUENCE: 68

Gln Leu Gln Leu Val Glu Pro Gly Gly Gly Val Val Gln Pro Gly Gly
1               5                   10                  15

Ser Leu Arg Leu Ser Cys Leu Ala Ser Gly Ser Asp Phe Ser Leu Gly
            20                  25                  30

Ala Met Gly Trp Tyr Arg Gln Ala Pro Gly Lys Gln Arg Glu Leu Val
        35                  40                  45

Ala Ile Ile Asn Arg Ala Ser Trp Thr Arg Tyr Ala Asp Ser Val Lys
```

```
    50                  55                  60

Gly Arg Phe Thr Ile Ser Arg Asp Asn Ser Lys Asn Leu Val Phe Leu
65                  70                  75                  80

Gln Met Asn Asn Leu Lys Pro Asp Asp Thr Ala Val Tyr Tyr Cys Asn
                85                  90                  95

Ala Ile Ala Thr Ser Ala Ser Gly Arg Gly Val Thr Ser Thr Ser Trp
            100                 105                 110

Gly Gln Gly Ser Gln Val Thr Val Ser Ser Glu Pro Lys Thr Pro Lys
        115                 120                 125

Pro Gln Ser Ala Ser Ala Ala
    130                 135


<210> SEQ ID NO 69
<211> LENGTH: 135
<212> TYPE: PRT
<213> ORGANISM: Vicugna pacos

<400> SEQUENCE: 69

Glu Val Gln Leu Val Glu Ser Gly Gly Gly Leu Val Gln Ala Gly Gly
1               5                   10                  15

Ser Leu Arg Leu Ser Cys Ala Val Ser Gly Arg Thr Ser Ser Arg Tyr
            20                  25                  30

Val Met Gly Trp Val Arg Gln Ala Pro Gly Lys Glu Arg Glu Phe Leu
        35                  40                  45

Ala Ala Ile Ser Trp Ser Ala Gly Tyr Thr Phe Tyr Arg Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Asn Ala Asp Glu Asn Gly Leu Gly Arg Lys Arg Gly Phe Gly Ser Trp
            100                 105                 110

Gly Gln Gly Thr Gln Val Thr Val Ser Ser Glu Pro Lys Thr Pro Lys
        115                 120                 125

Pro Gln Ser Ala Ser Ala Ala
    130                 135


<210> SEQ ID NO 70
<211> LENGTH: 133
<212> TYPE: PRT
<213> ORGANISM: Vicugna pacos

<400> SEQUENCE: 70

Glu Leu Gln Leu Val Glu Ser Gly Gly Gly Ala Val His Thr Gly Gly
1               5                   10                  15

Ser Leu Arg Leu Ser Cys Ala Val Ser Gly Arg Thr Asp Ile Arg Tyr
            20                  25                  30

Ala Met Gly Trp Phe Arg Gln Ala Pro Gly Arg Glu Arg Glu Phe Val
        35                  40                  45

Ala Ala Ile Ser Trp Asn Gly Asp Asp Thr Phe Tyr Ala Asp Ser Val
    50                  55                  60

Lys Gly Arg Phe Thr Ile Ser Arg Asp Asn Ala Lys Asn Ala Val Ser
65                  70                  75                  80

Leu Gln Met Asp Ser Leu Arg Pro Glu Asp Thr Ala Val Tyr Tyr Cys
                85                  90                  95

Asn Ala Arg Asn Ser Tyr Ala Ala Phe Ala Arg Ala Tyr Trp Gly Gln
```

```
            100                 105                 110

Gly Thr Gln Val Thr Val Ser Ser Glu Pro Lys Thr Pro Lys Pro Gln
        115                 120                 125

Ser Ala Ser Ala Ala
    130


<210> SEQ ID NO 71
<211> LENGTH: 132
<212> TYPE: PRT
<213> ORGANISM: Vicugna pacos

<400> SEQUENCE: 71

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Ala Ile Gly Trp Phe Arg Gln Ala Pro Gly Asn Glu Arg Glu Phe Val
        35                  40                  45

Ala Ala Ile Ser Trp Asn Gly Gly Ser Thr Tyr Tyr Ala Asp Ser Val
    50                  55                  60

Lys Gly Arg Phe Thr Ile Ser Arg Asp Asn Ala Lys Glu Thr Val Tyr
65                  70                  75                  80

Leu Gln Met Asn Ser Leu Lys Pro Glu Asp Thr Gly Val Tyr Tyr Cys
                85                  90                  95

Asn Tyr Arg Pro Gln Phe Gly Leu Gly Tyr Asn Tyr Trp Gly Gln Gly
            100                 105                 110

Thr Gln Val Thr Val Ser Ser Glu Pro Lys Thr Pro Lys Pro Gln Ser
        115                 120                 125

Ala Ser Ala Ala
    130


<210> SEQ ID NO 72
<211> LENGTH: 131
<212> TYPE: PRT
<213> ORGANISM: Vicugna pacos

<400> SEQUENCE: 72

Gln Val Gln Leu Val Glu Ser Gly Gly Gly Leu Val Gln Ala Gly Lys
1               5                   10                  15

Ser Leu Arg Leu Ser Cys Thr Ala Ser Gly Ser Ile Pro Ser Ile Gly
            20                  25                  30

Val Met Gly Trp His Arg Gln Ala Pro Gly Lys Gln Arg Glu Leu Val
        35                  40                  45

Ala Thr Ile Ser Gln Gly Gly His Ile Asn Tyr Phe Glu Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Gly Val Tyr Tyr Cys Asn
                85                  90                  95

Ala Phe Trp Leu Pro Leu Arg Leu Asn Asp Tyr Trp Gly Gln Gly Thr
            100                 105                 110

Gln Val Thr Val Ser Ser Glu Pro Lys Thr Pro Lys Pro Gln Ser Ala
        115                 120                 125

Ser Ala Ala
    130
```

```
<210> SEQ ID NO 73
<211> LENGTH: 30
<212> TYPE: DNA
<213> ORGANISM: Artificial Sequence
<220> FEATURE:
<223> OTHER INFORMATION: Primer

<400> SEQUENCE: 73

gccggctggg ccgcgaggag cagcagacca                                    30


<210> SEQ ID NO 74
<211> LENGTH: 30
<212> TYPE: DNA
<213> ORGANISM: Artificial Sequence
<220> FEATURE:
<223> OTHER INFORMATION: Primer

<400> SEQUENCE: 74

gcccagccgg ccatggccat ggatatcgga                                    30


<210> SEQ ID NO 75
<211> LENGTH: 96
<212> TYPE: DNA
<213> ORGANISM: Artificial Sequence
<220> FEATURE:
<223> OTHER INFORMATION: Primer

<400> SEQUENCE: 75

catggatatc ggaattaatt cggatccgac tacaaagacc atgacggtga ttataaagat     60

catgacatcc tcgagcacca ccaccaccac cactga                              96


<210> SEQ ID NO 76
<211> LENGTH: 96
<212> TYPE: DNA
<213> ORGANISM: Artificial Sequence
<220> FEATURE:
<223> OTHER INFORMATION: Primer

<400> SEQUENCE: 76

tcagtggtgg tggtggtggt gctcgaggat gtcatgatct ttataatcac cgtcatggtc     60

tttgtagtcg gatccgaatt aattccgata tccatg                              96


<210> SEQ ID NO 77
<211> LENGTH: 74
<212> TYPE: DNA
<213> ORGANISM: Artificial Sequence
<220> FEATURE:
<223> OTHER INFORMATION: Primer

<400> SEQUENCE: 77

aaatacctgc tgccgccatg gatatcggaa ttaattcggc ctctgcggcc gcaggatccg     60

actacaaaga ccat                                                      74


<210> SEQ ID NO 78
<211> LENGTH: 74
<212> TYPE: DNA
<213> ORGANISM: Artificial Sequence
<220> FEATURE:
<223> OTHER INFORMATION: Primer

<400> SEQUENCE: 78

atggtctttg tagtcggatc ctgcggccgc agaggccgaa ttaattccga tatccatggc     60

ggcagcaggt attt                                                      74
```

<210> SEQ ID NO 79
<211> LENGTH: 424
<212> TYPE: DNA
<213> ORGANISM: Artificial Sequence
<220> FEATURE:
<223> OTHER INFORMATION: DNA including the gene sequence coding for VHH antibody fragment

<400> SEQUENCE: 79

```
ggcccagccg gccatggctc aggtgcagct cgtggagtct gggggaggtg tggtgcagac     60

tggggggtct ctgagacttt cctgtgcagc ctctggaagt actttcagta tcggtgccat    120

gggctggtac cgccaggcgc cagggaagca gcgcgagttg gtcgccactg ttaatcgggc    180

ttctcggaca atctatgcag actccgtgag ggccgattc accatctcca gagacaatgc    240

caagaatttg gtgtatctgc aaatgaacaa cctgaaacct gaggacacag ccgtctatta    300

ttgtaatgta atagcgacca gcgcgtcggg gcgcggggtc acgtcgactt cgtggggcca    360

ggggtctcag gtcaccgtct cctcggaacc caagacacca aaaccacaat cggcctctgc    420

ggcc                                                                 424
```

<210> SEQ ID NO 80
<211> LENGTH: 409
<212> TYPE: DNA
<213> ORGANISM: Artificial Sequence
<220> FEATURE:
<223> OTHER INFORMATION: DNA including the gene sequence coding for VHH antibody fragment

<400> SEQUENCE: 80

```
ggcccagccg gccatggctc agttgcagct cgtggagtct gggggaggct tggtgcaggc     60

tggggggtct ctgagactct cctgtgtagc ctctggattc ccgttcgcta gtagtgccat    120

ggcgtggttc cgccaggctc caggaaagga gcgtgagttt gtagcgtcga taagctaccg    180

tggtattacc acatattatg cgcaacccgt gaagggccga ttcaccatgt ccagagacaa    240

tgccaagaac acggtgtatc tgcaaatgaa cagcctgaaa cctgaggaca cggccgtgta    300

ttactgctac gcaaaatcta tctggggtaa tgcctactgg ggccagggga cccaggtcac    360

cgtctcgcca gaacccaaga caccaaaacc acaatcggcc tctgcggcc                409
```

<210> SEQ ID NO 81
<211> LENGTH: 424
<212> TYPE: DNA
<213> ORGANISM: Artificial Sequence
<220> FEATURE:
<223> OTHER INFORMATION: DNA including the gene sequence coding for VHH antibody fragment

<400> SEQUENCE: 81

```
ggcccagccg gccatggctc agttgcagct cgtggagcct gggggaggtg tggtgcagcc     60

ggggggtct ctgagacttt cctgtttagc ctctggaagc gacttcagtc tcggtgccat     120

gggctggtat cgccaggcgc cagggaaaca gcgcgagctg gtcgccatta ttaatcgggc    180

ttcttggaca cgttatgcag actccgtgaa gggccgcttc accatctcca gagacaattc    240

caagaacttg gtgtttctgc aaatgaacaa cctgaaacct gacgacacag ccgtctatta    300

ctgtaatgca atagcgacca gcgcgtcggg gcgcggggtc acgtcgactt cgtggggcca    360

ggggtctcag gtcaccgtct cctcggaacc caagacacca aaaccacaat cggcctctgc    420

ggcc                                                                 424
```

<210> SEQ ID NO 82
<211> LENGTH: 430
<212> TYPE: DNA
<213> ORGANISM: Artificial Sequence
<220> FEATURE:
<223> OTHER INFORMATION: DNA including the gene sequence coding for VHH antibody fragment

<400> SEQUENCE: 82

```
ggcccagccg gccatggcta tggctgaggt gcagctcgtg gagtctgggg gaggattggt     60

gcaggctggg ggctctctga gactctcctg cgcagtctct ggacgcacct ccagtcgtta    120

tgtcatgggc tgggtccgcc aggctcccgg gaaggagcgt gagtttctgg cagctattag    180

ctggagtgct ggctacacat tctatcgaga ctccgtgaag ggccgattca ccatctcccg    240

agacaacgcc aagaacacgg tgtatctgca aatgaacagc ctgaaacctg aggacacggc    300

cgtatattac tgcaatgcag atgagaacgg gttgggccgg aagaggggct ttggttcctg    360

gggccagggg acccaggtca ccgtctcctc ggaacccaag acaccaaaac cacaatcggc    420

ctctgcggcc                                                           430
```

<210> SEQ ID NO 83
<211> LENGTH: 424
<212> TYPE: DNA
<213> ORGANISM: Artificial Sequence
<220> FEATURE:
<223> OTHER INFORMATION: DNA including the gene sequence coding for VHH antibody fragment

<400> SEQUENCE: 83

```
ggcccagccg gccatggcta tggctgagtt gcagctcgtg gagtctgggg gaggagcggt     60

gcacactggg ggctctctga ggctctcctg tgcagtatcg ggacgcaccg atattcgcta    120

tgccatgggc tggttccgcc aggctccagg gagggagcgt gagtttgtag ccgctattag    180

ctggaatggt gatgatacat tttatgcgga ttccgtgaag ggccgattca ccatctccag    240

ggacaacgcc aagaacgcgg tgtctctaca aatggacagc ctgagacctg aggacacggc    300

cgtctattac tgcaatgcgc gcaacagcta cgccgccttc gcgcgtgcct actggggcca    360

ggggacccag gtcaccgtct cctcagaacc caagacacca aaaccacaat cggcctctgc    420

ggcc                                                                 424
```

<210> SEQ ID NO 84
<211> LENGTH: 421
<212> TYPE: DNA
<213> ORGANISM: Artificial Sequence
<220> FEATURE:
<223> OTHER INFORMATION: DNA including the gene sequence coding for VHH antibody fragment

<400> SEQUENCE: 84

```
ggcccagccg gccatggcta tggctcagtt gcagctcgtg gagtctgggg gaggcttggt     60

gcagcctggg gggtctctga gactctcctg tgcagcctct ggattcactt tggattatta    120

tgccataggc tggttccgcc aggctccagg gaacgagcgt gagtttgtag cagctattag    180

ctggaatggt ggtagcacat actatgcaga ctccgtgaag ggccgattca ccatttccag    240

agacaacgcc aaggagacag tatatctgca aatgaacagc ctgaagcctg aggacacagg    300

tgtctattac tgtaattata gaccacaatt tggcctggga tataactatt ggggccaggg    360

gacccaggtc accgtctcct cagaacccaa gacaccaaaa ccacaatcgg cctctgcggc    420
```

```
c                                                                      421


<210> SEQ ID NO 85
<211> LENGTH: 420
<212> TYPE: DNA
<213> ORGANISM: Artificial Sequence
<220> FEATURE:
<223> OTHER INFORMATION: SfiI-treated DNA

<400> SEQUENCE: 85

cggccatggc tcaggtgcag ctcgtggagt ctgggggagg tgtggtgcag actgggggt      60

ctctgagact ttcctgtgca gcctctggaa gtactttcag tatcggtgcc atgggctggt    120

accgccaggc gccagggaag cagcgcgagt tggtcgccac tgttaatcgg gcttctcgga    180

caatctatgc agactccgtg aggggccgat tcaccatctc cagagacaat gccaagaatt    240

tggtgtatct gcaaatgaac aacctgaaac ctgaggacac agccgtctat tattgtaatg    300

taatagcgac cagcgcgtcg ggcgcggggg tcacgtcgac ttcgtggggc caggggtctc    360

aggtcaccgt ctcctcggaa cccaagacac caaaaccaca atcggcctct gcggcctctg    420


<210> SEQ ID NO 86
<211> LENGTH: 405
<212> TYPE: DNA
<213> ORGANISM: Artificial Sequence
<220> FEATURE:
<223> OTHER INFORMATION: SfiI-treated DNA

<400> SEQUENCE: 86

cggccatggc tcagttgcag ctcgtggagt ctgggggagg cttggtgcag gctgggggt      60

ctctgagact ctcctgtgta gcctctggat tcccgttcgc tagtagtgcc atggcgtggt    120

tccgccaggc tccaggaaag gagcgtgagt ttgtagcgtc gataagctac cgtggtatta    180

ccacatatta tgcgcaaccc gtgaagggcc gattcaccat gtccagagac aatgccaaga    240

acacggtgta tctgcaaatg aacagcctga aacctgagga cacggccgtg tattactgct    300

acgcaaaatc tatctggggt aatgcctact ggggccaggg gacccaggtc accgtctcgc    360

cagaacccaa gacaccaaaa ccacaatcgg cctctgcggc ctctg                    405


<210> SEQ ID NO 87
<211> LENGTH: 420
<212> TYPE: DNA
<213> ORGANISM: Artificial Sequence
<220> FEATURE:
<223> OTHER INFORMATION: SfiI-treated DNA

<400> SEQUENCE: 87

cggccatggc tcagttgcag ctcgtggagc ctgggggagg tgtggtgcag ccgggggggt     60

ctctgagact ttcctgttta gcctctggaa gcgacttcag tctcggtgcc atgggctggt    120

atcgccaggc gccagggaaa cagcgcgagc tggtcgccat tattaatcgg gcttcttgga    180

cacgttatgc agactccgtg aagggccgct tcaccatctc cagagacaat tccaagaact    240

tggtgtttct gcaaatgaac aacctgaaac ctgacgacac agccgtctat tactgtaatg    300

caatagcgac cagcgcgtcg ggcgcggggg tcacgtcgac ttcgtggggc caggggtctc    360

aggtcaccgt ctcctcggaa cccaagacac caaaaccaca atcggcctct gcggcctctg    420


<210> SEQ ID NO 88
<211> LENGTH: 426
<212> TYPE: DNA
<213> ORGANISM: Artificial Sequence
```

<220> FEATURE:
<223> OTHER INFORMATION: SfiI-treated DNA

<400> SEQUENCE: 88

```
cggccatggc tatggctgag gtgcagctcg tggagtctgg gggaggattg gtgcaggctg     60

ggggctctct gagactctcc tgcgcagtct ctggacgcac ctccagtcgt tatgtcatgg    120

gctgggtccg ccaggctccc gggaaggagc gtgagtttct ggcagctatt agctggagtg    180

ctggctacac attctatcga gactccgtga agggccgatt caccatctcc cgagacaacg    240

ccaagaacac ggtgtatctg caaatgaaca gcctgaaacc tgaggacacg gccgtatatt    300

actgcaatgc agatgagaac gggttgggcc ggaagagggg ctttggttcc tggggccagg    360

ggacccaggt caccgtctcc tcggaaccca agacaccaaa accacaatcg gcctctgcgg    420

cctctg                                                                426
```

<210> SEQ ID NO 89
<211> LENGTH: 420
<212> TYPE: DNA
<213> ORGANISM: Artificial Sequence
<220> FEATURE:
<223> OTHER INFORMATION: SfiI-treated DNA

<400> SEQUENCE: 89

```
cggccatggc tatggctgag ttgcagctcg tggagtctgg gggaggagcg gtgcacactg     60

ggggctctct gaggctctcc tgtgcagtat cgggacgcac cgatattcgc tatgccatgg    120

gctggttccg ccaggctcca gggagggagc gtgagtttgt agccgctatt agctggaatg    180

gtgatgatac attttatgcg gattccgtga agggccgatt caccatctcc agggacaacg    240

ccaagaacgc ggtgtctcta caaatggaca gcctgagacc tgaggacacg gccgtctatt    300

actgcaatgc gcgcaacagc tacgccgcct tcgcgcgtgc ctactggggc caggggaccc    360

aggtcaccgt ctcctcagaa cccaagacac caaaaccaca atcggcctct gcggcctctg    420
```

<210> SEQ ID NO 90
<211> LENGTH: 417
<212> TYPE: DNA
<213> ORGANISM: Artificial Sequence
<220> FEATURE:
<223> OTHER INFORMATION: SfiI-treated DNA

<400> SEQUENCE: 90

```
cggccatggc tatggctcag ttgcagctcg tggagtctgg gggaggcttg gtgcagcctg     60

gggggtctct gagactctcc tgtgcagcct ctggattcac tttggattat tatgccatag    120

gctggttccg ccaggctcca gggaacgagc gtgagtttgt agcagctatt agctggaatg    180

gtggtagcac atactatgca gactccgtga agggccgatt caccatttcc agagacaacg    240

ccaaggagac agtatatctg caaatgaaca gcctgaagcc tgaggacaca ggtgtctatt    300

actgtaatta tagaccacaa tttggcctgg gatataacta ttggggccag ggacccagg     360

tcaccgtctc ctcagaaccc aagacaccaa aaccacaatc ggcctctgcg gcctctg       417
```

<210> SEQ ID NO 91
<211> LENGTH: 5
<212> TYPE: PRT
<213> ORGANISM: Artificial Sequence
<220> FEATURE:
<223> OTHER INFORMATION: Linker

<400> SEQUENCE: 91

Gly Gly Gly Gly Ser
1 5

<210> SEQ ID NO 92
<211> LENGTH: 6
<212> TYPE: PRT
<213> ORGANISM: Artificial Sequence
<220> FEATURE:
<223> OTHER INFORMATION: Linker

<400> SEQUENCE: 92

Ser Gly Gly Gly Gly Ser
1 5

<210> SEQ ID NO 93
<211> LENGTH: 15
<212> TYPE: PRT
<213> ORGANISM: Artificial Sequence
<220> FEATURE:
<223> OTHER INFORMATION: Linker

<400> SEQUENCE: 93

Gly Gly Gly Gly Ser Gly Gly Gly Ala Ser Gly Gly Gly Gly Ser
1 5 10 15

<210> SEQ ID NO 94
<211> LENGTH: 15
<212> TYPE: PRT
<213> ORGANISM: Artificial Sequence
<220> FEATURE:
<223> OTHER INFORMATION: Linker

<400> SEQUENCE: 94

Ser Gly Gly Gly Gly Ser Ala Gly Gly Gly Ser Gly Gly Gly Gly
1 5 10 15

<210> SEQ ID NO 95
<211> LENGTH: 45
<212> TYPE: DNA
<213> ORGANISM: Artificial Sequence
<220> FEATURE:
<223> OTHER INFORMATION: Primer

<400> SEQUENCE: 95
aaaagctagc ggtggtggtg gatccsagkt gcagctcgtg gagtc 45

<210> SEQ ID NO 96
<211> LENGTH: 52
<212> TYPE: DNA
<213> ORGANISM: Artificial Sequence
<220> FEATURE:
<223> OTHER INFORMATION: Primer

<400> SEQUENCE: 96
caggtcacyg tctcctcagg tggtggtggt tctggtggtg gtgctagcaa aa 52

<210> SEQ ID NO 97
<211> LENGTH: 804
<212> TYPE: DNA
<213> ORGANISM: Artificial Sequence
<220> FEATURE:
<223> OTHER INFORMATION: DNA coding for protein-binding antibody

<400> SEQUENCE: 97
caggtgcagc tcgtggagtc tgggggaggt gtggtgcaga ctggggggtc tctgagactt 60
tcctgtgcag cctctggaag tactttcagt atcggtgcca tgggctggta ccgccaggcg 120
ccagggaagc agcgcgagtt ggtcgccact gttaatcggg cttctcggac aatctatgca 180
gactccgtga ggggccgatt caccatctcc agagacaatg ccaagaattt ggtgtatctg 240
caaatgaaca acctgaaacc tgaggacaca gccgtctatt attgtaatgt aatagcgacc 300
agcgcgtcgg ggcgcggggt cacgtcgact tcgtggggcc aggggtctca ggtcactgtc 360
tcctcaggtg gtggtggttc tggtggtggt gctagcggtg gtggtggatc ccaggtgcag 420
ctcgtggagt ctgggggagg cttggtgcag gctggtaagt ctctgagact ctcctgtaca 480
gcgtctggaa gcatccccag tatcggtgtc atgggctggc accgccaggc tccagggaag 540
cagcgcgagt tggtcgcgac tatttcgcag ggtggtcaca taaactattt tgagtccgtg 600
aagggccgat tcaccatctc cagagacaac gccaagaaca cggtgtatct gcaaatgaac 660
agcctgaaac ctgaggacac aggcgtctat tactgtaatg cgttttggct tccattgcgc 720
ctgaatgact actggggcca ggggacccag gtcaccgtct cctcagaacc caagacacca 780
aaaccacaat cggcctctgc ggcc 804

<210> SEQ ID NO 98
<211> LENGTH: 804
<212> TYPE: DNA
<213> ORGANISM: Artificial Sequence
<220> FEATURE:
<223> OTHER INFORMATION: DNA coding for protein-binding antibody

<400> SEQUENCE: 98
caggtgcagc tcgtggagtc tgggggaggc ttggtgcagg ctggtaagtc tctgagactc 60
tcctgtacag cgtctggaag catccccagt atcggtgtca tgggctggca ccgccaggct 120
ccagggaagc agcgcgagtt ggtcgcgact atttcgcagg gtggtcacat aaactatttt 180
gagtccgtga agggccgatt caccatctcc agagacaacg ccaagaacac ggtgtatctg 240
caaatgaaca gcctgaaacc tgaggacaca ggcgtctatt actgtaatgc gttttggctt 300
ccattgcgcc tgaatgacta ctggggccag gggacccagg tcaccgtctc ctcaggtggt 360
ggtggttctg gtggtggtgc tagcggtggt ggtggatccc aggtgcagct cgtggagtct 420
gggggaggtg tggtgcagac tgggggggtct ctgagacttt cctgtgcagc ctctggaagt 480
actttcagta tcggtgccat gggctggtac cgccaggcgc cagggaagca gcgcgagttg 540
gtcgccactg ttaatcgggc ttctcggaca atctatgcag actccgtgag gggccgattc 600
accatctcca gagacaatgc caagaatttg gtgtatctgc aaatgaacaa cctgaaacct 660
gaggacacag ccgtctatta ttgtaatgta atagcgacca gcgcgtcggg gcgcggggtc 720
acgtcgactt cgtggggcca ggggtctcag gtcaccgtct cctcggaacc caagacacca 780
aaaccacaat cggcctctgc ggcc 804

<210> SEQ ID NO 99
<211> LENGTH: 789
<212> TYPE: DNA
<213> ORGANISM: Artificial Sequence
<220> FEATURE:
<223> OTHER INFORMATION: DNA coding for protein-binding antibody

<400> SEQUENCE: 99
caggtgcagc tcgtggagtc tgggggaggc ttggtgcagg ctggtaagtc tctgagactc 60
tcctgtacag cgtctggaag catccccagt atcggtgtca tgggctggca ccgccaggct 120
ccagggaagc agcgcgagtt ggtcgcgact atttcgcagg gtggtcacat aaactatttt 180

```
gagtccgtga agggccgatt caccatctcc agagacaacg ccaagaacac ggtgtatctg    240

caaatgaaca gcctgaaacc tgaggacaca ggcgtctatt actgtaatgc gttttggctt    300

ccattgcgcc tgaatgacta ctggggccag ggacccagg tcaccgtctc ctcaggtggt    360

ggtggttctg gtggtggtgc tagcggtggt ggtggatccc agttgcagct cgtggagtct    420

gggggaggct tggtgcaggc tgggggggtct ctgagactct cctgtgtagc ctctggattc    480

ccgttcgcta gtagtgccat ggcgtggttc cgccaggctc caggaaagga gcgtgagttt    540

gtagcgtcga taagctaccg tggtattacc acatattatg cgcaacccgt gaagggccga    600

ttcaccatgt ccagagacaa tgccaagaac acggtgtatc tgcaaatgaa cagcctgaaa    660

cctgaggaca cggccgtgta ttactgctac gcaaaatcta tctggggtaa tgcctactgg    720

ggccagggga cccaggtcac cgtctcgcca gaacccaaga caccaaaacc acaatcggcc    780

tctgcggcc                                                            789
```

<210> SEQ ID NO 100
<211> LENGTH: 268
<212> TYPE: PRT
<213> ORGANISM: Artificial Sequence
<220> FEATURE:
<223> OTHER INFORMATION: Protein-binding antibody

<400> SEQUENCE: 100

```
Gln Val Gln Leu Val Glu Ser Gly Gly Gly Val Val Gln Thr Gly Gly
1               5                   10                  15

Ser Leu Arg Leu Ser Cys Ala Ala Ser Gly Ser Thr Phe Ser Ile Gly
            20                  25                  30

Ala Met Gly Trp Tyr Arg Gln Ala Pro Gly Lys Gln Arg Glu Leu Val
        35                  40                  45

Ala Thr Val Asn Arg Ala Ser Arg Thr Ile Tyr Ala Asp Ser Val Arg
    50                  55                  60

Gly Arg Phe Thr Ile Ser Arg Asp Asn Ala Lys Asn Leu Val Tyr Leu
65                  70                  75                  80

Gln Met Asn Asn Leu Lys Pro Glu Asp Thr Ala Val Tyr Tyr Cys Asn
                85                  90                  95

Val Ile Ala Thr Ser Ala Ser Gly Arg Gly Val Thr Ser Thr Ser Trp
            100                 105                 110

Gly Gln Gly Ser Gln Val Thr Val Ser Ser Gly Gly Gly Gly Ser Gly
        115                 120                 125

Gly Gly Ala Ser Gly Gly Gly Gly Ser Gln Val Gln Leu Val Glu Ser
    130                 135                 140

Gly Gly Gly Leu Val Gln Ala Gly Lys Ser Leu Arg Leu Ser Cys Thr
145                 150                 155                 160

Ala Ser Gly Ser Ile Pro Ser Ile Gly Val Met Gly Trp His Arg Gln
                165                 170                 175

Ala Pro Gly Lys Gln Arg Glu Leu Val Ala Thr Ile Ser Gln Gly Gly
            180                 185                 190

His Ile Asn Tyr Phe Glu Ser Val Lys Gly Arg Phe Thr Ile Ser Arg
        195                 200                 205

Asp Asn Ala Lys Asn Thr Val Tyr Leu Gln Met Asn Ser Leu Lys Pro
    210                 215                 220

Glu Asp Thr Gly Val Tyr Tyr Cys Asn Ala Phe Trp Leu Pro Leu Arg
225                 230                 235                 240

Leu Asn Asp Tyr Trp Gly Gln Gly Thr Gln Val Thr Val Ser Ser Glu
                245                 250                 255
```

```
Pro Lys Thr Pro Lys Pro Gln Ser Ala Ser Ala Ala
            260                 265


<210> SEQ ID NO 101
<211> LENGTH: 268
<212> TYPE: PRT
<213> ORGANISM: Artificial Sequence
<220> FEATURE:
<223> OTHER INFORMATION: Protein-binding antibody

<400> SEQUENCE: 101

Gln Val Gln Leu Val Glu Ser Gly Gly Gly Leu Val Gln Ala Gly Lys
1               5                   10                  15

Ser Leu Arg Leu Ser Cys Thr Ala Ser Gly Ser Ile Pro Ser Ile Gly
            20                  25                  30

Val Met Gly Trp His Arg Gln Ala Pro Gly Lys Gln Arg Glu Leu Val
        35                  40                  45

Ala Thr Ile Ser Gln Gly Gly His Ile Asn Tyr Phe Glu Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Gly Val Tyr Tyr Cys Asn
                85                  90                  95

Ala Phe Trp Leu Pro Leu Arg Leu Asn Asp Tyr Trp Gly Gln Gly Thr
            100                 105                 110

Gln Val Thr Val Ser Ser Gly Gly Gly Gly Ser Gly Gly Gly Ala Ser
        115                 120                 125

Gly Gly Gly Gly Ser Gln Val Gln Leu Val Glu Ser Gly Gly Gly Val
    130                 135                 140

Val Gln Thr Gly Gly Ser Leu Arg Leu Ser Cys Ala Ala Ser Gly Ser
145                 150                 155                 160

Thr Phe Ser Ile Gly Ala Met Gly Trp Tyr Arg Gln Ala Pro Gly Lys
                165                 170                 175

Gln Arg Glu Leu Val Ala Thr Val Asn Arg Ala Ser Arg Thr Ile Tyr
            180                 185                 190

Ala Asp Ser Val Arg Gly Arg Phe Thr Ile Ser Arg Asp Asn Ala Lys
        195                 200                 205

Asn Leu Val Tyr Leu Gln Met Asn Asn Leu Lys Pro Glu Asp Thr Ala
    210                 215                 220

Val Tyr Tyr Cys Asn Val Ile Ala Thr Ser Ala Ser Gly Arg Gly Val
225                 230                 235                 240

Thr Ser Thr Ser Trp Gly Gln Gly Ser Gln Val Thr Val Ser Ser Glu
                245                 250                 255

Pro Lys Thr Pro Lys Pro Gln Ser Ala Ser Ala Ala
            260                 265


<210> SEQ ID NO 102
<211> LENGTH: 263
<212> TYPE: PRT
<213> ORGANISM: Artificial Sequence
<220> FEATURE:
<223> OTHER INFORMATION: Protein-binding antibody

<400> SEQUENCE: 102

Gln Val Gln Leu Val Glu Ser Gly Gly Gly Leu Val Gln Ala Gly Lys
1               5                   10                  15

Ser Leu Arg Leu Ser Cys Thr Ala Ser Gly Ser Ile Pro Ser Ile Gly
```

-continued

```
            20                  25                  30

Val Met Gly Trp His Arg Gln Ala Pro Gly Lys Gln Arg Glu Leu Val
        35                  40                  45

Ala Thr Ile Ser Gln Gly Gly His Ile Asn Tyr Phe Glu Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Gly Val Tyr Tyr Cys Asn
                85                  90                  95

Ala Phe Trp Leu Pro Leu Arg Leu Asn Asp Tyr Trp Gly Gln Gly Thr
            100                 105                 110

Gln Val Thr Val Ser Ser Gly Gly Gly Gly Ser Gly Gly Gly Ala Ser
        115                 120                 125

Gly Gly Gly Gly Ser Gln Leu Gln Leu Val Glu Ser Gly Gly Gly Leu
    130                 135                 140

Val Gln Ala Gly Gly Ser Leu Arg Leu Ser Cys Val Ala Ser Gly Phe
145                 150                 155                 160

Pro Phe Ala Ser Ser Ala Met Ala Trp Phe Arg Gln Ala Pro Gly Lys
                165                 170                 175

Glu Arg Glu Phe Val Ala Ser Ile Ser Tyr Arg Gly Ile Thr Thr Tyr
            180                 185                 190

Tyr Ala Gln Pro Val Lys Gly Arg Phe Thr Met Ser Arg Asp Asn Ala
        195                 200                 205

Lys Asn Thr Val Tyr Leu Gln Met Asn Ser Leu Lys Pro Glu Asp Thr
    210                 215                 220

Ala Val Tyr Tyr Cys Tyr Ala Lys Ser Ile Trp Gly Asn Ala Tyr Trp
225                 230                 235                 240

Gly Gln Gly Thr Gln Val Thr Val Ser Pro Glu Pro Lys Thr Pro Lys
                245                 250                 255

Pro Gln Ser Ala Ser Ala Ala
            260
```

ANTIBODY CAPABLE OF BINDING TO NOROVIRUS, COMPOSITE, DETECTION DEVICE AND METHOD USING THE SAME

INCORPORATION BY REFERENCE-SEQUENCE LISTING

The material contained in the ASCII text file named "P1016328US01_ST25.txt" created on Mar. 25, 2019 and having a file size of 70,602 bytes is incorporated by reference herein.

BACKGROUND

1. Technical Field

The present invention relates to an antibody capable of binding to norovirus, a composite, a detection device and a method using the same.

2. Description of the Related Art

Patent Literature 1 discloses an antibody which is a divalent structure. At least a part of the antibodies disclosed in Patent Literature 1 is capable of binding to a norovirus. Patent Literature 1 is incorporated herein by reference.

CITATION LIST

Patent Literature

Patent Literature 1
U.S. Pat. No. 9,193,780

SUMMARY

An object of the present invention is to provide a novel antibody capable of binding to a norovirus, a composite, a detection device and a method using the same.

The present invention provides an antibody including a structural domain represented by the following amino acid sequence, in an N- to C-direction,

N-FR1-CDR1-FR2-CDR2-FR3-CDR3-FR4-C wherein the antibody further includes a protein molecule bound to the structural domain;

the structural domain is capable of binding to a norovirus;

FR denotes a framework region amino acid sequence and CDR denotes a complementary determining region amino acid sequence;

any one of the following requirements (i)-(iii) is satisfied.

Requirement (i):

the CDR1 includes an amino acid sequence having a sequence identity of not less than 60% with any one of the amino acid sequences represented by SEQ ID NO: 1-SEQ ID NO: 6, the CDR2 includes an amino acid sequence having a sequence identity of not less than 60% with any one of the amino acid sequences represented by SEQ ID NO: 7-SEQ ID NO: 12, and the CDR3 includes an amino acid sequence having a sequence identity of not less than 60% with any one of the amino acid sequences represented by SEQ ID NO: 13-SEQ ID NO: 17;

Requirement (ii):

the CDR1 includes an amino acid sequence in which one-three amino acid(s) of any one of the amino acid sequence represented by SEQ ID NO: 1-SEQ ID NO: 6 has/have been substituted, deleted, or added, the CDR2 includes an amino acid sequence in which one-three amino acid(s) of any one of the amino acid sequence represented by SEQ ID NO: 7-SEQ ID NO: 12 has/have been substituted, deleted, or added, and the CDR3 includes an amino acid sequence in which one-three amino acid(s) of any one of the amino acid sequence represented by SEQ ID NO: 13-SEQ ID NO: 17 has/have been substituted, deleted, or added; and Requirement (iii):

the CDR1 includes any one of the amino acid sequence represented by SEQ ID NO: 1-SEQ ID NO: 6, the CDR2 includes any one of the amino acid sequence represented by SEQ ID NO: 7-SEQ ID NO: 13, and the CDR3 includes any one of the amino acid sequence represented by SEQ ID NO: 13-SEQ ID NO: 17.

The present invention provides a novel antibody capable of binding to a norovirus, a composite, a detection device and a method using the same.

DETAILED DESCRIPTION OF THE EMBODIMENT

Figure 1A:
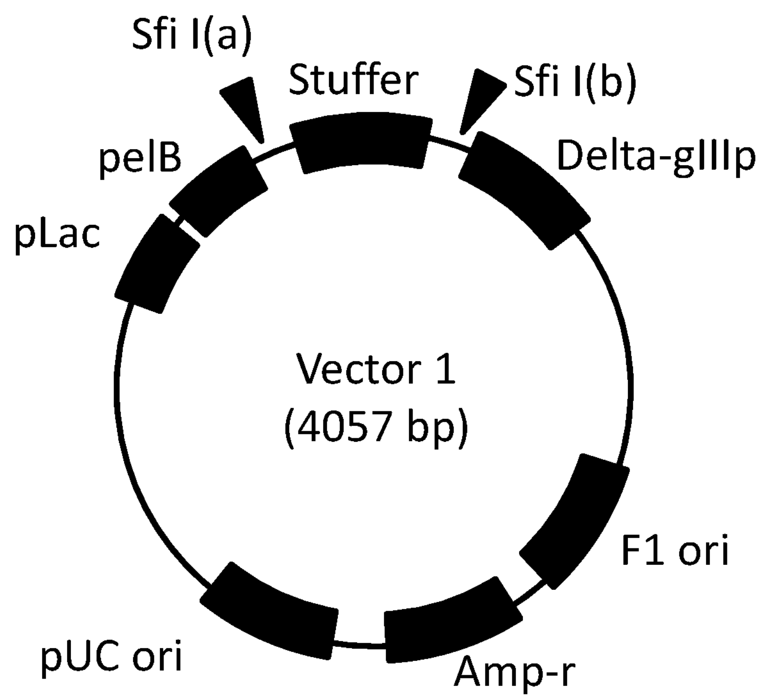
FIG. 1A is a map of a vector used to ligate various genes included in a gene library of a VHH antibody.

The term 'antibody' in the present specification includes, for example, an antibody, a single chain antibody, a heavy chain antibody, an antigen binding portion, and a VHH antibody. The antibody of the invention may be bound or fused to a peptide, an oligopeptide, or a protein.

The term "sequence identity" in the present specification means a percentage of identical bases or amino acids at corresponding positions in two or more sequences which are aligned in consideration of gaps and insertions in such a way that the degree of the identity of the sequences is maximized. A method for determining the identity is designed to give the largest degree of accordance between the aligned sequences. A method for determining the identity between two sequences includes, but is not limited to, BLASTP, BLASTN, or FASTA. Alternatively, the determination can be made using DNASIS (manufactured by Hitachi Software Engineering Co., Ltd.) or GENETYX (manufactured by Genetics Co., Ltd.). Alternatively, a short peptide can be determined simply by comparing the sequences thereof. One skilled in the art can determine the identity between sequences in the above-described way.

In the present disclosure, the binding ability of an antibody to an antigen can be evaluated by a method publicly known to one skilled in the art. In particular, evaluation can be performed by determining a dissociation constant Kd by a method using the following noro antigen and surface plasmon resonance evaluation apparatus (i.e., SPR method). In addition, for example, evaluation can be performed by a method using an ELISA method in which an antigen is immobilized.

The present invention relates to an antibody capable of binding to the norovirus. In one embodiment, the antibody according to the present invention is capable of binding to a GII/4 norovirus. In an embodiment disclosed more specifically, the antibody according to the present disclosure recognizes an epitope included in the SEQ ID NO: 48. The antibody according to the present disclosure is capable of binding to a norovirus and includes an amino acid sequence including, in an N- to C-direction, the following structural domain:

N-FR1-CDR1-FR2-CDR2-FR3-CDR3-FR4-C wherein

FR denotes a framework region amino acid sequence and CDR denotes a complementary determining region amino acid sequence.

In one aspect, the CDR1 of the structural domain according to the present disclosure includes or consists of any one of the amino acid sequences represented by SEQ ID NO: 1-SEQ ID NO: 6. In one aspect, the CDR2 of the structural domain according to the present disclosure includes or consists of any one of the amino acid sequences represented by SEQ ID NO: 7-SEQ ID NO: 12. In one aspect, the CDR3 of the structural domain according to the present disclosure includes or consists of any one of the amino acid sequences represented by SEQ ID NO: 13-SEQ ID NO: 17.

An example of the combination of the CDR1, the CDR2, and the CDR3 is:

CDR1=SEQ ID NO: 1, CDR2=SEQ ID NO: 7, and CDR3=SEQ ID NO: 13;

CDR1=SEQ ID NO: 2, CDR2=SEQ ID NO: 8, and CDR3=SEQ ID NO: 14;

CDR1=SEQ ID NO: 3, CDR2=SEQ ID NO: 9, and CDR3=SEQ ID NO: 13;

CDR1=SEQ ID NO: 4, CDR2=SEQ ID NO: 10, and CDR3=SEQ ID NO: 15;

CDR1=SEQ ID NO: 5, CDR2=SEQ ID NO: 11, and CDR3=SEQ ID NO: 16; or

CDR1=SEQ ID NO: 6, CDR2=SEQ ID NO: 12, and CDR3=SEQ ID NO: 17.

In one embodiment, the CDR1, the CDR2, and the CDR3 of the structural domain according to the present disclosure includes a CDR sequence having an amino acid sequence having the sequence identity of not less than 60%, not less than 70%, not less than 75%, not less than 80%, not less than 85%, not less than 86%, not less than 87%, not less than 88%, not less than 89%, not less than 90%, not less than 91%, not less than 92%, not less than 93%, not less than 94%, not less than 95%, not less than 96%, not less than 97%, not less than 98%, or not less than 99%, respectively, with the CDR1 represented by any one of SEQ ID NO: 1-SEQ ID NO: 6, the CDR2 represented by any one of SEQ ID NO: 7-SEQ ID NO: 12, and the CDR3 represented by any one of SEQ ID NO: 13-SEQ ID NO: 17.

In one embodiment, the CDR1, the CDR2, and the CDR3 of the structural domain according to the present disclosure includes the CDR1, the CDR2, and the CDR3, each having an amino acid sequence in which one or more (for example, two or three) amino acid(s) has/have been substituted in, deleted from, or added to the CDR1, the CDR2, and the CDR3, respectively.

In one embodiment, the FR1 includes or consists of any one of the amino acid sequences represented by SEQ ID NO: 18-SEQ ID NO: 23. In one embodiment, the FR2 includes or consists of any one of the amino acid sequences represented by SEQ ID NO: 24-SEQ ID NO: 28. In one embodiment, the FR3 includes or consists of any one of the amino acid sequences represented by SEQ ID NO: 29-SEQ ID NO: 34. In one embodiment, the FR4 includes or consists of any one of the amino acid sequences represented by SEQ ID NO: 35-SEQ ID NO: 37.

An example of the combination of the FR1, the FR2, the FR3, and the FR4 is:

FR1=SEQ ID NO: 18, FR2=SEQ ID NO: 24, FR3=SEQ ID NO: 29, and FR4=SEQ ID NO: 35;

FR1=SEQ ID NO: 19, FR2=SEQ ID NO: 25, FR3=SEQ ID NO: 30, and FR4=SEQ ID NO: 36;

FR1=SEQ ID NO: 20, FR2=SEQ ID NO: 24, FR3=SEQ ID NO: 31, and FR4=SEQ ID NO: 35;

FR1=SEQ ID NO: 21, FR2=SEQ ID NO: 26, FR3=SEQ ID NO: 32, and FR4=SEQ ID NO: 37;

FR1=SEQ ID NO: 22, FR2=SEQ ID NO: 27, FR3=SEQ ID NO: 33, and FR4=SEQ ID NO: 37; and FR1=SEQ ID NO: 23, FR2=SEQ ID NO: 28, FR3=SEQ ID NO: 34, and FR4=SEQ ID NO: 37.

In one embodiment, the FR1, the FR2, the FR3, and the FR4 of the structural domain according to the present disclosure includes a FR sequence having an amino acid sequence having the sequence identity of not less than 60%, not less than 70%, not less than 75%, not less than 80%, not less than 85%, not less than 86%, not less than 87%, not less than 88%, not less than 89%, not less than 90%, not less than 91%, not less than 92%, not less than 93%, not less than 94%, not less than 95%, not less than 96%, not less than 97%, not less than 98%, or not less than 99%, respectively, with the FR1 represented by any one of SEQ ID NO: 18-SEQ ID NO: 23, the FR2 represented by any one of SEQ ID NO: 24-SEQ ID NO: 28, the FR3 represented by any one of SEQ ID NO: 29-SEQ ID NO: 34, and the FR4 represented by any one of SEQ ID NO: 35-SEQ ID NO: 37.

In one embodiment, the FR1, the FR2, the FR3, and the FR4 of the structural domain according to the present disclosure includes the FR1, the FR2, the FR3, and the FR4 each having an amino acid sequence in which one or more (for example, two or three) amino acid(s) has/have been substituted in, deleted from, or added to the FR1, the FR2, the FR3, and the FR4, respectively.

In an embodiment disclosed in more specifically, the antibody according to the present disclosure includes a structural domain including or consisting of any one of the amino acids represented by SEQ ID NO: 38-SEQ ID NO: 43.

In one embodiment, the antibody according to the present disclosure includes the structural domain including or consisting of an amino acid sequence having the sequence identity of not less than 60%, not less than 70%, not less than 75%, not less than 80%, not less than 85%, not less than 86%, not less than 87%, not less than 88%, not less than 89%, not less than 90%, not less than 91%, not less than 92%, not less than 93%, not less than 94%, not less than 95%, not less than 96%, not less than 97%, not less than 98%, or not less than 99%, respectively, with any one of the amino acid sequences represented by SEQ ID NO: 38-SEQ ID NO: 43.

In one embodiment, the antibody according to the present disclosure includes a structural domain including or consisting of an amino acid sequence in which one or more (for example, two or three) amino acid has/have been substituted in, deleted from, or added to any one of the amino acid sequences represented by SEQ ID NO: 38-SEQ ID NO: 43.

An example of the antibody including the above structural domain is an antibody including or consisting of any one of the amino acid sequences represented by SEQ ID NO: 66-SEQ ID NO: 71.

In one aspect, the present disclosure provides an antibody bound to a protein. In the antibody bound to the protein, a protein molecule is connected to the structural domain. In one embodiment, the protein molecule according to the present aspect has an amino acid sequence length of, for example, 100-300, 100-150, or 115-135. In another embodiment, the protein molecule according to the present aspect is, for example, an antibody, a single-stranded antibody, a heave-chain antibody, a part bound to an antigen, or a VHH antibody. In one embodiment, the protein molecule according to the present aspect does not bind to the norovirus.

In the present aspect, the structural domain and the protein molecule may be linked directly to each other. Alternatively, the structural domain and the protein molecule may be linked with a linker to each other. In one embodiment, the linker has an amino acid length of 5-60. An example of a preferable amino acid length of the linker is 5-30, 5-20, 5-10, 10-30, or 10-20. In one embodiment, the linker includes the sequence represented by GGGGS (SEQ ID NO: 91) or SGGGGS (SEQ ID NO: 92). A specific example of the linker is GGGGSGGGASGGGGS (SEQ ID NO: 93) or SGGGGSAGGGSGGGG (SEQ ID NO: 94).

The antibody bound to the protein according to the present aspect has a stronger binding ability to the norovirus than a monomer antibody which does not include the protein molecule. For example, according to the SPR evaluation, the monomer antibody has a dissociation constant Kd of approximately 50-150 nM, whereas the antibody bound to the protein has a dissociation constant Kd of approximately 1-10 nM.

In the present invention, the antibody bound to the protein according to the present aspect includes any one of the amino acid sequences represented by SEQ ID NO: 45-SEQ ID NO: 47.

In one embodiment, the antibody bound to the protein according to the present aspect includes an amino acid sequence having the sequence identity of not less than 60%, not less than 70%, not less than 75%, not less than 80%, not less than 85%, not less than 86%, not less than 87%, not less than 88%, not less than 89%, not less than 90%, not less than 91%, not less than 92%, not less than 93%, not less than 94%, not less than 95%, not less than 96%, not less than 97%, not less than 98%, or not less than 99%, with any one of the amino acid sequences represented by SEQ ID NO: 45-SEQ ID NO: 47.

In one embodiment, the antibody bound to the protein according to the present aspect includes an amino acid sequence in which one or more (for example, two or three) amino acid(s) has/have been substituted in, deleted from, or added to any one of the amino acid sequences represented by SEQ ID NO: 45-SEQ ID NO: 47.

An specific example of the antibody bound to the protein according to the present aspect is an antibody bound to the protein including or consisting of any one of the amino acid sequences represented by SEQ ID NO: 100-SEQ ID NO: 102.

A production method of the antibody according to the present disclosure is not limited in particular. The antibody according to the present disclosure may be synthesized from amino acid, or produced by transfecting a host cell with a DNA coding for the antibody according to the present disclosure. A production method of the antibody bound to the protein according to the present disclosure is also not limited in particular. The antibody bound to the protein according to the present disclosure may be produced by linking the two antibodies with the linker or directly. If the two antibodies are linked with the liner, a DNA sequence coding for the structural domains linked to each other with the linker may be produced by a PCR method with primers.

The antibody according to the present invention can be employed in a detection device or in a detection method for detecting the norovirus. In this case, the antibody according to the present invention may be used in a state of a composite bound to another material, for example, in a state of a composite in which the antibody according to the present invention has been bound to at least one selected from the group consisting of a solid phase support and a labeled substance.

As long as the solid phase support is a support insoluble in a solvent used for a reaction system of an antigen-antibody reaction, a shape and a material of the solid phase support is not limited. An example of the shape of the solid phase support is a plate, a bead, a disk, a tube, a filter, and a film. An example of a material of the solid phase support is a polymer such as polyethylene terephthalate, cellulose acetate, polycarbonate, polystyrene, or polymethylmethacrylate, a metal such as gold, silver, or aluminum, or glass. A known method such as a physical adsorption method, a covalent binding method, an ion bonding method, or a cross-linking method is employed as a method for binding the antibody to the solid phase support.

For example, a labeled substance such as a fluorescent substance, a luminescent substance, a dye, an enzyme, or a radioactive substance is used. A known method such as a physical adsorption method, a covalent binding method, an ion bonding method, or a cross-linking method is employed as a method for binding the antibody to the labeled substance.

In the detection method in which the antibody according to the present invention is used, the composite including the antibody is brought into contact with an analyte. Then, detected is a change of a physical amount based on an antigen-antibody reaction of the norovirus contained in the analyte and the antibody included in the composite. An example of the physical amount is luminescence intensity, chromaticity, light transmission, turbidness, absorbance, or radiation dose. A known method such as an enzyme immunoassay method, an immunochromatography method, a latex agglutination method, a radioimmunoassay method, a fluorescence immunoassay method, or a surface plasmon resonance spectroscopy method is employed as an example of the detection method.

The detection device in which the antibody according to the present invention is employed includes a detector for detecting any one of the physical amount which is changed on the basis of the antigen-antibody reaction. The detector is composed of a known device such as a photometer, a spectroscope, or a dosimeter.

The antibody may be used not only as a composite bound to another material but also as a composition including the antibody according to the present invention or as a kit including the antibody according to the present invention.

EXAMPLES

Inventive Example 1

(Production of Monomer Antibody)

VHH antibodies (i.e., a variable domain of a heavy chain of a heavy chain antibody) were prepared in accordance with the following procedures as a peptide capable of binding to a protein which exists on a surface of a GII/4 norovirus.

(Immunization of Alpaca and Acquirement of Mononuclear)

In order to form a VHH antibody gene library, an antigen derived from the GII/4 norovirus (NSW-2012) was prepared. In other words, a p-domain protein of the GII/4 norovirus (NSW-2012), which is a capsid protein existing on the surface of the norovirus, was converted into its recombinant. An alpaca was immunized using the recombinant p-domain protein as the antigen of the norovirus (SEQ ID NO: 48). Hereinafter, the antigen of the norovirus is referred to as "noro antigen". The noro antigen was prepared with an adjuvant before the immunization of the alpaca.

The sequence of the noro antigen (SEQ ID NO: 48, which is a recombinant of the p-domain protein of the GII/4 norovirus (NSW-2012)) used in the inventive example 1 was shown below.

```
                                        (SEQ ID NO: 48)
MKMASNDANPSDGSTANLVPEVNNEVMALEPVVGAAIAAPVAGQQNVIDP

WIRNNFVQAPGGEFTVSPRNAPGEILWSAPLGPDLNPYLSHLARMYNGYA

GGFEVQVILAGNAFTAGKIIFAAVPPNFPTEGLSPSQVTMFPHIIVDVRQ

LEPVLIPLPDVRNNFYHYNQSNDPTIKLIAMLYTPLRANNAGDDVFTVSC

RVLTRPSPDFDFIFLVPPTVESRTKPFSVPVLTVEEMTNSRFPIPLEKLF
```

-continued

```
TGPSSAFVVQPQNGRCTTDGVLLGTTQLSPVNICTFRGDVTHITGSRNYT

MNLASQNWNSYDPTEEIPAPLGTPDFVGKIQGVLTQTTRTDGSTRGHKAT

VYTGSADFSPKLGRVQFATDTDNDFETNQNTKFTPVGVIQDGGTTHRNEP

QQWVLPSYSGRNTHNVHLAPAVAPTFPGEQLLFFRSTMPGCSGYPNMDLD

CLLPQEWVQYFYQEAAPAQSDVALLRFVNPDTGRVLFECKLHKSGYVTVA

HTGQHDLVIPPNGYFRFDSWVNQFYTLAPMGNGTGRRRAL
```

Specifically, the noro antigen having a concentration of 100 micrograms/milliliter was administered to the alpaca. After one week, the noro antigen having the same concentration was administered to the alpaca, again. In this way, the alpaca was immunized with the noro antigen five times over five weeks. After another week, blood of the alpaca was extracted. Then, mononuclear cells were acquired from the blood as below.

A blood cell separation solution (available from COSMO BIO Co., Ltd., trade name: Lymphoprep) was added to a lymphocyte separation tube (available from Greiner Bio-One Co., Ltd., trade name: Leucosep). Then, the solution was subjected to centrifugation at 1,000×g at a temperature of 20 degrees Celsius for one minute.

The blood extracted from the alpaca was treated with heparin. Then, an equivalent amount of phosphate buffered saline (hereinafter, referred to as "PBS") was added to the thus-treated blood to provide a sample solution. Then, the sample solution was added to the lymphocyte separation tube containing the blood cell separation solution.

The lymphocyte separation tube was subjected to centrifugation at 800×g at a temperature of 20 degrees Celsius for thirty minutes.

A fraction containing mononuclear cells was collected. Three times its volume of PBS was added. The fraction was subjected to centrifugation at 300×g at a temperature of 20 degrees Celsius for five minutes. The precipitate was suspended with PBS gently. After the suspending, 10 microliters of the suspension was separated in order for the count of the number of cells. The remaining suspension was subjected to centrifugation at 300×g at a temperature of 20 degrees Celsius for five minutes.

An RNA storage solution (trade name: RNAlater) having a volume of 2 milliliters was added to the precipitate. Then, the solution was suspended gently. The suspension was injected into two tubes each having a volume of 1.5 milliliters. Each tube contained 1 milliliter of the suspension. The tube was stored at a temperature of −20 degrees Celsius. The suspension (5 microliters) separated for the count of the number of cells was mixed with a Türk's solution (15 microliters), and the number of the mononuclear cells was counted with a counting chamber.

(Formation of cDNA Gene Library of VHH Antibody)

Then, a total RNA was extracted from the mononuclear cells, and a cDNA gene library of the VHH antibody was formed in accordance with the following procedure. In the following procedure, RNase-free-grade reagents and instruments were used.

A total RNA isolation reagent (trade name: TRIzol Reagent, 1 milliliter) was added to the mononuclear cell fraction. The reagent was mixed gently with the fraction, and left at rest at room temperature for five minutes. Chloroform (200 microliters) was added to the reagent, and the reagent was shaken strongly for fifteen seconds. The reagent was left at rest at room temperature for two-three minutes. The reagent was subjected to centrifugation at 12,000×g or less at a temperature of 4 degrees Celsius for 15 minutes.

The supernatant was moved to a new tube. RNase-free water and chloroform (200 microliters, each) were added to the tube. In addition, 500 milliliters of isopropanol was added to the tube. The liquid contained in the tube was stirred with a vortex mixer. The liquid was left at rest at room temperature for ten minutes. Then, the liquid was subjected to centrifugation at 12,000×g or less at a temperature of 4 degrees Celsius for fifteen minutes. The supernatant was removed, and the precipitate was rinsed with one milliliter of 75% ethanol. This solution was subjected to centrifugation at 7,500×g or less at a temperature of four degrees Celsius for five minutes. The solution was dried to obtain total RNA. The obtained total RNA was dissolved in RNase-free water.

In order to obtain cDNA from the total RNA, a kit including a reverse transcriptase was employed. The kit was available from Takara Bio Inc., as a trade name of PrimeScript II 1st strand cDNA Synthesis Kit. The Random 6 mer and 01igo dT primer included in the kit were used as primers. The cDNA was obtained in accordance with the standard protocol attached to the kit.

The gene of the VHH antibody included in the alpaca was obtained from the cDNA by a PCR method. An enzyme for PCR was available from Takara Bio Inc., as a trade name of Ex-taq.

The following reagents were mixed to obtain a mixture solution.

| | |
|---|---|
| 10x buffer | 5 microliters |
| dNTPs | 4 microliters |
| Primer F | 2 microliters |
| Primer R | 2 microliters |
| cDNA template | 1 microliter |
| Ex-taq | 0.25 microliters |

The mixture solution was subjected to the following PCR method.

First, the mixture solution was heated at a temperature of 95 degrees Celsius for two minutes.

Then, the temperature of the mixture solution was varied in accordance with the following cycle.

Ninety six degrees Celsius for thirty seconds,

Fifty two degrees Celsius for thirty seconds, and

Sixty eight degrees Celsius for forty seconds

This cycle was repeated thirty times.

Finally, the mixture solution was heated at a temperature of sixty eight degrees Celsius for four minutes and stored at a temperature of four degrees Celsius.

The following primers were used in the present PCR method.

```
Primer 1:
                                        (SEQ ID NO: 49)
5'-GGTGGTCCTGGCTGC-3'

Primer 2:
                                        (SEQ ID NO: 50)
5'-ctgctcctcgcGGCCCAGCCGGCCatggcTSAGKTGCAGCTCGTGGA
GTC-3'

Primer 3:
                                        (SEQ ID NO: 51)
5'-TGGGGTCTTCGCTGTGGTGCG-3'
```

-continued

```
Primer 4:
                                        (SEQ ID NO: 52)
5'-TTGTGGTTTTGGTGTCTTGGG-3'

Primer 5:
                                        (SEQ ID NO: 53)
5'-tttgCtctGCGGCCGCagaGGCCgTGGGGTCTTCGCTGTGGTGC
G-3'

Primer 6:
                                        (SEQ ID NO: 54)
5'-tttgCtctGCGGCCGCagaGGCCgaTTGTGGTTTTGGTGTCTTGG
G-3'
(Reference literature: Biomed Environ Sci., 2012; 27(2):118-
121)
```

Three PCR assays were conducted.

In the first PCR assay, a primer set A composed of the cDNA, Primer 1 and Primer 3 and a primer set B composed of the cDNA, Primer 1 and Primer 4 were used.

In the second PCR assay, a primer set C composed of the gene amplified with the primer set A, Primer 2, and Primer 3, and a primer set D composed of the gene amplified with the primer set B, Primer 2, and Primer 4 were used.

In the third PCR assay, a primer set E composed of the gene amplified with the primer set C, Primer 2, and Primer 5, and a primer set F composed of the gene amplified with the primer set D, Primer 2, and Primer 6 were used.

In this way, the gene library of the VHH antibody was formed. In other words, the gene library of the VHH antibody included the genes amplified with the primer sets E and F.

(Formation of Phage Library)

Next, a phage library was formed from the gene library of the VHH antibody in accordance of the following procedures.

Figure 1B:
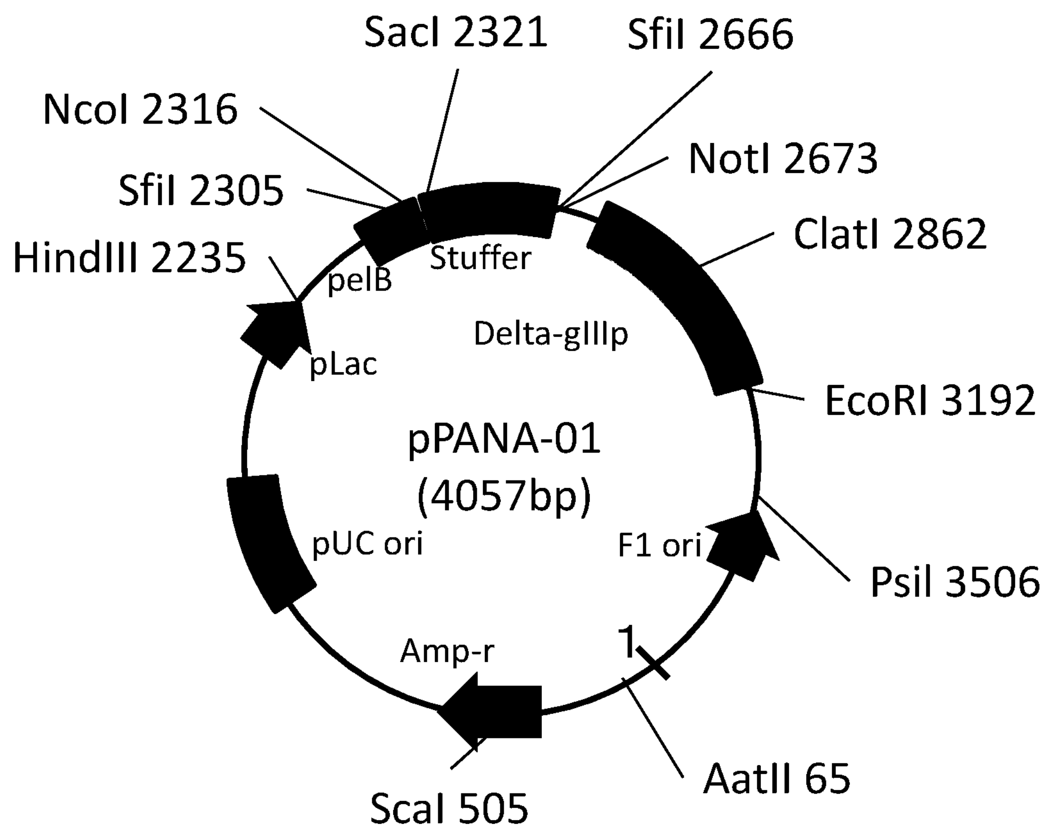
FIG. 1B shows the detail of the vector map shown in FIG. 1A.

A plasmid Vector 1 (4057 bp, see FIG. 1A) derived from a commercially available plasmid pUC119 (for example, available from Takara Bio Inc.) was treated with a restriction enzyme SfiI. The restriction enzyme site SfiI(a) in FIG. 1A consists of the gene sequence represented by GGCCCAGCCGGCC (SEQ ID NO: 55). The restriction enzyme site SfiI(b) consists of the gene sequence represented by GGCCTCTGCGGCC (SEQ ID NO: 56). FIG. 1B shows a detailed vector map of the plasmid Vector 1.

The plasmid Vector 1 consists of the following gene sequence.

```
                                        (SEQ ID NO: 57)
gacgaaagggcctcgtgatacgcctatttttataggttaatgtcatgata

ataatggtttcttagacgtcaggtggcacttttcggggaaatgtgcgcgg

aacccctatttgtttatttttctaaatacattcaaatatgtatccgctca

tgagacaataaccctgataaatgcttcaataatattgaaaaaggaagagt

atgagtattcaacatttccgtgtcgcccttattcccttttttgcggcatt

ttgccttcctgtttttgctcacccagaaacgctggtgaaagtaaaagatg

ctgaagatcagttgggtgcacgagtgggttacatcgaactggatctcaac

agcggtaagatccttgagagttttcgccccgaagaacgttttccaatgat

gagcacttttaaagttctgctatgtggcgcggtattatcccgtattgacg

ccgggcaagagcaactcggtcgccgcatacactattctcagaatgacttg

gttgagtactcaccagtcacagaaaagcatcttacggatggcatgacagt
```

-continued

```
aagagaattatgcagtgctgccataaccatgagtgataacactgcggcca
acttacttctgacaacgatcggaggaccgaaggagctaaccgcttttttg
cacaacatgggggatcatgtaactcgccttgatcgttgggaaccggagct
gaatgaagccataccaaacgacgagcgtgacaccacgatgcctgtagcaa
tggcaacaacgttgcgcaaactattaactggcgaactacttactctagct
tcccggcaacaattaatagactggatggaggcggataaagttgcaggacc
acttctgcgctcggcccttccggctggctggtttattgctgataaatctg
gagccggtgagcgtgggtctcgcggtatcattgcagcactggggccagat
ggtaagccctcccgtatcgtagttatctacacgacggggagtcaggcaac
tatggatgaacgaaatagacagatcgctgagataggtgcctcactgatta
agcattggtaactgtcagaccaagtttactcatatatactttagattgat
ttaaaacttcatttttaatttaaaaggatctaggtgaagatcctttttga
taatctcatgaccaaaatcccttaacgtgagttttcgttccactgagcgt
cagaccccgtagaaaagatcaaaggatcttcttgagatcctttttttctg
cgcgtaatctgctgcttgcaaacaaaaaaaccaccgctaccagcggtggt
ttgtttgccggatcaagagctaccaactctttttccgaaggtaactggct
tcagcagagcgcagataccaaatactgtccttctagtgtagccgtagtta
ggccaccacttcaagaactctgtagcaccgcctacatacctcgctctgct
aatcctgttaccagtggctgctgccagtggcgataagtcgtgtcttaccg
ggttggactcaagacgatagttaccggataaggcgcagcggtcgggctga
acggggggttcgtgcacacagcccagcttggagcgaacgacctacaccga
actgagatacctacagcgtgagctatgagaaagcgccacgcttcccgaag
ggagaaaggcggacaggtatccggtaagcggcagggtcggaacaggagag
cgcacgagggagcttccagggggaaacgcctggtatctttatagtcctgt
cgggtttcgccacctctgacttgagcgtcgatttttgtgatgctcgtcag
gggggcggagcctatggaaaaacgccagcaacgcggcctttttacggttc
ctggccttttgctggccttttgctcacatgttctttcctgcgttatcccc
tgattctgtggataaccgtattaccgcctttgagtgagctgataccgctc
gccgcagccgaacgaccgagcgcagcgagtcagtgagcgaggaagcggaa
gagcgcccaatacgcaaaccgcctctccccgcgcgttggccgattcatta
atgcagctggcacgacaggtttcccgactggaaagcgggcagtgagcgca
acgcaattaatgtgagttagctcactcattaggcaccccaggctttacac
tttatgcttccggctcgtatgttgtgtggaattgtgagcggataacaatt
tcacacaggaaacagctatgaccatgattacgccAAGCTTCGAAGGAGAC
AGTCATAatgaaatacctgctgccgaccgctgctgctggtctgctgctcc
tcgcGGCCCAGCCGGCCatggagcTCAAGATGACACAGACTACATCCTCC
CTGTCAGCCTCTCTGGGAGACAGAGTCACCATCAGTTGCAGGGCAAGTCA
GGACATTAGCGATTATTTAAACTGGTATCAGCAGAAACCAGATGGAACTG
TTAAACTCCTGATCTATTACACATCAAGTTTACACTCAGGAGTCCCATCA
AGGTTCAGTGGCGGTGGGTCTGGAACAGATTATTCTCTCACCATTAGCAA
CCTGGAGCAAGAAGATATTGCCACTTACTTTTGCCAACAGGGTAATACGC
```

-continued

```
TTCCGTGGACGTTTGGTGGAGGCACCAAGCTGGAAATCAAACGGGCTGAT
GCTGCACCAACTgtaGGCCtctGCGGCCGCagaGcaaaaactcatctcag
aagaggatctgaatggggccgcaTAGggttccggtgattttgattatgaa
aagatggcaaacgctaataagggggctatgaccgaaaatgccgatgaaaa
cgcgctacagtctgacgctaaaggcaaacttgattctgtcgctactgatt
acggtgctgctatcgatggtttcattggtgacgtttccggccttgctaat
ggtaatggtgctactggtgattttgctggctctaattcccaaatggctca
agtcggtgacggtgataattcacctttaatgaataatttccgtcaatatt
taccttccctccctcaatcggttgaatgtcgcccttttgtctttagcgct
ggtaaaccatatgaattttctattgattgtgacaaaataaacttattccg
tggtgtctttgcgtttcttttatatgttgccacctttatgtatgtatttt
ctacgtttgctaacatactgcgtaataaggagtctTAATAAgaattcact
ggccgtcgttttacaacgtcgtgactgggaaaaccctggcgttacccaac
ttaatcgccttgcagcacatccccctttcgccagctggcgtaatagcgaa
gaggcccgcaccgatcgcccttcccaacagttgcgcagcctgaatggcga
atggcgcctgatgcggtattttctccttacgcatctgtgcggtatttcac
accgCATATGaAAATTGTAAgcgttaatattttgttaaaattcgcgttaa
atttttgttaaatcagctcattttttaaccaataggccgaaatcggcaaa
atcccttataaatcaaaagaatagaccgagatagggttgagtgttgttcc
agtttggaacaagagtccactattaaagaacgtggactccaacgtcaaag
ggcgaaaaaccgtctatcagggcgatggcccactacgtgaaccatcaccc
taatcaagttttttggggtcgaggtgccgtaaagcactaaatcggaaccc
taaagggagcccccgatttagagcttgacggggaaagccggcgaacgtgg
cgagaaaggaagggaagaaagcgaaaggagcgggcgctagggcgctggca
agtgtagcggtcacgctgcgcgtaaccaccacacccgccgcgcttaatgc
gccgctacaGGGCGCGTcccatATGgtgcactctcagtacaatctgctct
gatgccgcatagttaagccagccccgacacccgccaacacccgctgacgc
gccctgacgggcttgtctgctcccggcatccgcttacagacaagctgtga
ccgtctccgggagctgcatgtgtcagaggttttcaccgtcatcaccgaaa
cgcgcga
```

Similarly, the gene library of the VHH antibody was treated with the restriction enzyme SfiI. In this way, VHH antibody gene fragments were obtained.

The thus-treated plasmid Vector 1 was mixed with the VHH antibody gene fragments at a ratio of 1:2. An enzyme (available from Toyobo Co. Ltd., trade name: Ligation High ver. 2) was injected into the mixture solution. The mixture solution was left at rest at a temperature of 16 degrees Celsius for two hours. In this way, each of the VHH antibody gene fragments was ligated into the plasmid Vector 1.

Coli bacteria (available from Takara Bio Inc., trade name: HST02) were transfected with the thus-ligated plasmid Vector 1.

Then, the coli bacteria were incubated for fifteen hours on a 2YT plate culture medium containing ampicillin at a concentration of 100 micrograms/milliliter. In this way, obtained was a library of phages each of which displays a protein obtained from the gene fragment included in the gene library of the VHH antibody.

After the incubation, a concentration of the library was calculated by counting the number of single colonies formed on the 2YT plate culture medium. As a result, the library of the phages had a concentration of 5 E+7/milliliter.

(Biopanning)

VHH antibodies capable of specifically binding to the noro antigen (i.e., the recombinant of the p-domain protein of the GII/4 norovirus (NSW-2012), the recombinant being represented by SEQ ID NO: 48) were obtained from the phage library in accordance with the following procedures.

In order to extract the clones each capable of binding to the antigen from among the phages which expressed the VHH antibody, biopanning was conducted twice.

Coli bacteria (HST02) to which the VHH antibody gene fragment included in the gene library of the VHH antibody had been introduced were incubated at a temperature of 30 degrees Celsius in the 2YT AG culture medium containing 100 micrograms/milliliter of ampicillin and 1% glucose until a value $OD_{600}$ indicating absorbance reached 1.0. The 2YT AG culture medium had a volume of 100 milliliters. In this way, the coli bacteria were proliferated.

Helper phages (available from Invitrogen company, trade name: M13K07) were added to the coli bacteria culture medium in such a manner that the multiplicity of infection (hereinafter, referred to as "MOI") was approximately twenty.

Then, the culture medium was warmed for about thirty minutes at a temperature of 37 degrees Celsius. Then, the culture medium was subjected to centrifugation at a rotation speed of 4000 rpm for ten minutes to collect the coli bacteria. The coli bacteria were incubated overnight at a temperature of 30 degrees Celsius in a 2YTAK culture medium containing 100 micrograms/milliliter of ampicillin and 50 micrograms/milliliter of kanamycin, while subjected to centrifugation at 213 rpm. The 2YTAK culture medium had a volume of 100 milliliters.

The incubation liquid (100 milliliters) containing the thus-incubated coli bacteria was injected into two centrifugation tubes (volume: 50 milliliters, each). The two centrifugation tubes were subjected to centrifugation for ten minutes at a rotation speed of 4,000 rpm. Then, the supernatants (20 milliliters, each) were collected.

The supernatants (40 milliliters) were added to a 20% polyethylene glycol solution (10 milliliters) containing NaCl (2.5 M). Then, the mixture solution was inverted and mixed. Subsequently, the mixture solution was cooled on ice for approximately one hour. The mixture was subjected to centrifugation for ten minutes at a rotation speed of 4,000 rpm. Then, the supernatant was removed. PBS containing 10% glycerol was injected toward the precipitate. Finally, the precipitate was loosened and dissolved. In this way, a library of phages each of which displays the VHH antibody was obtained.

(Screening of VHH Antibody Capable of Specifically Binding to Noro Antigen)

(A) Immobilization of Noro Antigen

The noro antigen was mixed with PBS to prepare a norovirus solution. The concentration of norovirus was 2 micrograms/milliliter. The norovirus solution (2 milliliters) was injected into an immunotube (available from NUNC Co. Ltd.). The norovirus solution was left at rest overnight in the immunotube. In this way, norovirus was immobilized in the immunotube.

Then, the inside of the immunotube was washed three times with PBS.

The inside of the immunotube was filled with PBS which contained 3% skim milk (available from Wako Pure Chemical Industries, Ltd.). In this way, norovirus was blocked as an antigen in the immunotube.

The immunotube was left at rest at room temperature for one hour. Subsequently, the inside of the immunotube was washed three times with PBS.

(B) Panning

The library of the phages each of which displays the VHH antibody (concentration: approximately 5E+11/milliliter) was mixed with 3 milliliters of PBS containing 3% skim milk to prepare a mixture solution. The mixture solution was injected into the immunotube in which the noro antigen was immobilized.

The immunotube was provided with a lid formed of Parafilm. Then, the immunotube was rotated upside down in a rotator for ten minutes.

The immunotube was left at rest at room temperature for one hour.

The inside of the immunotube was washed ten times with PBS containing 0.05% Tween 20. Hereinafter, such PBS is referred to as "PBST".

The inside of the immunotube was filled with PBST. Subsequently, the immunotube was left at rest for ten minutes. Then, the inside of the immunotube was washed ten times with PBST.

In order to extract phages each of which displays the VHH antibody bound to the noro antigen, 100 mM trimethylamine solution (1 milliliter) was injected into the immunotube.

The immunotube was provided with a lid formed of Parafilm. Then, the immunotube was rotated upside down in a rotator for ten minutes.

In order to neutralize the solution, the solution was moved to a tube containing 1 mL of 0.5 M Tris/HCl (pH: 6.8). Again, the extraction of the phage was repeated using a 100 mM trimethylamine solution (1 milliliter). In this way, 3 mL of an extraction liquid was obtained.

The extraction liquid (1 mL) was mixed with 9 mL of coli bacteria HST02. The mixture solution was left at rest for one hour at a temperature of 30 degrees Celsius.

In order to count the number of colonies, 10 microliters of the mixture solution containing the coli bacteria HST02 was distributed onto a small plate containing a 2TYA culture medium (10 milliliters/plate).

The rest of the mixture solution was subjected to centrifugation. The supernatant was removed, and the precipitate was distributed onto a large plate containing a 2TYA culture medium (40 milliliters/plate). These two plates were left at rest overnight at a temperature of 30 degrees Celsius. In this way, first panning was conducted.

Second panning was conducted identically to the procedure of the first panning. In other words, the panning was repeated. In this way, the monoclonal phages on which the VHH antibody was displayed were purified.

After the second panning, a colony of the coli bacteria was picked up with a toothpick. The picked-up one colony was put onto one well of 96-flat-bottom plate. This was repeated. One well contained 200 microliters of a 2YTAG culture medium.

The solutions contained in the wells were stirred at a rotation speed of 213 rpm at a temperature of 30 degrees Celsius.

The solution (50 microliters) containing grown coli bacteria was collected. The collected solution was mixed with 50 microliters of a 2YTA culture medium contained in a plate. The 2YTA culture medium contained helper phages such that the multiplicity of infection (i.e., MOI) was set to be 20. The solution was left at rest at a temperature of 37 degrees Celsius for forty minutes.

The plate containing the 2YTA culture medium was subjected to centrifugation at 1, 800 rpm for twenty minutes. The supernatant was removed. The precipitate contained the coli bacteria. The precipitate was mixed with 200 microliters of a 2YTAK culture medium. The mixture solution was left at rest overnight at a temperature of 30 degrees Celsius.

The mixture solution was subjected to centrifugation at 1, 800 rpm for twenty minutes. The supernatant containing the coli bacteria was collected.

(C) Qualitative Evaluation of Phage-Displayed VHH Antibody and Antigen by ELISA

A solution containing the noro antigen (i.e., the recombinant of the p-domain protein of the GII/4 norovirus (NSW-2012), the recombinant being represented by SEQ ID NO: 48) having a concentration of 2 micrograms/milliliter was injected as an antigen into each of the wells of a 96-well plate (available from Thermo Fisher Scientific K.K., trade name: maxisorp). The volume of the solution containing the noro antigen in each well was 50 microliters. The 96-well plate was left at rest overnight at a temperature of 4 degrees Celsius. In this way, the noro antigen was immobilized in each well.

Each of the wells was washed with PBS three times. Then, PBS containing 3% skim milk (available from Wako Pure Chemical Industries, Ltd.) was injected into each well (200 microliters/well). The 96-well plate was left at rest at room temperature for one hour. In this way, the noro antigen was blocked in each well. Subsequently, each well was washed three times with PBS.

The monoclonal phages each of which displays the VHH antibody were injected into each well (50 microliters/well). Then, the 96-well plate was left at rest for one hour. In this way, the phages reacted with the noro antigen.

Each well was washed three times with PBST. Then, an anti-M13 antibody (available from ABCAM company, trade name: ab50370, 10,000-fold dilution) was injected into each well (50 microliters/well). Then, each well was washed three times with PBST.

A color-producing agent (available from Thermo Scientific, trade name: 1-step ultra TMB-ELISA) was injected into each well (50 microliters/well). The 96-well plate was left at rest for two minutes to cause the color-producing agent to react with the antibody.

A sulfuric acid aqueous solution (normal, i.e., 1 N) was injected into each well at a concentration of 50 microliters/well to cease the reaction.

The absorbance of the solution at a wavelength of 450 nanometers was measured.

Six wells each having good absorbance measurement result were selected. The DNA sequences included in the phages contained in the selected six wells were analyzed by Greiner Company. The analysis results of the DNA sequences will be described below. The following six DNA sequences were found.

(SEQ ID NO: 58)
caggtgcagctcgtggagtctgggggaggtgtggtgcagactgggggtc
tctgagactttcctgtgcagcctctggaagtactttcagtatcggtgcca
tgggctggtaccgccaggcgccagggaagcagcgcgagttggtcgccact
gttaatcgggcttctcggacaatctatgcagactccgtgaggggccgatt
caccatctccagagacaatgccaagaatttggtgtatctgcaaatgaaca -continued acctgaaacctgaggacacagccgtctattattgtaatgtaatagcgacc
agcgcgtcggggcgcggggtcacgtcgacttcgtggggccaggggtctca
ggtcaccgtctcctcggaacccaagacaccaaaaccacaatcggcctctg
cggcc (SEQ ID NO: 59)
cagttgcagctcgtggagtctgggggaggcttggtgcaggctgggggtc
tctgagactctcctgtgtagcctctggattcccgttcgctagtagtgcca
tggcgtggttccgccaggctccaggaaaggagcgtgagtttgtagcgtcg
ataagctaccgtggtattaccacatattatgcgcaacccgtgaagggccg
attcaccatgtccagagacaatgccaagaacacggtgtatctgcaaatga
acagcctgaaacctgaggacacggccgtgtattactgctacgcaaaatct
atctggggtaatgcctactggggccaggggacccaggtcaccgtctcgcc
agaacccaagacaccaaaaccacaatcggcctctgcggcc (SEQ ID NO: 60)
cagttgcagctcgtggagcctgggggaggtgtggtgcagccgggggggtc
tctgagactttcctgtttagcctctggaagcgacttcagtctcggtgcca
tgggctggtatcgccaggcgccagggaaacagcgcgagctggtcgccatt
attaatcgggcttcttggacacgttatgcagactccgtgaagggccgctt
caccatctccagagacaattccaagaacttggtgtttctgcaaatgaaca
acctgaaacctgacgacacagccgtctattactgtaatgcaatagcgacc
agcgcgtcggggcgcggggtcacgtcgacttcgtggggccaggggtctca
ggtcaccgtctcctcggaacccaagacaccaaaaccacaatcggcctctg
cggcc (SEQ ID NO: 61)
atggctgaggtgcagctcgtggagtctgggggaggattggtgcaggctgg
gggctctctgagactctcctgcgcagtctctggacgcacctccagtcgtt
atgtcatgggctgggtccgccaggctcccgggaaggagcgtgagtttctg
gcagctattagctggagtgctggctacacattctatcgagactccgtgaa
gggccgattcaccatctcccgagacaacgccaagaacacggtgtatctgc
aaatgaacagcctgaaacctgaggacacggccgtatattactgcaatgca
gatgagaacgggttgggccggaagaggggctttggttcctggggccaggg
gacccaggtcaccgtctcctcggaacccaagacaccaaaaccacaatcgg
cctctgcggcc (SEQ ID NO: 62)
atggctgagttgcagctcgtggagtctgggggaggagcggtgcacactgg
gggctctctgaggctctcctgtgcagtatcgggacgcaccgatattcgct
atgccatgggctggttccgccaggctccagggagggagcgtgagtttgta
gccgctattagctggaatggtgatgatacattttatgcggattccgtgaa
gggccgattcaccatctccagggacaacgccaagaacgcggtgtctctac
aaatggacagcctgagacctgaggacacggccgtctattactgcaatgcg -continued cgcaacagctacgccgccttcgcgcgtgcctactggggccaggggaccca ggtcaccgtctcctcagaacccaagacaccaaaaccacaatcggcctctg cggcc (SEQ ID NO: 63)

atggctcagttgcagctcgtggagtctgggggaggcttggtgcagcctgg ggggtctctgagactctcctgtgcagcctctggattcactttggattatt atgccataggctggttccgccaggctccagggaacgagcgtgagtttgta gcagctattagctggaatggtggtagcacatactatgcagactccgtgaa gggccgattcaccatttccagagacaacgccaaggagacagtatatctgc aaatgaacagcctgaagcctgaggacacaggtgtctattactgtaattat agaccacaatttggcctgggatataactattggggccaggggacccaggt caccgtctcctcagaacccaagacaccaaaaccacaatcggcctctgcgg cc The proteins synthesized from the DNA sequences represented by SEQ ID NO: 58-SEQ ID NO: 63 consist of the following amino acid sequences (SEQ ID NO: 66-SEQ ID NO: 71), respectively.

(SEQ ID NO: 66)

Gln Val Gln Leu Val Glu Ser Gly Gly Gly Val Val

Gln Thr Gly Gly Ser Leu

Arg Leu Ser Cys Ala Ala Ser Gly Ser Thr Phe Ser

Ile Gly Ala Met Gly Trp Tyr Arg

Gln Ala Pro Gly Lys Gln Arg Glu Leu Val Ala Thr

Val Asn Arg Ala Ser Arg Thr Ile

Tyr Ala Asp Ser Val Arg Gly Arg Phe Thr Ile Ser

Arg Asp Asn Ala Lys Asn Leu Val

Tyr Leu Gln Met Asn Asn Leu Lys Pro Glu Asp Thr

Ala Val Tyr Tyr Cys Asn Val Ile

Ala Thr Ser Ala Ser Gly Arg Gly Val Thr Ser Thr

Ser Trp Gly Gln Gly Ser Gln Val

Thr Val Ser Ser Glu Pro Lys Thr Pro Lys Pro Gln

Ser Ala Ser Ala Ala (SEQ ID NO: 67)

Gln Leu Gln Leu Val Glu Ser Gly Gly Gly Leu Val

Gln Ala Gly Gly Ser Leu

Arg Leu Ser Cys Val Ala Ser Gly Phe Pro Phe Ala

Ser Ser Ala Met Ala Trp Phe Arg

Gln Ala Pro Gly Lys Glu Arg Glu Phe Val Ala Ser

Ile Ser Tyr Arg Gly Ile Thr Thr

Tyr Tyr Ala Gln Pro Val Lys Gly Arg Phe Thr Met

Ser Arg Asp Asn Ala Lys Asn Thr

Val Tyr Leu Gln Met Asn Ser Leu Lys Pro Glu Asp

-continued

Thr Ala Val Tyr Tyr Cys Tyr Ala

Lys Ser Ile Trp Gly Asn Ala Tyr Trp Gly Gln Gly

Thr Gln Val Thr Val Ser Pro Glu

Pro Lys Thr Pro Lys Pro Gln Ser Ala Ser Ala Ala (SEQ ID NO: 68)

Gln Leu Gln Leu Val Glu Pro Gly Gly Gly Val Val

Gln Pro Gly Gly Ser Leu

Arg Leu Ser Cys Leu Ala Ser Gly Ser Asp Phe Ser

Leu Gly Ala Met Gly Trp Tyr Arg

Gln Ala Pro Gly Lys Gln Arg Glu Leu Val Ala Ile

Ile Asn Arg Ala Ser Trp Thr Arg

Tyr Ala Asp Ser Val Lys Gly Arg Phe Thr Ile Ser

Arg Asp Asn Ser Lys Asn Leu Val

Phe Leu Gln Met Asn Asn Leu Lys Pro Asp Asp Thr

Ala Val Tyr Tyr Cys Asn Ala Ile

Ala Thr Ser Ala Ser Gly Arg Gly Val Thr Ser Thr

Ser Trp Gly Gln Gly Ser Gln Val

Thr Val Ser Ser Glu Pro Lys Thr Pro Lys Pro Gln

Ser Ala Ser Ala Ala (SEQ ID NO: 69)

Glu Val Gln Leu Val Glu Ser Gly Gly Gly Leu Val

Gln Ala Gly Gly Ser Leu

Arg Leu Ser Cys Ala Val Ser Gly Arg Thr Ser Ser

Arg Tyr Val Met Gly Trp Val Arg

Gln Ala Pro Gly Lys Glu Arg Glu Phe Leu Ala Ala

Ile Ser Trp Ser Ala Gly Tyr Thr

Phe Tyr Arg Asp Ser Val Lys Gly Arg Phe Thr Ile

Ser Arg Asp Asn Ala Lys Asn Thr

Val Tyr Leu Gln Met Asn Ser Leu Lys Pro Glu Asp

Thr Ala Val Tyr Tyr Cys Asn Ala

Asp Glu Asn Gly Leu Gly Arg Lys Arg Gly Phe Gly

Ser Trp Gly Gln Gly Thr Gln Val

Thr Val Ser Ser Glu Pro Lys Thr Pro Lys Pro Gln

Ser Ala Ser Ala Ala (SEQ ID NO: 70)

Glu Leu Gln Leu Val Glu Ser Gly Gly Gly Ala Val

His Thr Gly Gly Ser Leu

Arg Leu Ser Cys Ala Val Ser Gly Arg Thr Asp Ile

Arg Tyr Ala Met Gly Trp Phe Arg

Gln Ala Pro Gly Arg Glu Arg Glu Phe Val Ala Ala

Ile Ser Trp Asn Gly Asp Asp Thr

Phe Tyr Ala Asp Ser Val Lys Gly Arg Phe Thr Ile

-continued

Ser Arg Asp Asn Ala Lys Asn Ala

Val Ser Leu Gln Met Asp Ser Leu Arg Pro Glu Asp

Thr Ala Val Tyr Tyr Cys Asn Ala

Arg Asn Ser Tyr Ala Ala Phe Ala Arg Ala Tyr Trp

Gly Gln Gly Thr Gln Val Thr Val

Ser Ser Glu Pro Lys Thr Pro Lys Pro Gln Ser Ala

Ser Ala Ala (SEQ ID NO: 71)

Gln Leu Gln Leu Val Glu Ser Gly Gly Gly Leu Val

Gln Pro Gly Gly Ser Leu

Arg Leu Ser Cys Ala Ala Ser Gly Phe Thr Leu Asp

Tyr Tyr Ala Ile Gly Trp Phe Arg

Gln Ala Pro Gly Asn Glu Arg Glu Phe Val Ala Ala

Ile Ser Trp Asn Gly Gly Ser Thr

Tyr Tyr Ala Asp Ser Val Lys Gly Arg Phe Thr Ile

Ser Arg Asp Asn Ala Lys Glu Thr

Val Tyr Leu Gln Met Asn Ser Leu Lys Pro Glu Asp

Thr Gly Val Tyr Tyr Cys Asn Tyr

Arg Pro Gln Phe Gly Leu Gly Tyr Asn Tyr Trp Gly

Gln Gly Thr Gln Val Thr Val Ser

Ser Glu Pro Lys Thr Pro Lys Pro Gln Ser Ala Ser

Ala Ala (Expression of Anti-Norovirus VHH Antibody)

Figure 2:
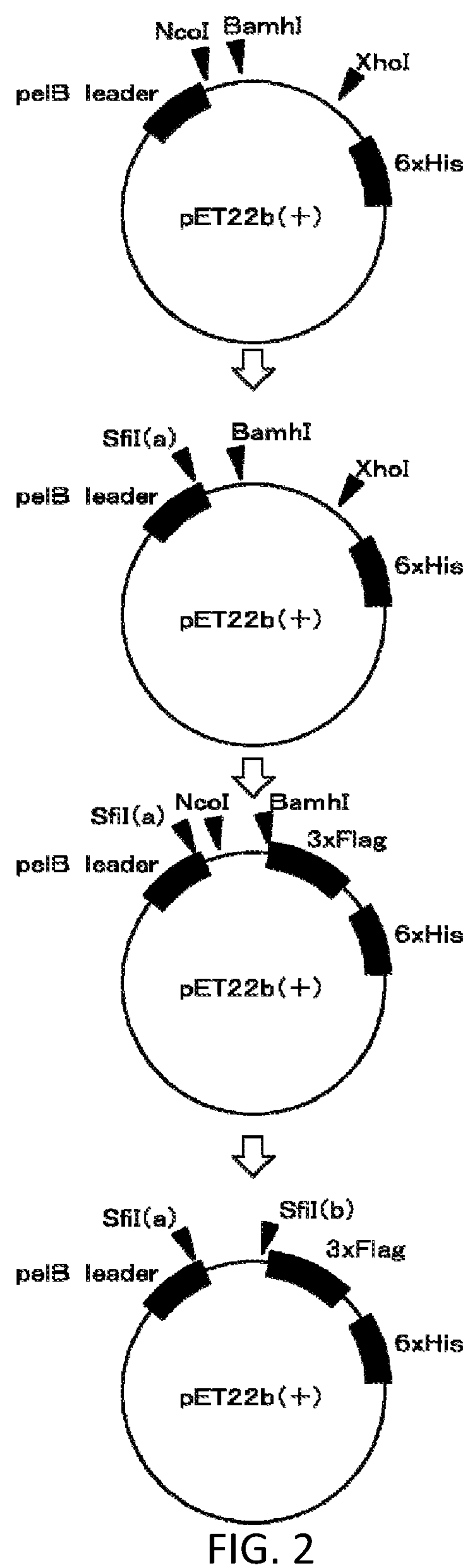
FIG. 2 shows a synthesis procedure of a vector used to express the VHH antibody.

A vector pET22b(+) was purchased from Merck Millipore Company. Using PrimeStar Mutagenesis Basal Kit (available from Takara Bio Inc.), a 3×Flag tag and two restriction enzyme sites SfiI(a) and SfiI(b) were added to the vector pET22b(+) by a PCR method. See FIG. 2. The procedure shown in FIG. 2 will be described below in more detail.

First, the restriction enzyme site SfiI(a) was add to the vector pET22b(+) by a PCR method using the following two primers and a restriction enzyme (available from Takara Bio Inc., trade name: PrimeSTAR Max DNA polymerase).

Primer 1:

(SEQ ID NO: 73)
5'-GCCGGCTGGGCcGCGAGGAGCAGCAGACCA-3'

Primer 2:

(SEQ ID NO: 74)
5'-GCCCAGCCGGCcATGGCCATGGATATCGGA-3'

Then, a 3×Flag tag DNA fragment having restriction enzyme sites BamhI and XhoI at 5'-terminal end and 3'-terminal end, respectively, was formed by a PCR method using the following two primers and restriction enzymes (available from Takara Bio Inc., trade name: PrimeSTAR Max DNA polymerase).

Primer 1:

(SEQ ID NO: 75)
5'-CATGGATATCGGAATTAATTCggatccGACTACAAAGACCATGACGG
TGATTATAAAGATCATGACATCctcgagCACCACCACCACCACCACTG
A-3'

Primer 2:

(SEQ ID NO: 76)
5'-TCAGTGGTGGTGGTGGTGGTGctcgagGATGTCATGATCTTTATAAT
CACCGTCATGGTCTTTGTAGTCggatccGAATTAATTCCGATATCCAT
G-3'

This 3×Flag tag DNA fragment and the vector pET22b(+) were treated with two restriction enzymes BamhI and XhoI (available from Takara Bio Inc.)

The 3×Flag tag DNA fragment was ligated into the vector pET22b(+) using Ligation Kit (available from Takara Bio Inc.). In this way, obtained was the vector pET22b(+) to which the 3×Flag tag and the restriction enzyme site SfiI(a) were added.

A DNA fragment having restriction enzyme sites NcoI and BamhI at 5'-terminal end and 3'-terminal end, respectively, was formed by a PCR method using the following two primers and restriction enzymes (available from Takara Bio Inc., trade name: PrimeSTAR Max DNA polymerase).

Primer 1:

(SEQ ID NO: 77)
5'-AAATACCTGCTGCCGccatggATATCGGAATTAATTCggcctctgcg
gccGCAggatccGACTACAAAGACCAT-3'

Primer 2:

(SEQ ID NO: 78)
5'-ATGGTCTTTGTAGTCggatccTGCggccgcagaggccGAATTAATTC
CGATATccatggCGGCAGCAGGTATTT-3'

Then, this DNA fragment and the vector pET22b(+) were treated with two restriction enzymes NcoI and BamhI (available from Takara Bio Inc.)

This DNA fragment was ligated into the vector pET22b (+) using Ligation Kit (available from Takara Bio Inc.). In this way, provided was the vector pET22b(+) to which the 3×Flag tag and the restriction enzyme sites SfiI (a) and SfiI (b) were added.

The sequence of the vector pET22b (+) was analyzed by Greiner Company. For the analysis of the sequence, a general T7 promotor primer set was used.

Selected were the vectors pET22b(+) which were confirmed through the analysis of the sequence to have been formed as planned.

Vectors pET22b(+) included in the liquid obtained by the PCR method were purified and collected in 50 microliters of diluted water using a DNA extraction kit (available from Promega KK). The thus-collected vectors pET22b (+) was treated with the SfiI restriction enzyme.

On the other hand, the plasmid Vector 1 into which the VHH antibody gene fragment included in the gene library of the VHH antibody was ligated was treated with the SfiI restriction enzyme. In this way, provided were the following six DNAs (SEQ ID NO: 79-SEQ ID NO: 84) including the gene sequence coding for the amino acid sequences represented by SEQ ID NO: 38-SEQ ID NO: 43.

These six DNAs were treated with the SfiI restriction enzyme. Then, the thus-treated DNAs were collected by an electrocataphoresis method. Using a DNA ligation kit (available from Takara Bio Inc.), the collected DNAs (SEQ ID NO: 85-SEQ ID NO: 90) were ligated into the plasmid treated with the SfiI restriction enzyme.

The ligation solution (2.5 microliters) and coli bacteria DH5α (available from Nippon Gene, 25 microliters) were mixed on ice. The mixture solution was left at rest on the ice for six minutes. Then, the mixture solution was heated at a temperature of 42 degrees Celsius for forty five seconds. Finally, the mixture solution was left at rest on the ice for one minute. This procedure is known as a general heat shock method.

The total amount of the mixture solution was distributed onto a LBA culture medium containing ampicillin at a concentration of 100 micrograms/milliliter. The LBA culture medium was left at rest overnight at a temperature of 37 degrees Celsius.

Three colonies were selected from among the colonies formed on the LBA culture medium. The selected three colonies were incubated in the LBA culture medium (3 milliliters) overnight.

The plasmids contained in the incubated coli bacteria were extracted from the LBA culture medium using a plasmid extraction kit (available from QIAGEN, trade name: QIAprepspin miniprep kit). In order to confirm that the gene of the targeted VHH antibody was inserted in the plasmid, the sequence of the plasmid was analyzed by Greiner Company. For the analysis of the sequence, a general T7 promotor primer set was used.

Selected were plasmids which were confirmed through the analysis of the sequence to have been formed as planned.

Coli bacteria (Competent Cell BL21 (DE3) pLysS, available from Life technologies Company) were transfected with the selected plasmids by a heat shock method.

An SOC culture medium (50 microliters) was injected into the solution containing the transfected coli bacteria. Then, the coli bacteria were rescued at a temperature of 37 degrees Celsius for one hour, while shaken at 213 rpm.

Then, the coli bacteria solution was collected. The collected coli bacteria solution (5 milliliters) was distributed onto a LBA culture medium. The LBA culture medium was left at rest overnight at a temperature of 37 degrees Celsius.

One colony was selected from among the colonies formed in the LBA culture medium. The selected colony was picked up with a toothpick. The picked-up colony was incubated in a LBA culture medium (3 milliliters) at a temperature of 37 degrees Celsius, while shaken at 213 rpm. In this way, a culture liquid was provided.

In addition, the culture liquid (25 milliliters) was mixed with a LBA culture medium (500 milliliters). Until the absorbance of the mixture solution at a wavelength of 600 nanometers reached 0.5, the mixture solution was shaken at 160 rpm at a temperature of 37 degrees Celsius.

After the absorbance reached 0.5, an isopropylthiogalactoside solution (hereinafter, referred to as "IPTG solution") was added to the mixture solution. The final concentration of the IPTG solution was 1 mM. The coli bacteria contained in the mixture solution were incubated at a temperature of 37 degrees Celsius for six hours. In order to collect the thus-incubated coli bacteria, the mixture solution was subjected to centrifugation at 6,000 rpm for ten minutes at a temperature of 4 degrees Celsius.

The collected coli bacteria were mixed with ten times its volume of PBS. The mixture solution was stirred with a vortex mixer. In this way, the coli bacteria were washed. Then, the mixture solution was subjected to centrifugation at 6,000 rpm for ten minutes at a temperature of 4 degrees Celsius to collect coli bacteria. The collected coli bacteria were mixed again with ten times its volume of PBS. The coli bacteria contained in the mixture solution were disintegrated with an ultrasonic wave.

The disintegration liquid containing coli bacteria was subjected to centrifugation at 10,000 rpm for fifteen minutes at a temperature of 4 degrees Celsius. The supernatant was collected. The collected supernatant was filtered through a 0.45-micrometer filter.

The filtrate was purified with His-trap (available from GE Healthcare) in accordance with the recommended protocol. In the purification, an elution buffer having a total amount of 3 microliters was used for 1 milliliter of the filtrate. The buffer solution contained in the filtrate was substituted with PBS, using PD-10 (available from GE Healthcare). In the substitution, PBS having a total amount of 2.5 microliters was used for 1 milliliter of the filtrate. In this way, a solution containing the VHH antibody was provided.

The VHH antibody contained in the thus-provided solution was quantified with an absorption spectrometer (available from Scrum Inc., trade name: nanodrop) on the basis of the absorption measurement value at a wavelength of 280 nanometers. As a result, the concentration of the VHH antibody was 4 milligrams/milliliter.

(D) Surface Plasmon Resonance Evaluation of VHH Antibody Using Noro Antigen

The VHH antibody was evaluated as below using the noro antigen and a surface plasmon resonance evaluation device. The details of the surface plasmon resonance (hereinafter, referred to as "SPR") will be described below.

SPR evaluation device: T200 (available from GE Healthcare)

Immobilization buffer: HBS-EP (available from GE Healthcare)

Running buffer: HBS-EP+ (available from GE Healthcare)

Sensor chip: CM5 (available from GE Healthcare)

Immobilization reagents: N-hydroxysuccinimide (NHS) and N-[3-(dimethylamino) propyl]-N'-ethylcarbodiimide (EDC)

Noro Antigen

The noro antigen was immobilized in accordance with the wizard included in the control software of the SPR evaluation device T200. For the immobilization of the noro antigen, the noro antigen was diluted with an acetic acid solution having a pH of 4.5 and was used at a concentration of 50 micrograms/milliliter. The acetic acid solution had a concentration of 1 microgram/milliliter.

Figure 3:
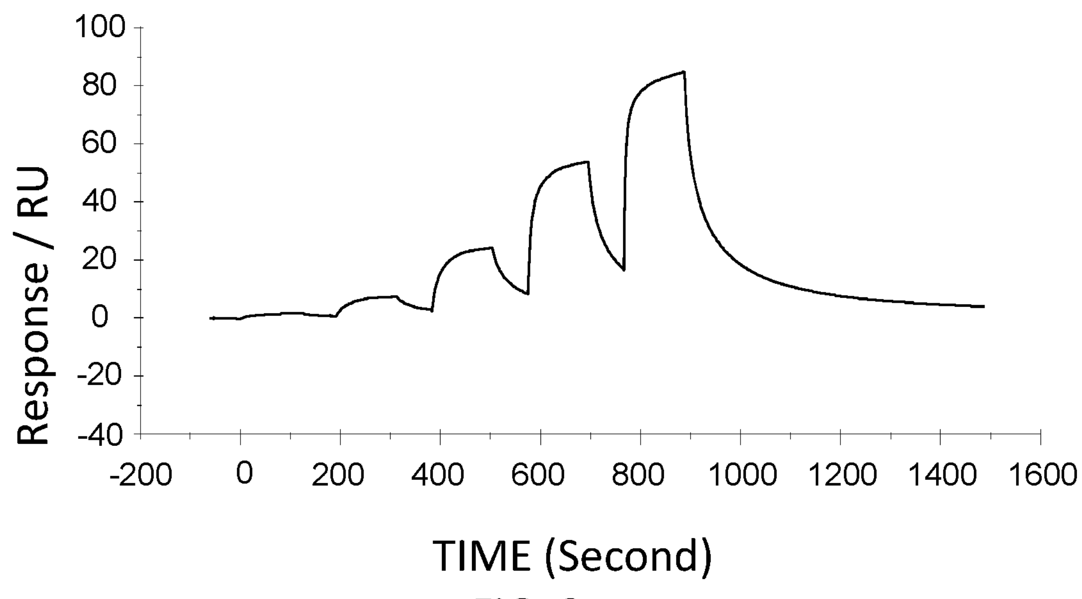
FIG. 3 is a graph showing a SPR evaluation result of the binding ability of the VHH antibody including the amino acid sequence represented by SEQ ID NO: 38 to a noro antigen, the SPR evaluation result being provided by serially adding the VHH antibodies prepared so as to have a concentration of 1.6 nM, 8 nM, 40 nM, 200 nM, and 1000 nM.
Figure 4:
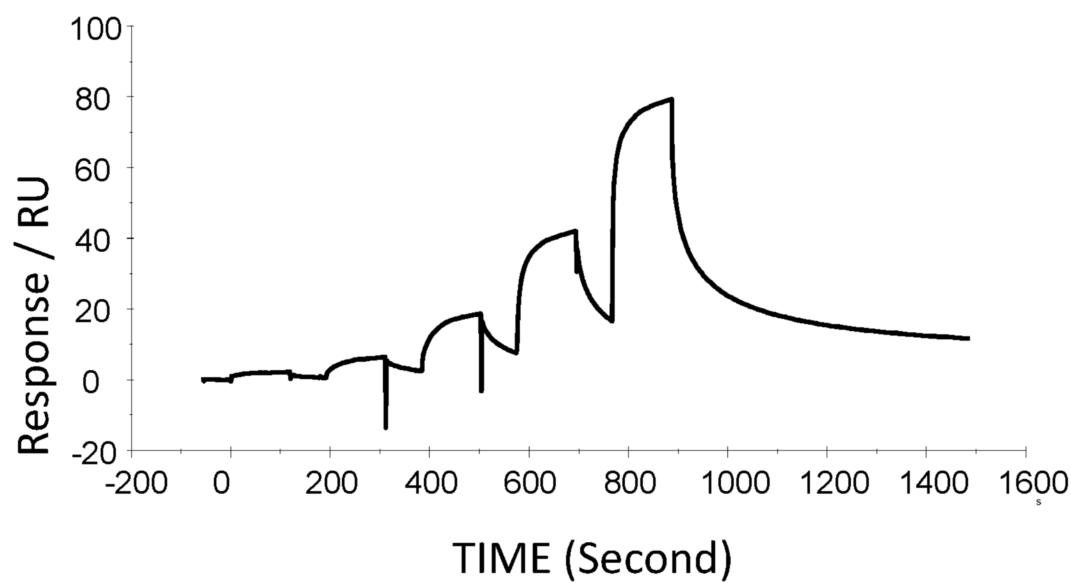
FIG. 4 is a graph showing a SPR evaluation result of the binding ability of the VHH antibody including the amino acid sequence represented by SEQ ID NO: 39 to a noro antigen, the SPR evaluation result being provided by serially adding the VHH antibodies prepared so as to have a concentration of 1.6 nM, 8 nM, 40 nM, 200 nM, and 1000 nM.
Figure 5:
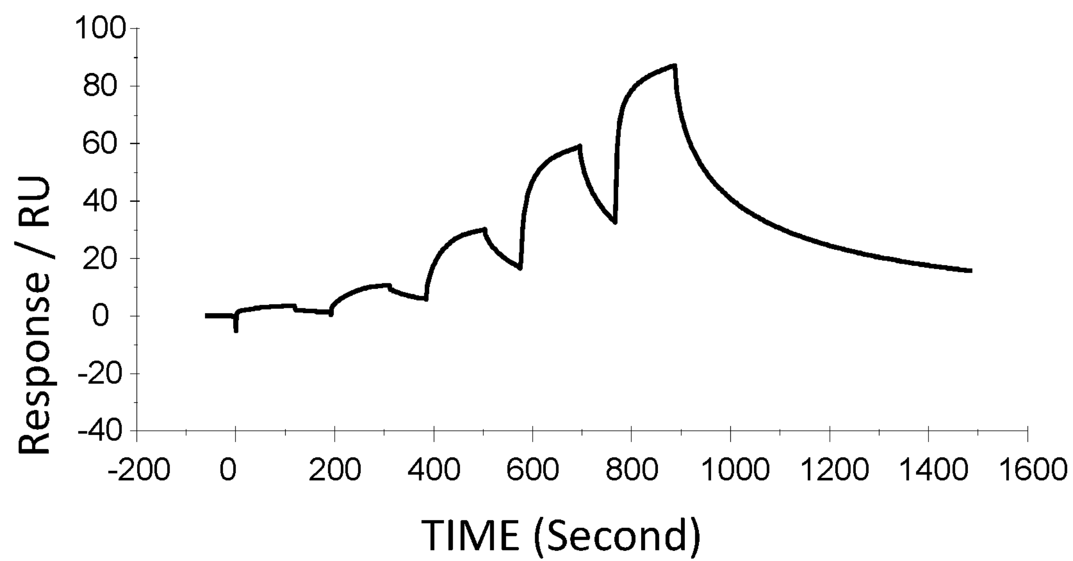
FIG. 5 is a graph showing a SPR evaluation result of the binding ability of the VHH antibody including the amino acid sequence represented by SEQ ID NO: 40 to a noro antigen, the SPR evaluation result being provided by serially adding the VHH antibodies prepared so as to have a concentration of 1.6 nM, 8 nM, 40 nM, 200 nM, and 1000 nM.
Figure 6A:
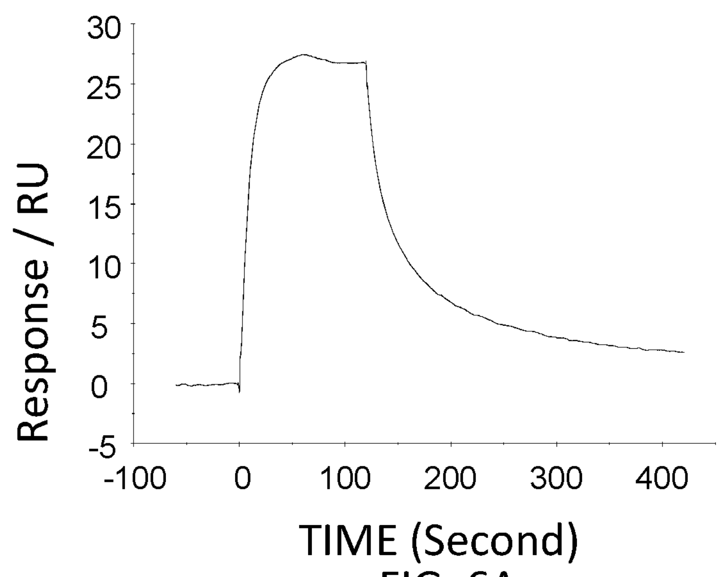
FIG. 6A is a graph showing the SPR evaluation result of the binding ability of the VHH antibody (concentration: 500 nM) including the amino acid sequence represented by SEQ ID NO: 41 to a norovirus.
Figure 6B:
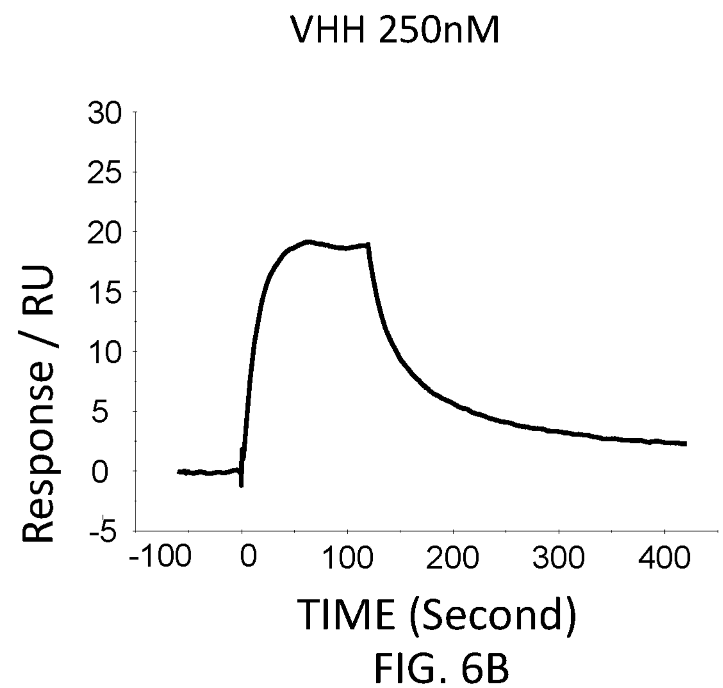
FIG. 6B is a graph showing the SPR evaluation result of the binding ability of the VHH antibody (concentration: 250 nM) including the amino acid sequence represented by SEQ ID NO: 41 to a norovirus.
Figure 6C:
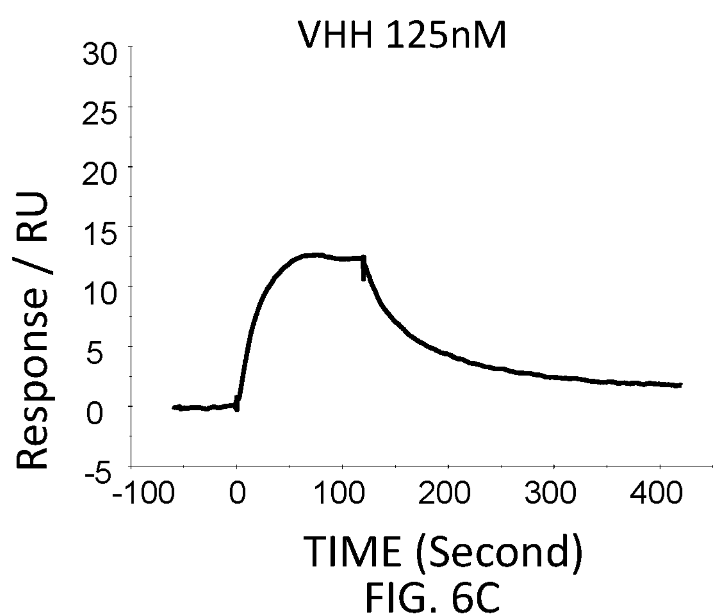
FIG. 6C is a graph showing the SPR evaluation result of the binding ability of the VHH antibody (concentration: 125 nM) including the amino acid sequence represented by SEQ ID NO: 41 to a norovirus.
Figure 6D:
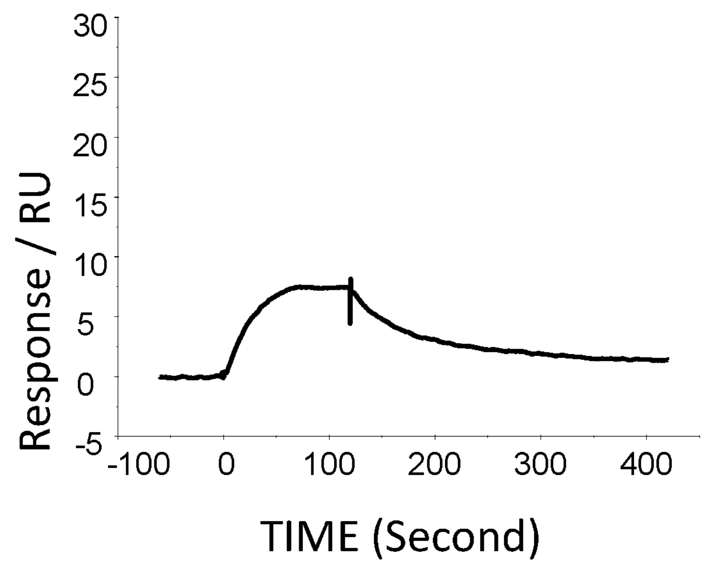
FIG. 6D is a graph showing the SPR evaluation result of the binding ability of the VHH antibody (concentration: 62.5 nM) including the amino acid sequence represented by SEQ ID NO: 41 to a norovirus
Figure 6E:
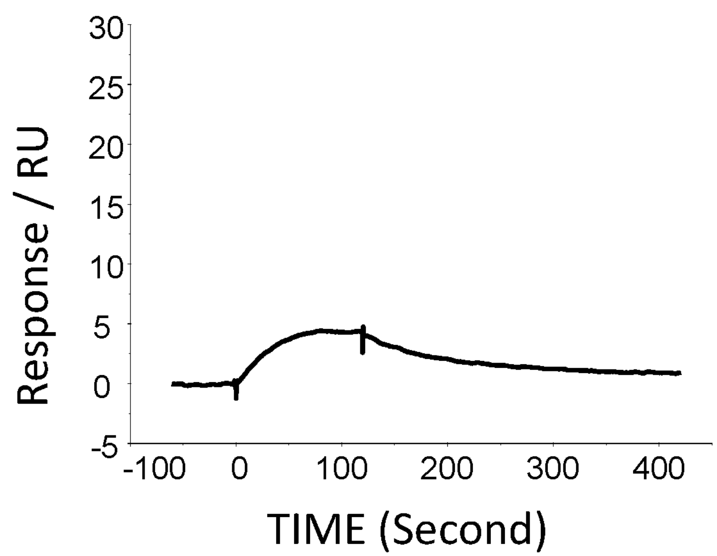
FIG. 6E is a graph showing the SPR evaluation result of the binding ability of the VHH antibody (concentration: 31.25 nM) including the amino acid sequence represented by SEQ ID NO: 41 to a norovirus.
Figure 6F:
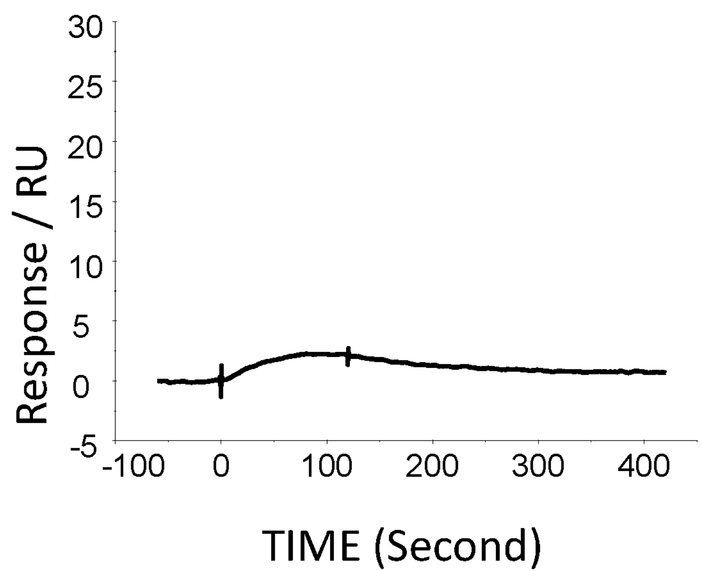
FIG. 6F is a graph showing the SPR evaluation result of the binding ability of the VHH antibody (concentration: 15.63 nM) including the amino acid sequence represented by SEQ ID NO: 41 to a norovirus.
Figure 6G:
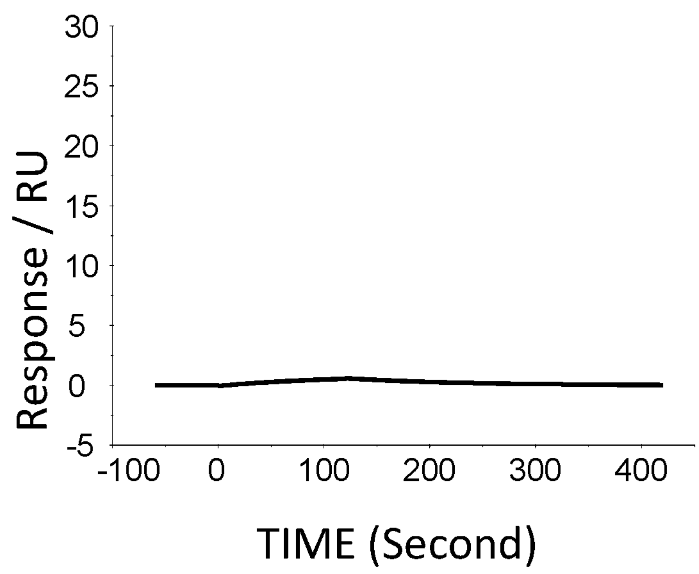
FIG. 6G is a graph showing the SPR evaluation result of the binding ability of the VHH antibody (concentration: 7.81 nM) including the amino acid sequence represented by SEQ ID NO: 41 to a norovirus
Figure 7A:
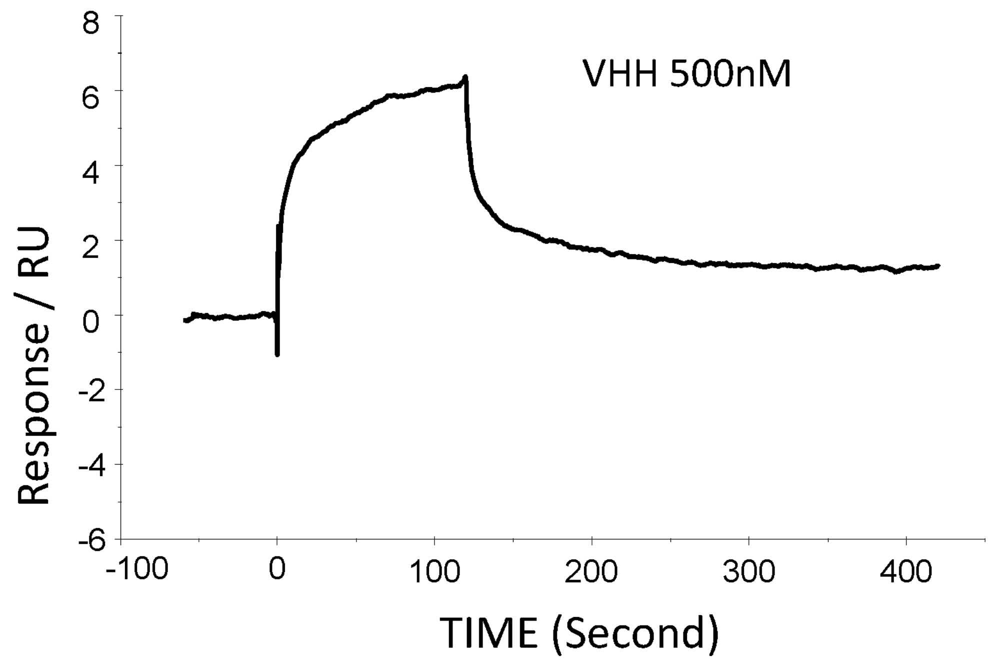
FIG. 7A is a graph showing the SPR evaluation result of the binding ability of the VHH antibody (concentration: 500 nM) including the amino acid sequence represented by SEQ ID NO: 42 to a norovirus.
Figure 7B:
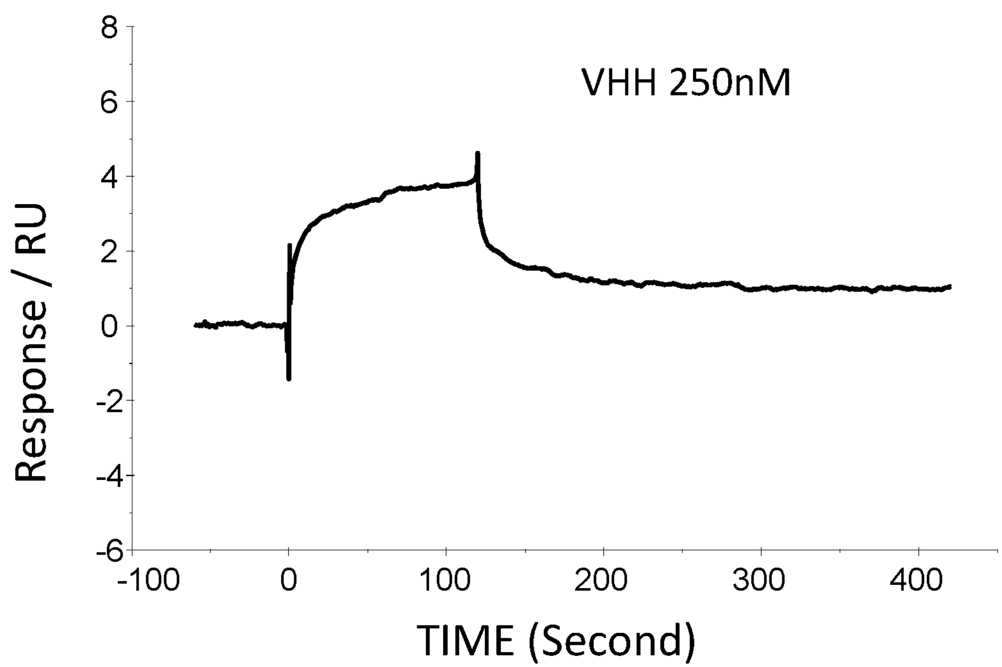
FIG. 7B is a graph showing the SPR evaluation result of the binding ability of the VHH antibody (concentration: 250 nM) including the amino acid sequence represented by SEQ ID NO: 42 to a norovirus.
Figure 7C:
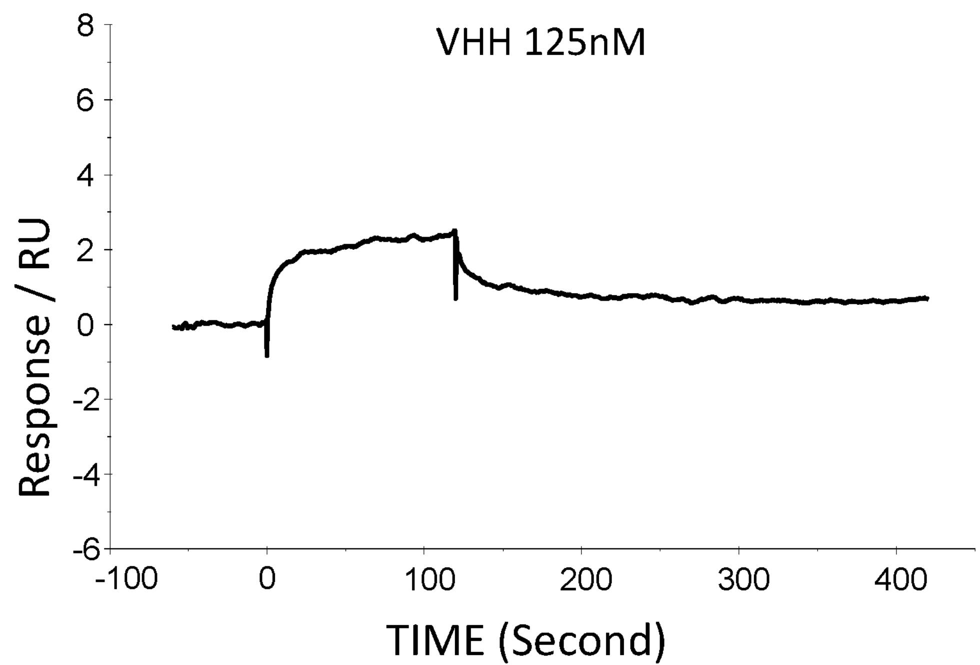
FIG. 7C is a graph showing the SPR evaluation result of the binding ability of the VHH antibody (concentration: 125 nM) including the amino acid sequence represented by SEQ ID NO: 42 to a norovirus.
Figure 7D:
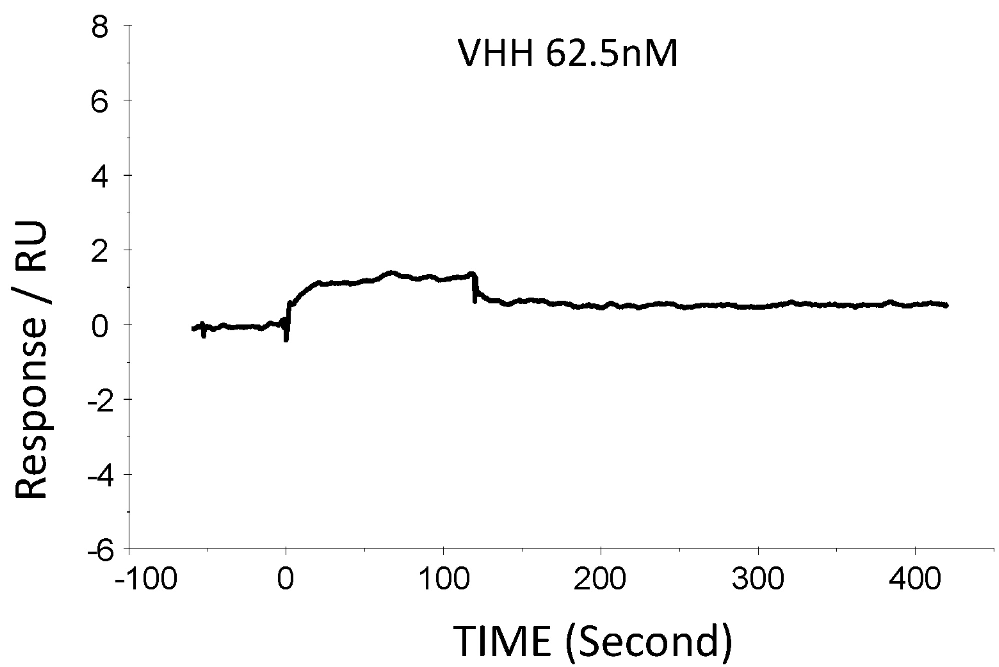
FIG. 7D is a graph showing the SPR evaluation result of the binding ability of the VHH antibody (concentration: 62.5 nM) including the amino acid sequence represented by SEQ ID NO: 42 to a norovirus
Figure 7E:
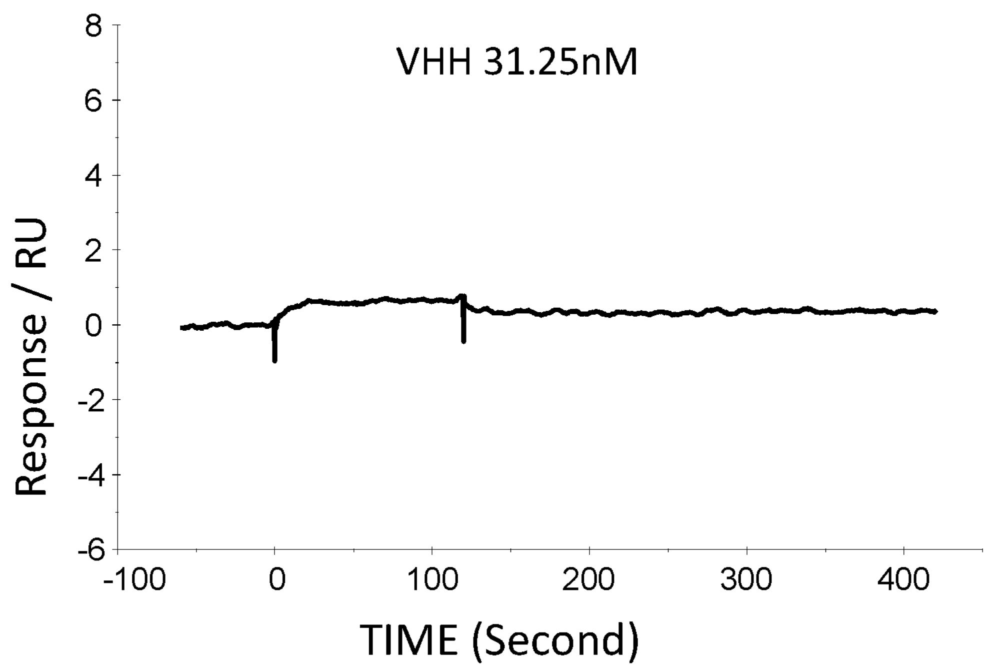
FIG. 7E is a graph showing the SPR evaluation result of the binding ability of the VHH antibody (concentration: 31.25 nM) including the amino acid sequence represented by SEQ ID NO: 42 to a norovirus.
Figure 7F:
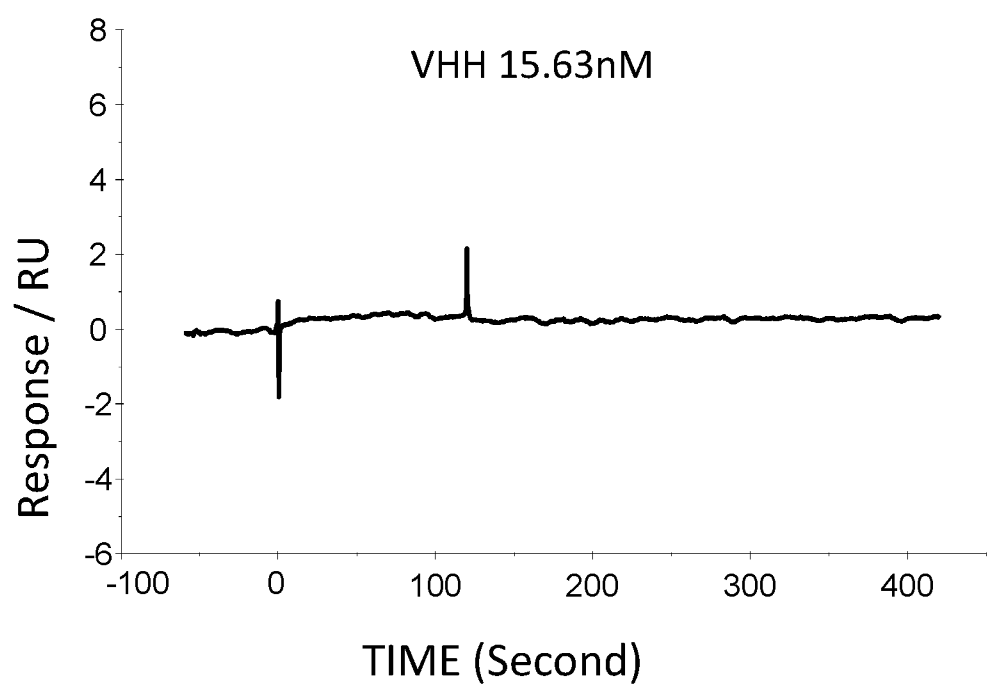
FIG. 7F is a graph showing the SPR evaluation result of the binding ability of the VHH antibody (concentration: 15.63 nM) including the amino acid sequence represented by SEQ ID NO: 42 to a norovirus.
Figure 7G:
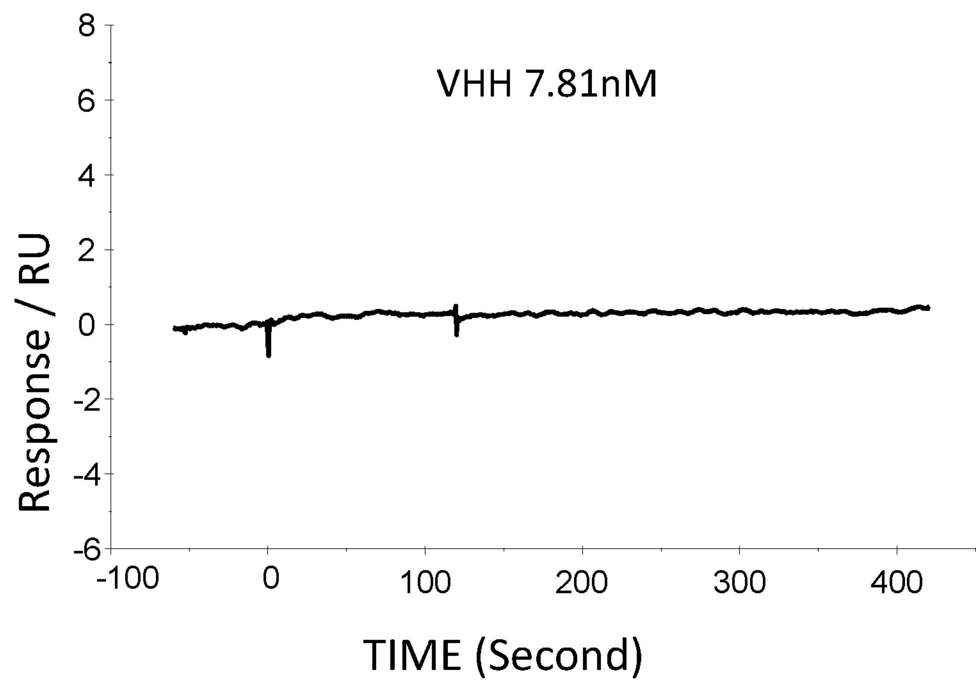
FIG. 7G is a graph showing the SPR evaluation result of the binding ability of the VHH antibody (concentration: 7.81 nM) including the amino acid sequence represented by SEQ ID NO: 42 to a norovirus.
Figure 7H:
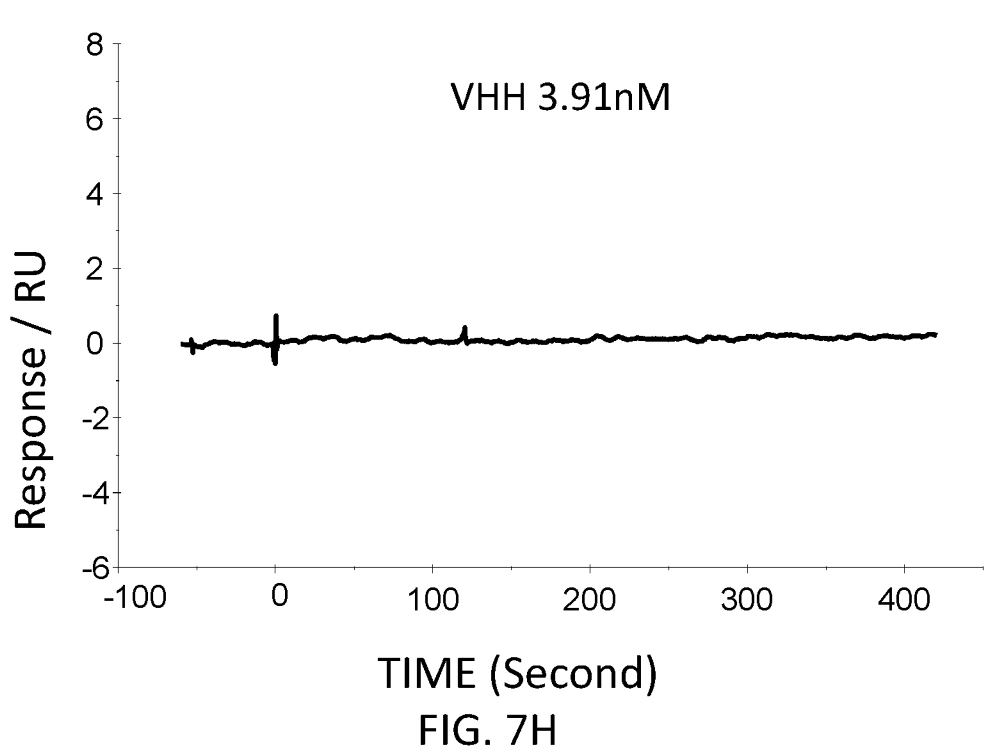
FIG. 7H is a graph showing the SPR evaluation result of the binding ability of the VHH antibody (concentration: 3.91 nM) including the amino acid sequence represented by SEQ ID NO: 42 to a norovirus.
Figure 8A:
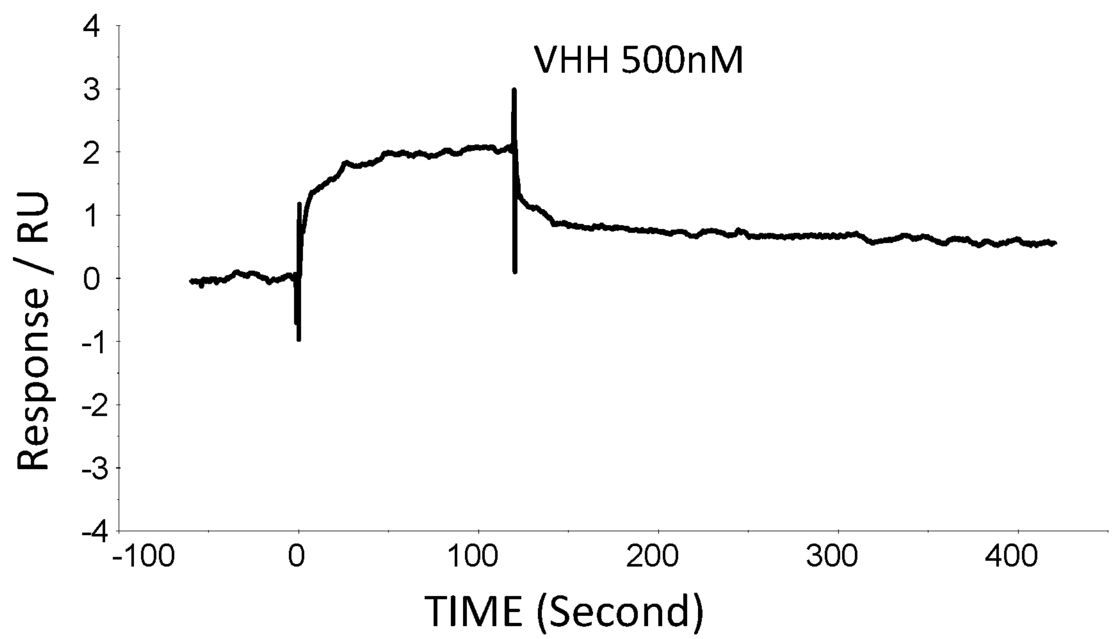
FIG. 8A is a graph showing the SPR evaluation result of the binding ability of the VHH antibody (concentration: 500 nM) including the amino acid sequence represented by SEQ ID NO: 43 to a norovirus.
Figure 8B:
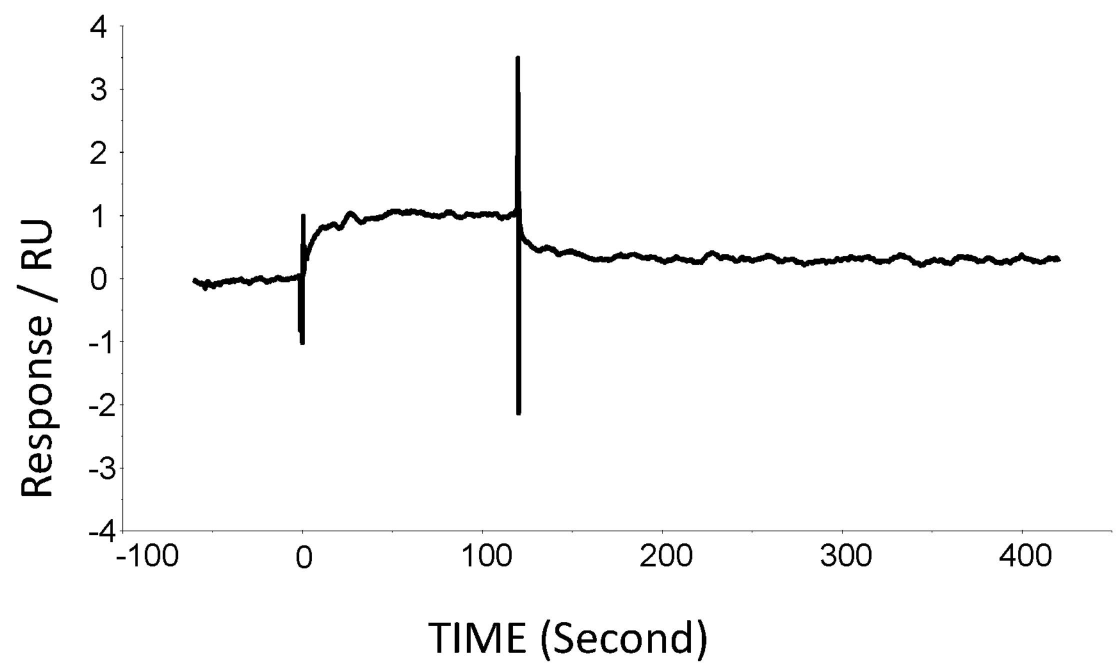
FIG. 8B is a graph showing the SPR evaluation result of the binding ability of the VHH antibody (concentration: 250 nM) including the amino acid sequence represented by SEQ ID NO: 43 to a norovirus.
Figure 8C:
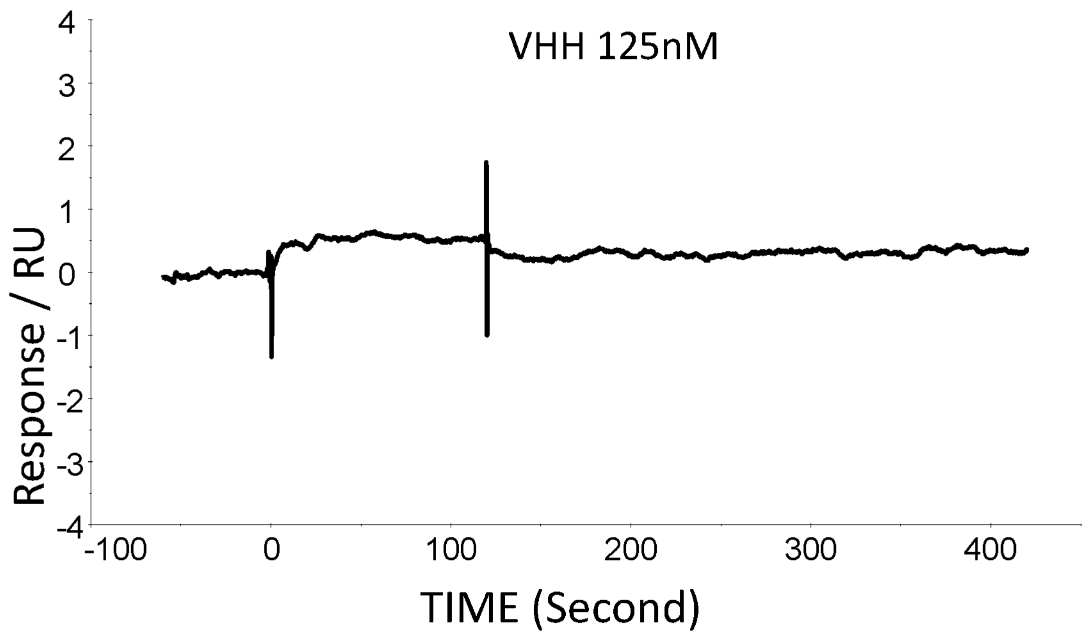
FIG. 8C is a graph showing the SPR evaluation result of the binding ability of the VHH antibody (concentration: 125 nM) including the amino acid sequence represented by SEQ ID NO: 43 to a norovirus.
Figure 8D:
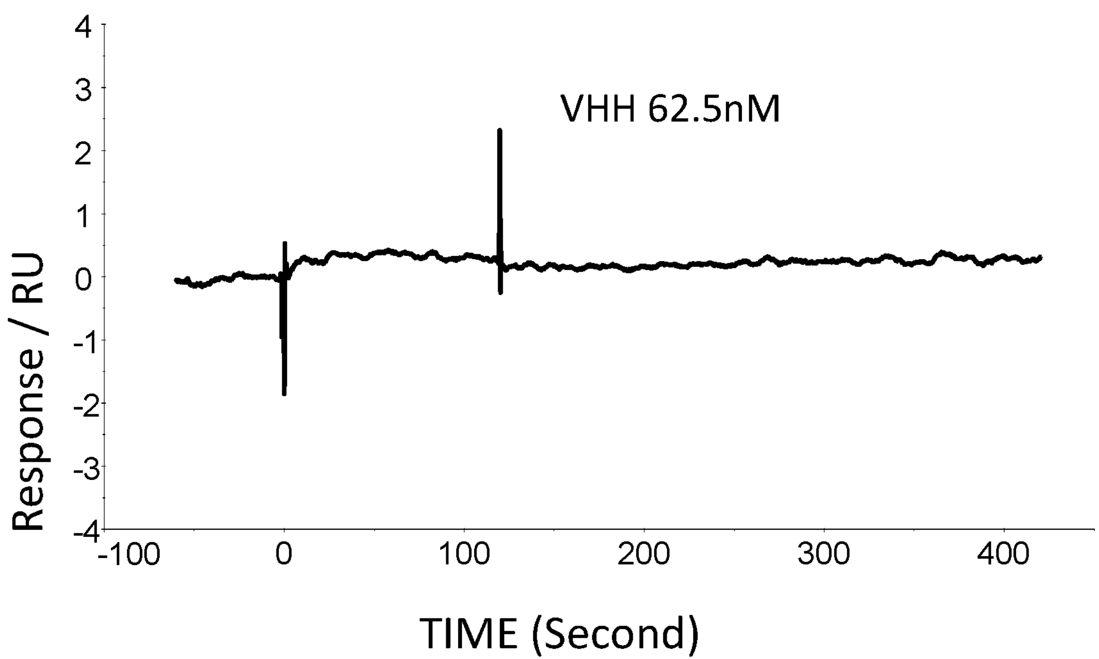
FIG. 8D is a graph showing the SPR evaluation result of the binding ability of the VHH antibody (concentration: 62.5 nM) including the amino acid sequence represented by SEQ ID NO: 43 to a norovirus.
Figure 8E:
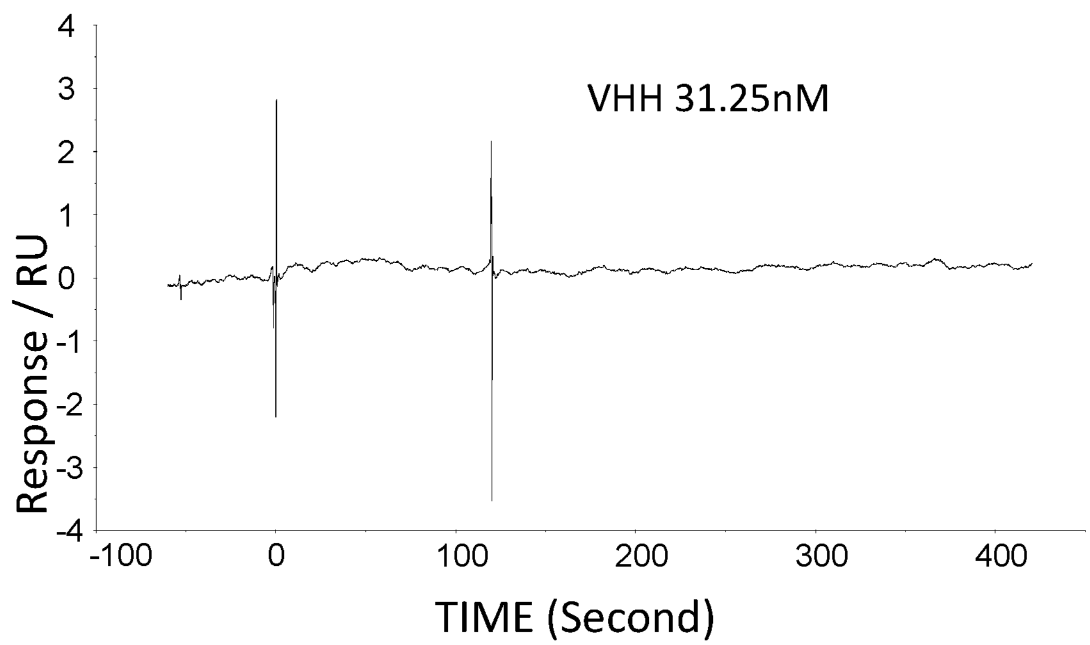
FIG. 8E is a graph showing the SPR evaluation result of the binding ability of the VHH antibody (concentration: 31.25 nM) including the amino acid sequence represented by SEQ ID NO: 43 to a norovirus.
Figure 8F:
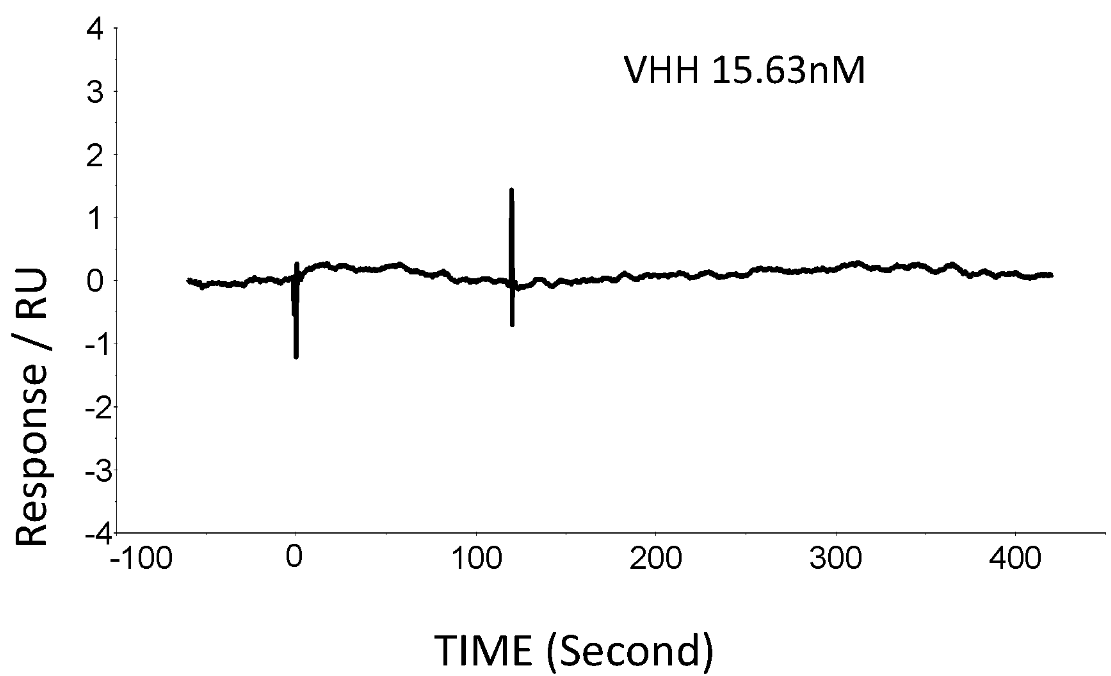
FIG. 8F is a graph showing the SPR evaluation result of the binding ability of the VHH antibody (concentration: 15.63 nM) including the amino acid sequence represented by SEQ ID NO: 43 to a norovirus.
Figure 8G:
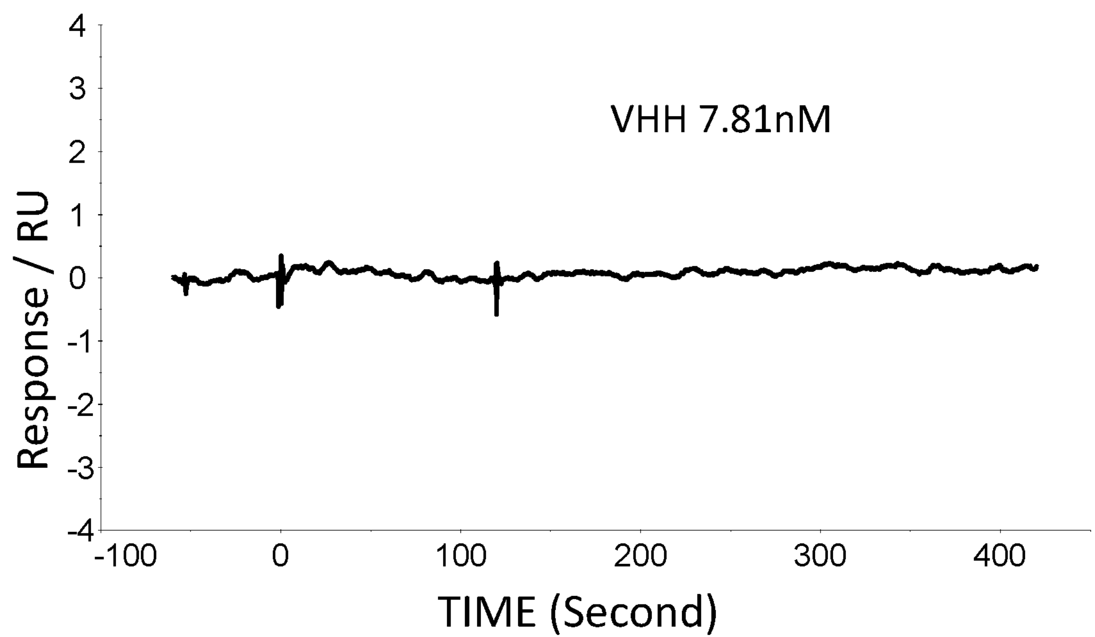
FIG. 8G is a graph showing the SPR evaluation result of the binding ability of the VHH antibody (concentration: 7.81 nM) including the amino acid sequence represented by SEQ ID NO: 43 to a norovirus.
Figure 8H:
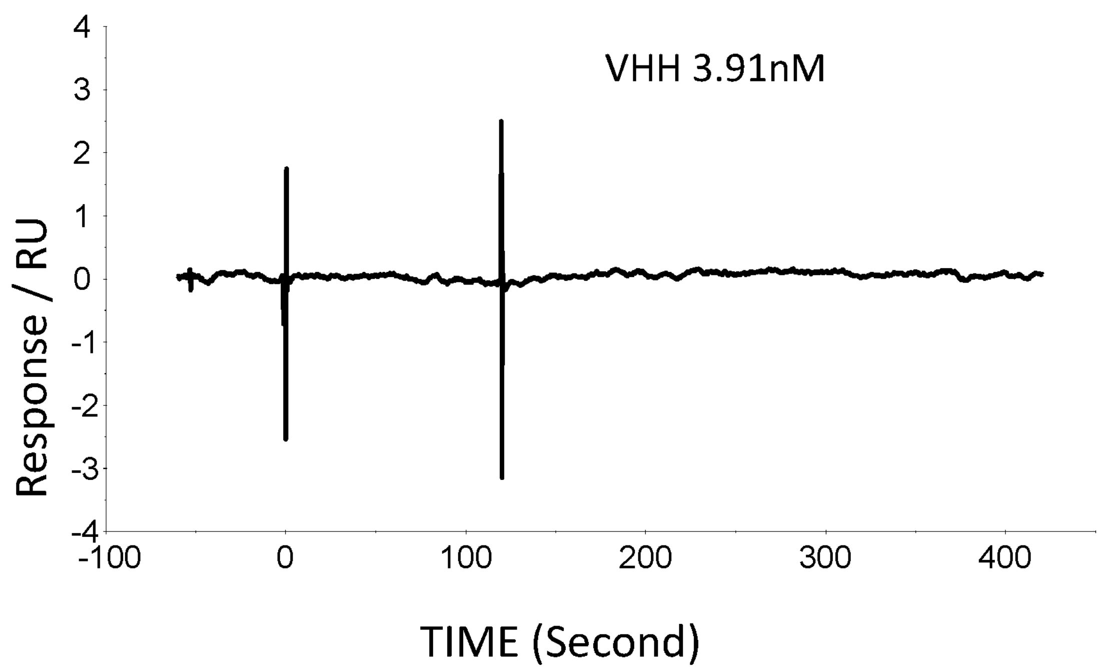
FIG. 8H is a graph showing the SPR evaluation result of the binding ability of the VHH antibody (concentration: 3.91 nM) including the amino acid sequence represented by SEQ ID NO: 43 to a norovirus.
Figure 9:
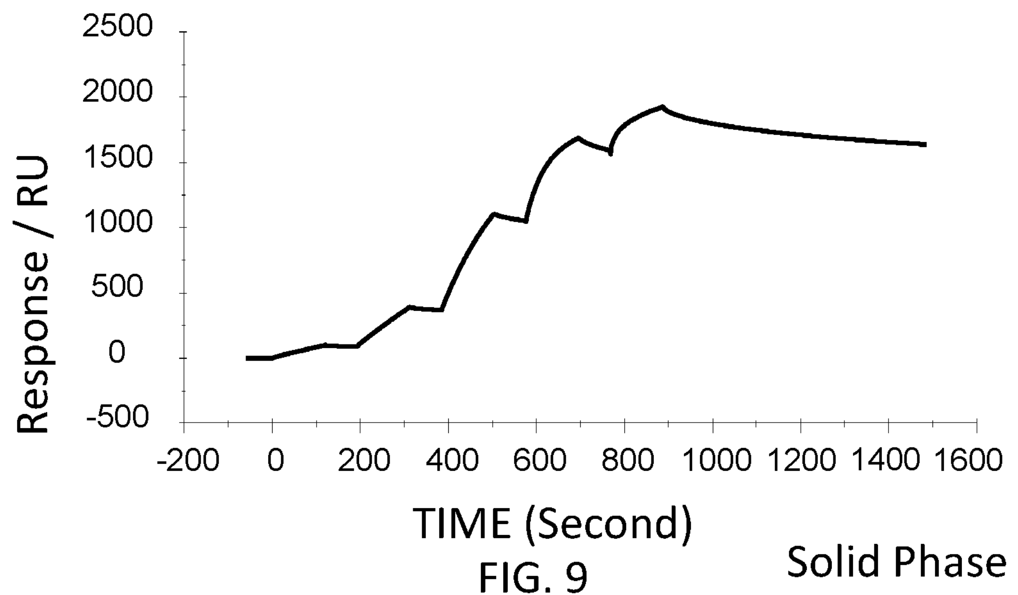
FIG. 9 is a graph showing a SPR evaluation result of the binding ability of the immobilized VHH antibody including the amino acid sequence represented by SEQ ID NO: 38 to a noro antigen, the SPR evaluation result being provided by serially adding the noro antigens prepared so as to have a concentration of 1.6 nM, 8 nM, 40 nM, 200 nM, and 1000 nM.
Figure 10:
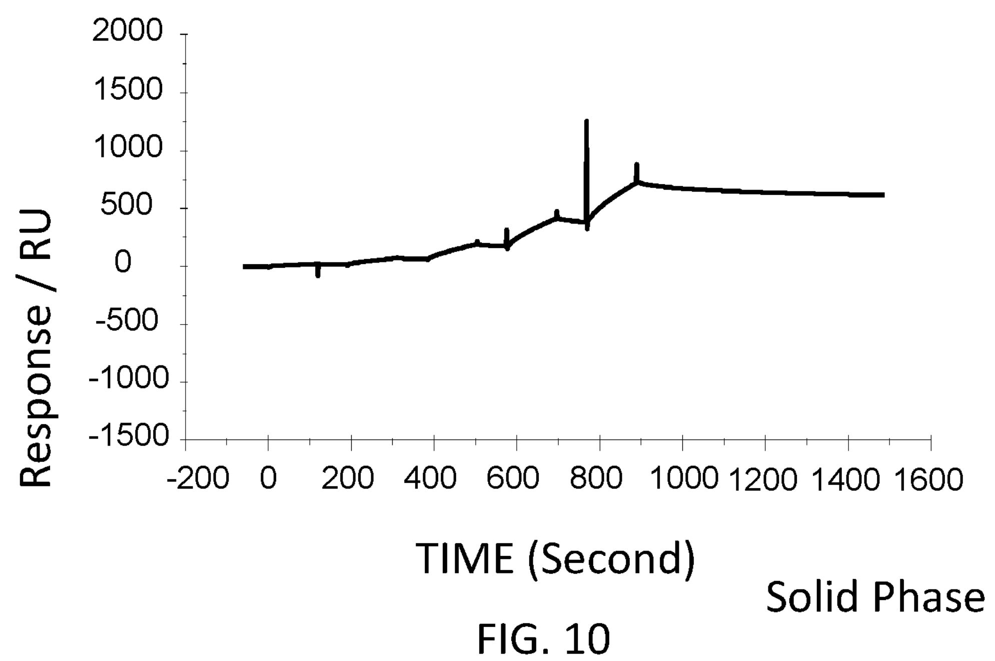
FIG. 10 is a graph showing a SPR evaluation result of the binding ability of the immobilized VHH antibody including the amino acid sequence represented by SEQ ID NO: 39 to a noro antigen, the SPR evaluation result being provided by serially adding the noro antigens prepared so as to have a concentration of 1.6 nM, 8 nM, 40 nM, 200 nM, and 1000 nM.
Figure 11:
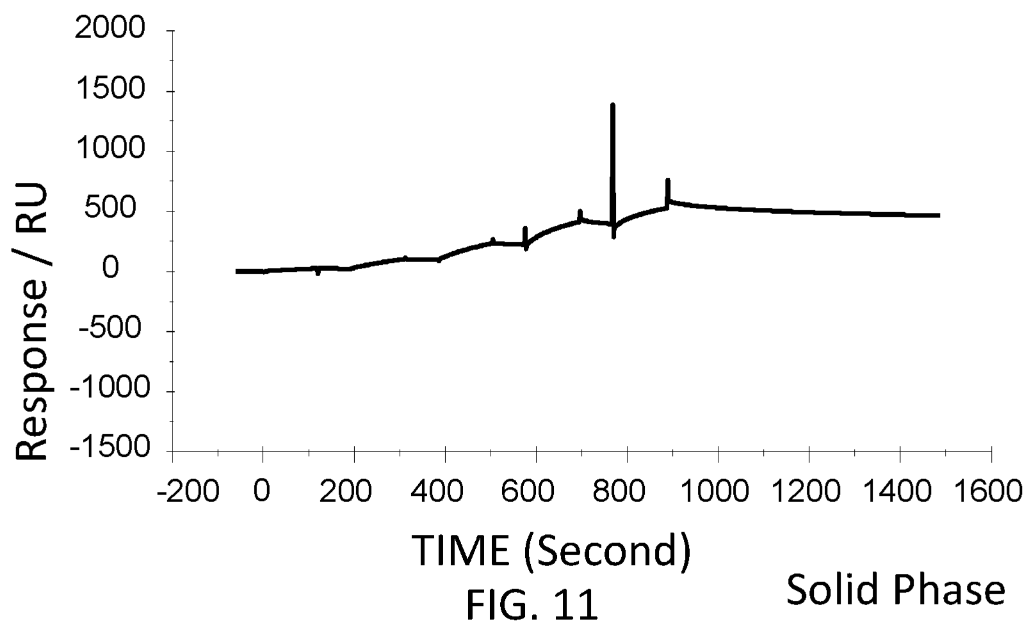
FIG. 11 is a graph showing a SPR evaluation result of the binding ability of the immobilized VHH antibody including the amino acid sequence represented by SEQ ID NO: 40 to a noro antigen, the SPR evaluation result being provided by serially adding the noro antigens prepared so as to have a concentration of 1.6 nM, 8 nM, 40 nM, 200 nM, and 1000 nM.
Figure 12:
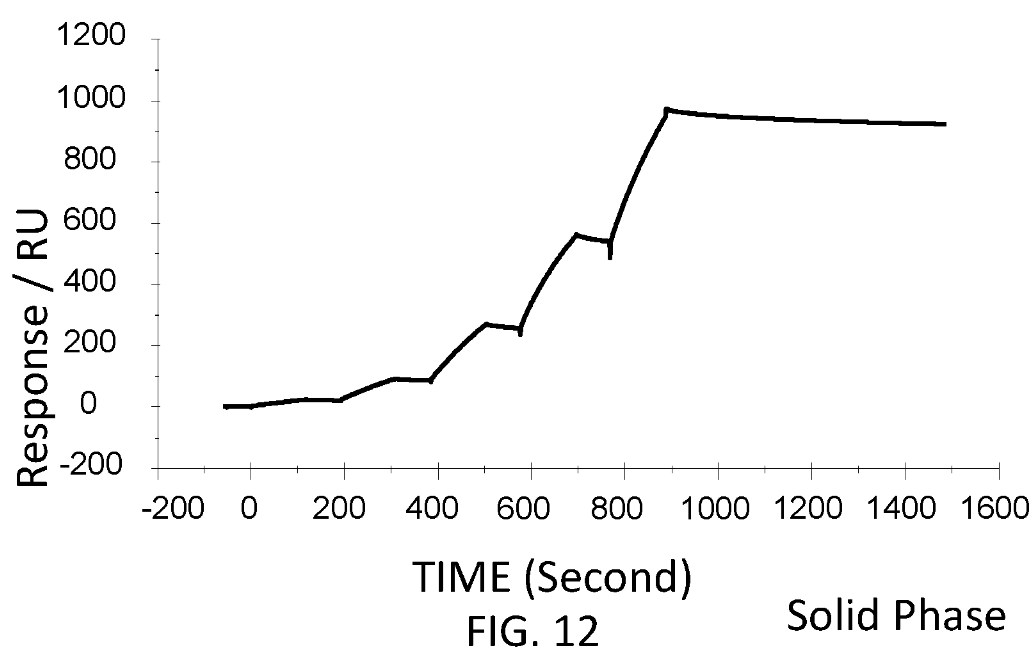
FIG. 12 is a graph showing a SPR evaluation result of the binding ability of the immobilized VHH antibody including the amino acid sequence represented by SEQ ID NO: 41 to a noro antigen, the SPR evaluation result being provided by serially adding the noro antigens prepared so as to have a concentration of 1.6 nM, 8 nM, 40 nM, 200 nM, and 1000 nM.
Figure 13:
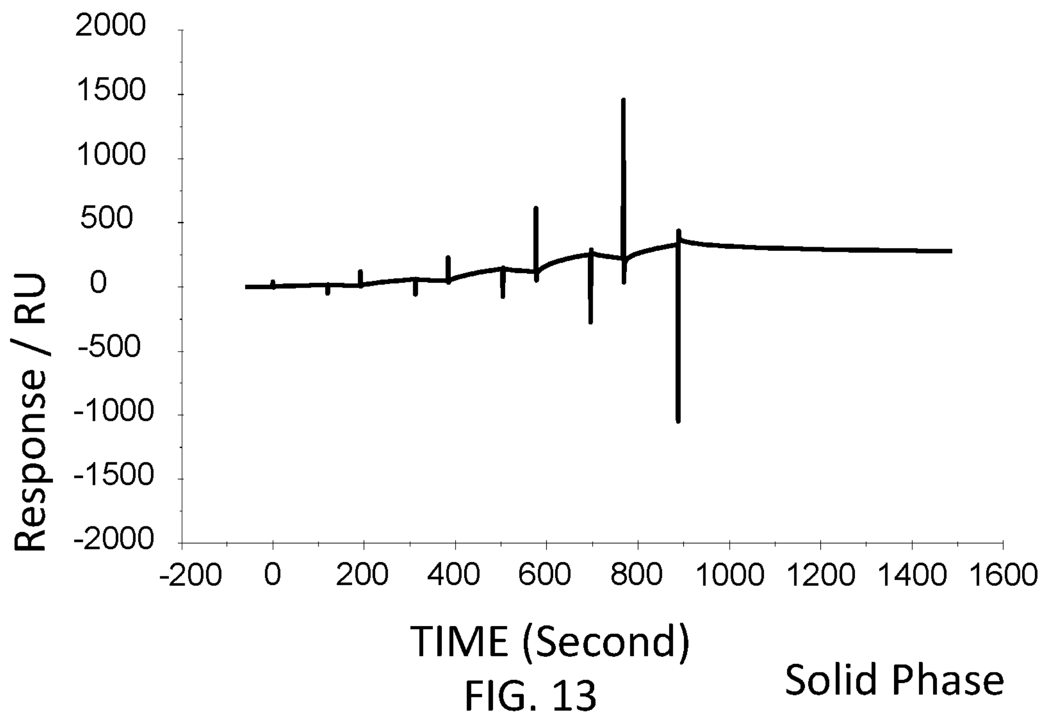
FIG. 13 is a graph showing a SPR evaluation result of the binding ability of the immobilized VHH antibody including the amino acid sequence represented by SEQ ID NO: 42 to a noro antigen, the SPR evaluation result being provided by serially adding the noro antigens prepared so as to have a concentration of 1.6 nM, 8 nM, 40 nM, 200 nM, and 1000 nM.
Figure 14:
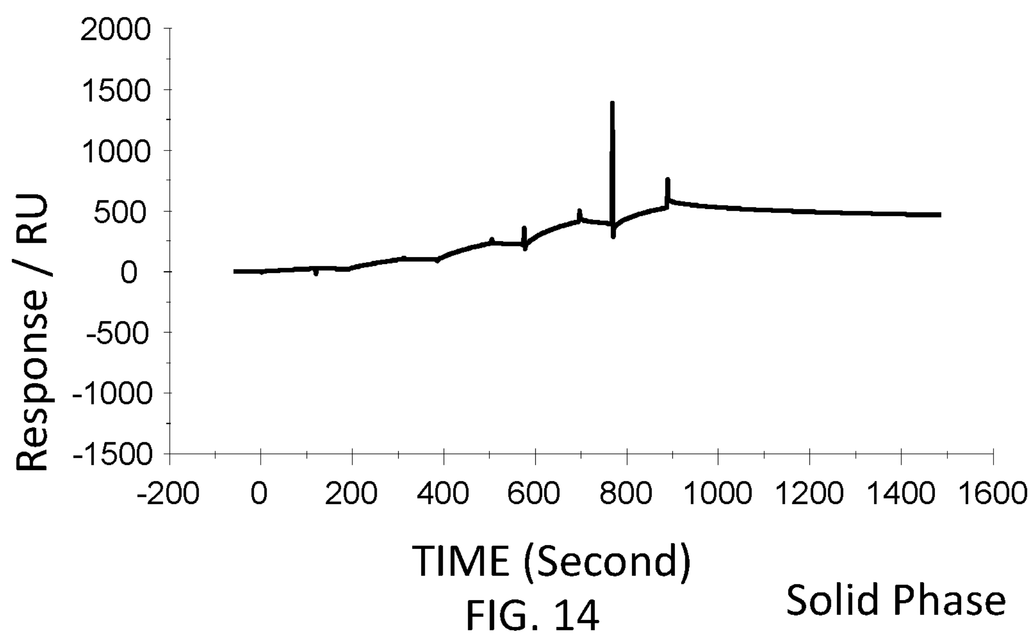
FIG. 14 is a graph showing a SPR evaluation result of the binding ability of the immobilized VHH antibody including the amino acid sequence represented by SEQ ID NO: 43 to a noro antigen, the SPR evaluation result being provided by serially adding the noro antigens prepared so as to have a concentration of 1.6 nM, 8 nM, 40 nM, 200 nM, and 1000 nM.

The VHH antibodies including the amino acid sequences represented by SEQ ID NO: 38-SEQ ID NO: 40 were used as analytes. The concentrations of the VHH antibodies contained in the running buffer were adjusted to 1.6 nM, 8 nM, 40 nM, 200 nM, and 1,000 nM. Then, the VHH antibodies were added serially. FIG. 3-FIG. 5 are graphs each showing evaluation result provided from the SPR evaluation device T200. The dissociation constant Kd was calculated using the evaluation software (available from GE Healthcare). As a result, the dissociation constants Kd were 1.15 nM, 15.8 nM, and 9.5 nM.

The anti-noro antibodies including the amino acid sequence represented by SEQ ID NO: 41-SEQ ID NO: 43 were used as analytes. In the first-eighth analysis, the concentrations of the anti-noro antibodies contained in the running buffer were adjusted to 500 nM, 250 nM, 125 nM, 62.5 nM, 31.25 nM, 15.63 nM, 7.81 nM, and 3.91 nM. FIG. 6A-FIG. 8H are graphs each showing evaluation result provided from the SPR evaluation device T200. The dissociation constant Kd was calculated using the evaluation software (available from GE Healthcare). As a result, the dissociation constants Kd were 81.6 nM, 63.8 nM, and 5.45 nM.

Next, the VHH antibodies (SEQ ID NO: 66-SEQ ID NO: 71) were immobilized to evaluate the binding to the noro antigen. The VHH antibodies were immobilized in accordance with the wizard included in the control software of the SPR evaluation device T200. For the immobilization of the VHH antibodies, the VHH antibodies was diluted with an acetic acid solution having a pH of 5.5 and was used at a concentration of 50 micrograms/milliliter. The acetic acid solution had a concentration of 1 microgram/milliliter. The noro antigen was used as an analyte. The concentrations of the VHH antibodies contained in the running buffers were adjusted to 10 nM, 31.6 nM, 100 nM, 316 nM, and 1,000 nM. The running buffers were added serially. FIG. 9-FIG. 14 are graphs each showing evaluation result provided from the SPR evaluation device T200. The dissociation constant Kd was calculated using the evaluation software (available from GE Healthcare). As a result, the dissociation constants Kd were 4.15 nM, 15.9 nM, 9.57 nM, 4.98 nM, 13.1 nM, and 10.3 nM.

Inventive Example 2

(Production of Antibody Bound to Protein)

An antibody bound to the protein in which the structural domain having the amino acid sequence represented by SEQ ID NO: 38 and the protein molecule having the amino acid sequence represented by SEQ ID NO: 44 were linked with a linker GGGGSGGGASGGGS (SEQ ID NO: 93) was provided. In particular, using the following two primers represented by SEQ ID NO: 95 and SEQ ID NO: 96 and DNA polymerase, by a PCR method, DNA fragments having restriction enzyme sites NheI at 3'-terminal end of the base sequence represented by SEQ ID NO: 64 and at 5'-terminal end of the base sequence represented by SEQ ID NO: 65 were provided. In addition, similarly to the production of the monomer antibody, using a primer, restriction enzyme SfiI recognition portions were added at the 5'-end terminal of the base sequence represented by SEQ ID NO: 64 and at the 3'-end terminal of the base sequence represented by SEQ ID NO: 65.

```
Primer 1:
                                      (SEQ ID NO: 95)
5'-aaaaGCTAGCGGTGGTGGTGGATCCsagktgcagacgtggagtc-3'

Primer 2:
                                      (SEQ ID NO: 96)
5'-caggtcacygtacctcaGGTGGTGGTGGTTCTGGTGGTGGTGCTAGC
aaaa-3'
```

Figure 15:
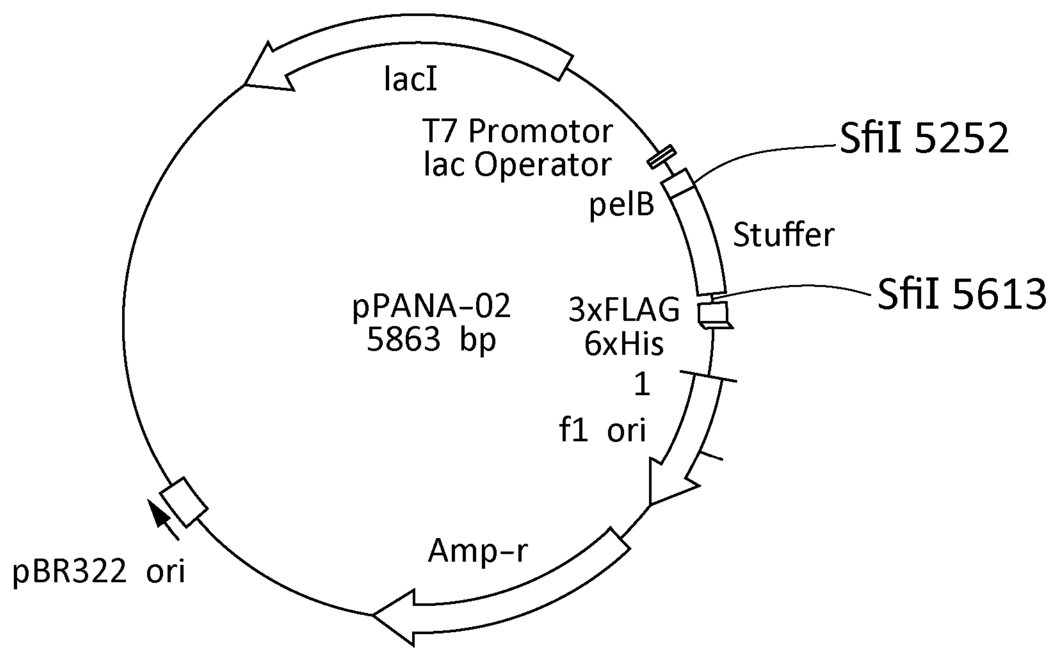
FIG. 15 is a detailed map of a vector used to ligate a gene coding for antibody bound to a protein.

A DNA sequence in which the DNA sequence coding for the structural domain and the protein molecule were linked with a linker was provided through NheI digestion and ligation. The thus-provided DNA sequence was digested with SfiI, and then, incorporated into the plasmid vector shown in FIG. 15. Coli bacteria were transfected with the thus-provided plasmid vector to produce an antibody bound to the protein. The antibody bound to the protein had the amino acid sequence represented by SEQ ID NO: 38 and the amino acid sequence represented by SEQ ID NO: 44. The amino acid sequence of the antibody bound to the protein is represented by SEQ ID NO: 100. Similarly, the antibodies each bound to the protein were provided. The one is represented by SEQ ID NO: 101, whereas the other is represented by SEQ ID NO: 102. In the antibody represented by SEQ ID NO: 101, in a direction from N to C, the protein molecule having the amino acid sequence represented by SEQ ID NO: 44 and the structural domain having the amino acid sequence represented by SEQ ID NO: 38 were connected with a linker. In the antibody represented by SEQ ID NO: 102, in a direction from N to C, the protein molecule having the amino acid sequence represented by SEQ ID NO: 44 and the structural domain having the amino acid sequence represented by SEQ ID NO: 39 were connected with a linker.

Figure 16:
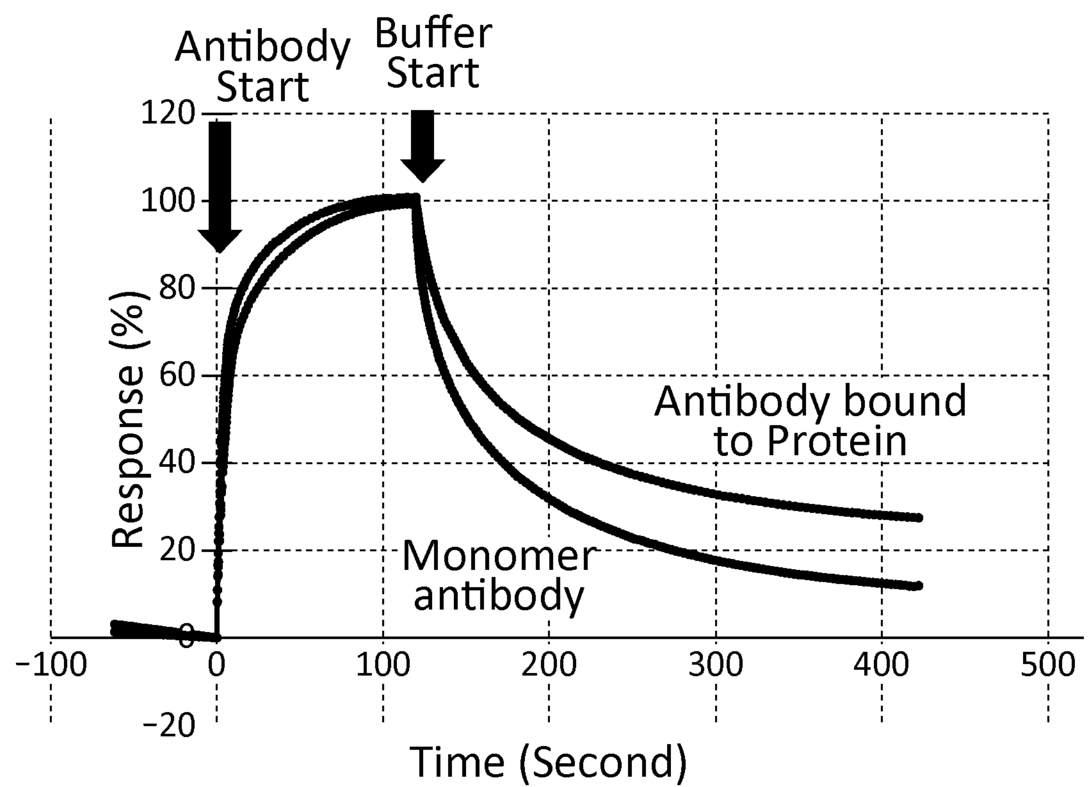
FIG. 16 is a graph showing a SPR evaluation result of the binding ability of the VHH antibody including the amino acid sequence represented by SEQ ID NO: 66 (i.e., a monomer antibody) and the VHH antibody including the amino acid sequence represented by SEQ ID NO: 100 (i.e., the antibody bound to the protein), each of the concentration of the VHH antibodies being 500 nM.

The antibody having the amino acid sequence represented by SEQ ID NO: 100 exhibited a higher binding ability to the norovirus than the VHH antibody having the amino acid sequence represented by SEQ ID NO: 66, which is a monomer antibody (FIG. 16).

(Surface Plasmon Resonance Evaluation of VHH Antibody Using VLP Noro Antigen

The VHH antibody was evaluated as below using the noro antigen and the surface plasmon resonance evaluation device. The details of the surface plasmon resonance (namely, "SPR") will be described below.

SPR evaluation device: T200 (available from GE Healthcare)

Immobilization buffer: HBS-EP+(available from GE Healthcare)

Running buffer: HBS-EP+(available from GE Healthcare)

Sensor chip: CM3 (available from GE Healthcare)

Immobilization reagents: N-hydroxysuccinimide (NHS) and N-[3-(dimethylamino)propyl]-N'-ethylcarbodiimide (EDC)

Noro Antigen

The VLP noro antigen was derived from the norovirus GII/4 composed by associating 90 dimers of VP1 each including the noro antigen (SEQ ID NO: 48).

The VLP noro antigen was immobilized in accordance with the wizard included in the control software of the SPR evaluation device T200. For the immobilization of the VLP noro antigen, the VLP noro antigen was diluted with an acetic acid solution having a pH of 4.0 and was used at a concentration of 25 micrograms/milliliter. The acetic acid solution had a concentration of 1 microgram/milliliter.

Figure 17:
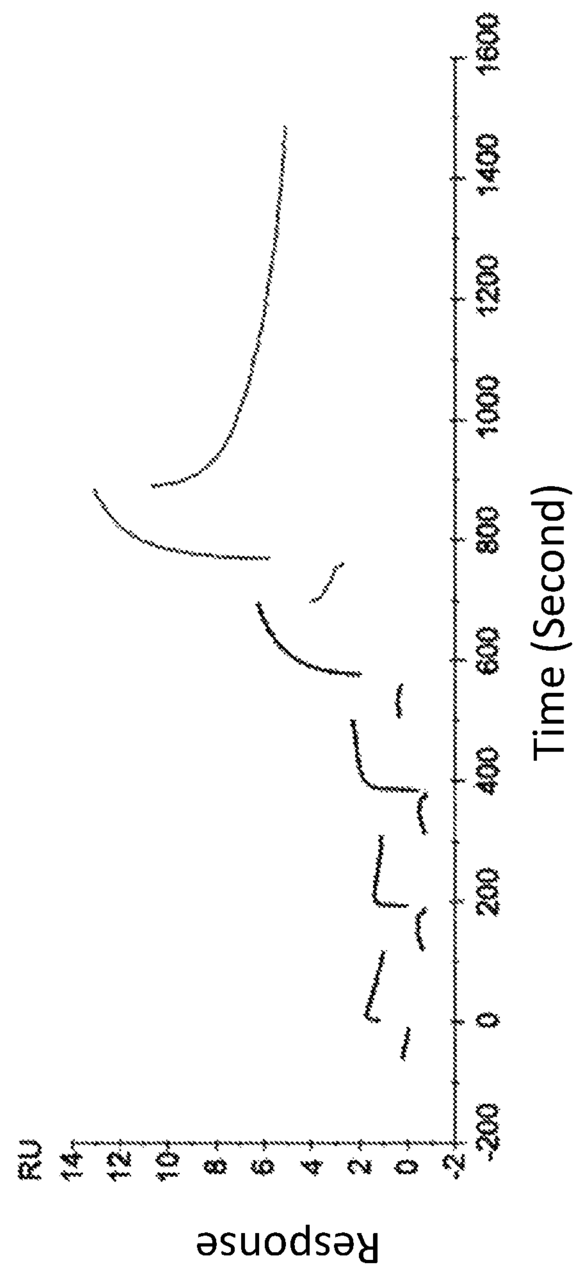
FIG. 17 is a graph showing a SPR evaluation result of the binding ability of the immobilized VHH antibody including the amino acid sequence represented by SEQ ID NO: 100 to a noro antigen, the SPR evaluation result being provided by serially adding the noro antigens prepared so as to have a concentration of 0.16 nM, 0.8 nM, 4 nM, 20 nM, and 100 nM.

The antibody bound to the protein was used as an analytes. The antibody bound to the protein had the amino acid sequences represented by SEQ ID NO: 100. The concentration of the antibody bound to the protein contained in the running buffer was adjusted to 0.16 nM, 0.8 nM, 4 nM, 20 nM, and 100 nM. Then, the antibody bound to the protein was added serially. FIG. 17 is a graph showing evaluation result provided from the SPR evaluation device T200. The dissociation constant Kd was calculated using the evaluation software (available from GE Healthcare). With regard to the antibody (i.e., the antibody bound to the protein) having the amino acid sequence represented by SEQ ID NO: 102 was also used as an analytes. With regard to the amino acid sequences represented by SEQ ID NO: 102, the dissociation constant Kd was calculated similarly. The results thereof are shown in the following Table 1 and FIG. 17. In Table 1, data of the monomer antibodies represented by SEQ ID NO: 66 and SEQ ID NO: 67 are also shown. The monomer antibodies represented by SEQ ID NO: 66 and SEQ ID NO: 67 are included, as the structural domains thereof, in the antibodies (i.e., the antibodies each bound to the protein) having the amino acid sequences represented by SEQ ID NO: 100 and SEQ ID NO: 102, respectively.

TABLE 1

| Kind | SEQ ID NO: | Interaction with the solid phase VLP Ka(1/Ms) | kd (1/s) | Kd (M) |
|---|---|---|---|---|
| Antibody bound to Protein | 100 | 2.930E+06 | 6.985E−03 | 2.384E−09 |
| Monomer Antibody | 66 | 1.443E+05 | 2.144E−02 | 1.486E−07 |
| Antibody bound to Protein | 102 | 1.066E+06 | 1.090E−02 | 1.022E−08 |
| Monomer Antibody | 67 | 3.541E+04 | 1.940E−02 | 5.479E−08 |

As shown above, the antibody bound to the protein exhibited lower dissociation constant Kd than the monomer antibody. This means that the antibody bound to the protein has a stronger binding ability to the norovirus than the monomer antibody.

Figure 18:
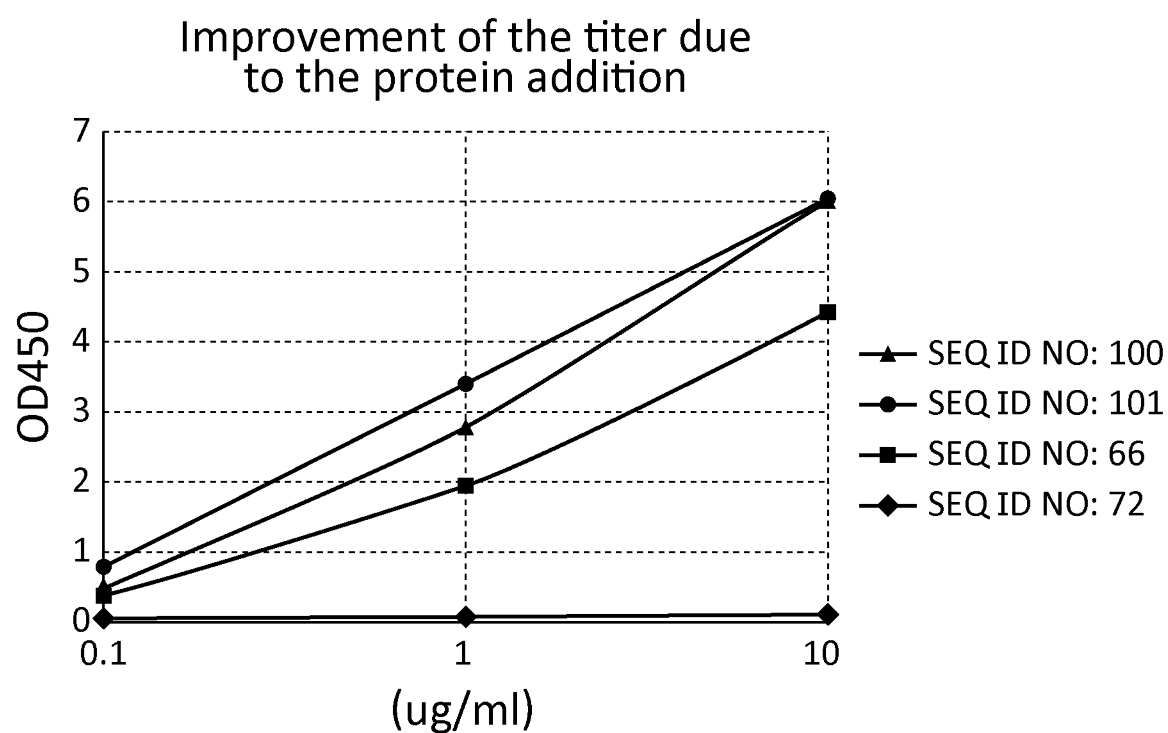
FIG. 18 is a graph showing result provided by measuring the binding ability of the antibodies (SEQ ID NO: 66, SEQ ID NO: 72, SEQ ID NO: 100, and SEQ ID NO: 101) including the amino acid sequences represented by SEQ ID NO: 38, SEQ ID NO: 44, SEQ ID NO: 45, and SEQ ID NO: 46 to a norovirus by an ELISA method, respectively.

The present inventors evaluated the binding ability of the monomer antibodies represented by SEQ ID NO: 66, SEQ ID NO: 72 and the antibodies (i.e., antibodies each bound to the protein) represented by SEQ ID NO: 100 and SEQ ID NO: 101 to the norovirus by an ELISA method in which GII/4 Frag 4 (2 micrograms/milliliter, in PBS) and skim milk (concentration: 3% in PBST) were used as a solid phase and a blocking solution, respectively. The results are shown in FIG. 18. It was proved that the antibodies each bound to the protein had a higher binding ability to the norovirus than the monomer antibodies.

The invention claimed is:

1. An antibody comprising a structural domain represented by the following amino acid sequence, in an N- to C-direction,

N-FR1-CDR1-FR2-CDR2-FR3-CDR3-FR4-C wherein the antibody further comprises a protein molecule bound to the structural domain, the structural domain is capable of binding to a norovirus, the norovirus is a GII/4 norovirus, FR denotes a framework region amino acid sequence and CDR denotes a complementary determining region amino acid sequence, the CDR1 comprises any one of the amino acid sequence represented by SEQ ID NO: 1-SEQ ID NO: 6, the CDR2 comprises any one of the amino acid sequence represented by SEQ ID NO: 7-SEQ ID NO: 13, and the CDR3 comprises any one of the amino acid sequence represented by SEQ ID NO: 13-SEQ ID NO: 17.

2. The antibody bound to the protein according to claim 1, wherein the FR1 comprises any one of the amino acid sequences represented by SEQ ID NO: 18-SEQ ID NO: 23, the FR2 comprises any one of the amino acid sequences represented by SEQ ID NO: 24-SEQ ID NO: 28, the FR3 comprises the amino acid sequences represented by SEQ ID NO: 29-SEQ ID NO: 34, and the FR4 comprises any one of the amino acid sequences represented by SEQ ID NO: 35-SEQ ID NO: 37.

3. The antibody according to claim 1, wherein the structural domains is linked with an amino acid linker comprising the sequence represented by GGGGS (SEQ ID NO: 91) and having a 5-60 amino acid sequence length.

4. The antibody according to claim 1, wherein the protein molecule is a VHH antibody which is not capable of binding to the norovirus.

5. A composite, containing:

an antibody bound to the protein according to claim 1;

wherein the antibody bound to the protein is bound to at least one selected from the group consisting of a solid phase support and a labeled substance.

6. The composite according to claim 5, wherein the antibody bound to the protein is bound to the solid phase support; and the solid phase support is selected from the group consisting of a plate, a bead, a disk, a tube, a filter, and a film.

7. The composite according to claim 5, wherein the antibody is bound to the labeled substance; and the labeled substance is selected from the group consisting of a fluorescent substance, a luminescent substance, a dye, an enzyme, and a radioactive substance.

8. A detection device comprising:

a composite according to claim 5; and a detector;

wherein the detector detects a change of a physical amount based on an antigen-antibody reaction of the composite and the norovirus which is contained in an analyte.

9. The detection device according to claim 8, wherein the physical amount is selected from the group consisting of luminescence intensity, chromaticity, light transmission, turbidness, absorbance, and radiation dose.

10. A detection method comprising:

(a) bringing a composite claim 5 into contact with an analyte; and (b) detecting a change of a physical amount based on an antigen-antibody reaction of the composite and the norovirus which is contained in the analyte.

11. The detection method according to claim 10, wherein the physical amount is selected from the group consisting of luminescence intensity, chromaticity, light transmission, turbidness, absorbance, and radiation dose.

12. An antibody, comprising any one of the amino acid sequences represented by SEQ ID NO: 45-SEQ ID NO:47.

* * * * *